US007351729B2

(12) United States Patent
Stein et al.

(10) Patent No.: US 7,351,729 B2
(45) Date of Patent: Apr. 1, 2008

(54) JNK INHIBITORS FOR USE IN COMBINATION THERAPY FOR TREATING OR MANAGING PROLIFERATIVE DISORDERS AND CANCERS

(75) Inventors: Bernd M. Stein, San Diego, CA (US); John K. Westwick, San Ramon, CA (US); Bruce W. Ennis, Carlsbad, CA (US)

(73) Assignee: Signal Pharmaceuticals, LLC, San Diego, CA (US)

( * ) Notice: Subject to any disclaimer, the term of this patent is extended or adjusted under 35 U.S.C. 154(b) by 426 days.

(21) Appl. No.: 10/384,440

(22) Filed: Mar. 7, 2003

(65) Prior Publication Data

US 2004/0067953 A1    Apr. 8, 2004

Related U.S. Application Data

(60) Provisional application No. 60/362,705, filed on Mar. 8, 2002.

(51) Int. Cl.
*A61K 31/41* (2006.01)
*A61K 31/47* (2006.01)
*A61K 31/44* (2006.01)
*A61K 31/535* (2006.01)

(52) U.S. Cl. .................... 514/381; 514/233.8; 514/256; 514/338; 514/314; 514/383

(58) Field of Classification Search ................ 514/381, 514/233.8, 256, 338, 314, 383
See application file for complete search history.

(56) References Cited

U.S. PATENT DOCUMENTS

| 3,994,890 | A | 11/1976 | Fujimura |
| 4,179,517 | A | 12/1979 | Mechoulam et al. |
| 4,198,518 | A | 4/1980 | Tzikas |
| 4,415,569 | A | 11/1983 | Yasuo et al. |
| 4,788,195 | A | 11/1988 | Torley et al. |
| 4,876,252 | A | 10/1989 | Torley et al. |
| 4,966,622 | A | 10/1990 | Rempfler et al. |
| 4,973,690 | A | 11/1990 | Rempfler et al. |
| 5,013,837 | A | 5/1991 | Ward et al. |
| 5,081,122 | A | 1/1992 | Ward |
| 5,159,078 | A | 10/1992 | Rempfler et al. |
| 5,166,047 | A | 11/1992 | Hioki et al. |
| 5,262,527 | A | 11/1993 | Gregory et al. |
| 5,462,960 | A | 10/1995 | Barth et al. |
| 5,489,505 | A | 2/1996 | Kato et al. |
| 5,516,775 | A | 5/1996 | Zimmermann et al. |
| 5,527,914 | A | 6/1996 | Hioki et al. |
| 5,605,906 | A | 2/1997 | Lau |
| 5,624,941 | A | 4/1997 | Barth et al. |
| 5,804,592 | A | 9/1998 | Volicer |
| 5,925,768 | A | 7/1999 | Barth et al. |
| 5,939,429 | A | 8/1999 | Kunos et al. |
| 5,942,384 | A | 8/1999 | Arai et al. |
| 6,013,648 | A | 1/2000 | Rinaldi et al. |
| 6,162,613 | A | 12/2000 | Su et al. |
| 6,262,112 | B1 | 7/2001 | Mittendorf et al. |
| 6,284,788 | B1 | 9/2001 | Mittendorf et al. |
| 6,897,231 | B2 * | 5/2005 | Bhagwat et al. ............ 514/403 |
| 2003/0235909 | A1 | 12/2003 | Hariri et al. |
| 2004/0028660 | A1 | 2/2004 | Hariri et al. |

FOREIGN PATENT DOCUMENTS

| CS | 146895 | 2/1972 |
| DE | 12 66 763 B | 4/1968 |
| DE | 198 37 627 A1 | 2/2000 |
| DE | 198 37 638 A1 | 2/2000 |
| DE | 100 15 866 A1 | 10/2001 |
| EP | 0 208 211 | 1/1987 |
| EP | 0 494 774 | 1/1992 |
| EP | 0 518 805 | 12/1992 |
| FR | 2 024 807 A | 9/1970 |
| FR | 2 167 626 A | 8/1973 |
| FR | 2 336 708 A | 7/1977 |
| FR | 2 401 915 A | 3/1979 |
| FR | 2 709 912 A1 | 3/1995 |
| FR | 2 789 078 A1 | 8/2000 |
| FR | 2 789 079 A1 | 8/2000 |
| FR | 2 805 810 A1 | 9/2001 |

(Continued)

OTHER PUBLICATIONS http://www.stjude.org/media/0,2561,453_2137_6564,00.html, © 2005 St. Jude Children's Research Hospital. Retrieved Oct. 31, 2005.*

(Continued)

*Primary Examiner*—Cecilia J. Tsang
*Assistant Examiner*—Anna Pagonakis
(74) *Attorney, Agent, or Firm*—Jones Day

(57) ABSTRACT

The present invention relates to methods and compositions designed for the treatment, management or prevention of cancer. The methods of the invention comprise the administration of an effective amount of one or more inhibitors of JNK in combination with the administration of an effective amount of one or more other agents useful for cancer therapy. The invention also provides pharmaceutical compositions comprising one or more inhibitors of JNK in combination with one or more other agents useful for cancer therapy. In particular, the invention is directed to methods of treatment and prevention of cancer by the administration of an effective amount of one or more inhibitors of JNK in combination with standard and experimental chemotherapies, hormonal therapies, bone marrow transplants, stem cell replacement therapies, biological therapies/immunotherapies and/or radiation therapies for treatment or prevention of cancer. Also included are methods of treatment of cancer by the administration of one or more inhibitors of JNK in combination with surgery, alone or in further combination with standard and experimental chemotherapies, hormonal therapies, bone marrow transplants, stem cell replacement therapies, biological therapies/immunotherapies and/or radiation therapies.

8 Claims, 7 Drawing Sheets

FOREIGN PATENT DOCUMENTS

Figure 1A:
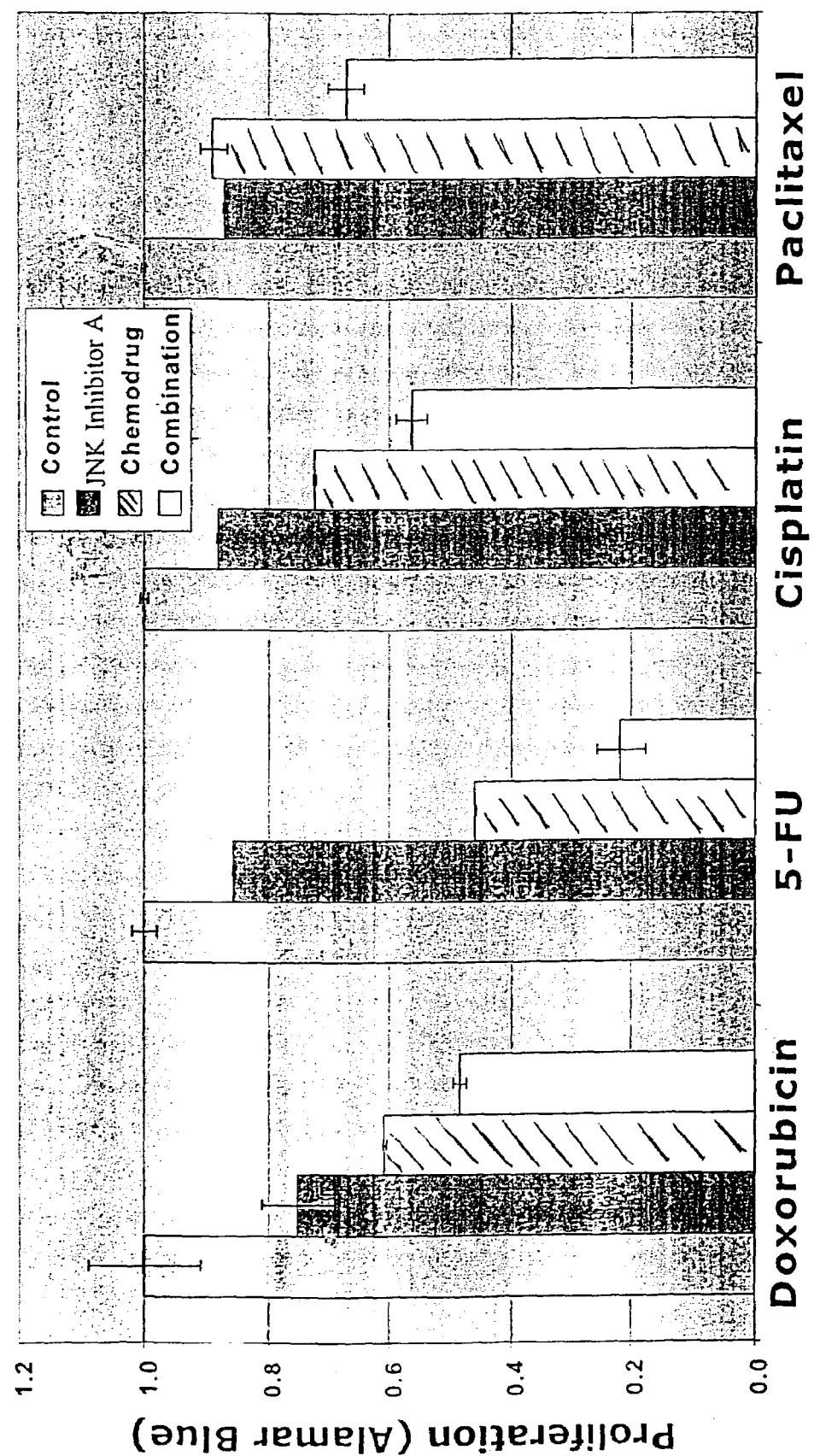

| | | |
|---|---|---|
| FR | 2 805 817 A1 | 9/2001 |
| GB | 1293557 | 9/1970 |
| GB | 1404969 | 8/1973 |
| GB | 1576217 | 7/1977 |
| GB | 2 345 486 A | 7/2000 |
| WO | WO 93/08167 | 4/1993 |
| WO | WO 94/12466 A1 | 6/1994 |
| WO | WO 96/02248 A1 | 2/1996 |
| WO | WO 96/18391 A2 | 6/1996 |
| WO | WO 96/18600 A1 | 6/1996 |
| WO | WO 96/20268 A1 | 7/1996 |
| WO | WO 96/25397 A1 | 8/1996 |
| WO | WO 97/00860 A1 | 1/1997 |
| WO | WO 97/19063 A1 | 5/1997 |
| WO | WO 97/21682 A1 | 6/1997 |
| WO | WO 97/29079 A1 | 8/1997 |
| WO | WO 98/18782 | 5/1998 |
| WO | WO 98/20003 | 5/1998 |
| WO | WO 98/31227 A1 | 7/1998 |
| WO | WO 98/32441 A1 | 7/1998 |
| WO | WO 98/37061 A1 | 8/1998 |
| WO | WO 98/41519 A1 | 9/1998 |
| WO | WO 98/43969 | 10/1998 |
| WO | WO 99/01439 | 1/1999 |
| WO | WO 99/02499 A1 | 1/1999 |
| WO | WO 99/24471 A1 | 5/1999 |
| WO | WO 99/26612 A1 | 6/1999 |
| WO | WO 99/51560 A1 | 10/1999 |
| WO | WO 99/52524 A1 | 10/1999 |
| WO | WO 99/53927 | 10/1999 |
| WO | WO 99/57106 A1 | 11/1999 |
| WO | WO 99/57107 A2 | 11/1999 |
| WO | WO 99/57253 | 11/1999 |
| WO | WO 99/60987 A2 | 12/1999 |
| WO | WO 99/63821 | 12/1999 |
| WO | WO 00/10967 A1 | 3/2000 |
| WO | WO 00/10968 A2 | 3/2000 |
| WO | WO 00/12486 | 3/2000 |
| WO | WO 00/15609 A1 | 3/2000 |
| WO | WO 00/15657 | 3/2000 |
| WO | WO 00/16756 A1 | 3/2000 |
| WO | WO 00/31067 | 6/2000 |
| WO | WO 00/32200 A1 | 6/2000 |
| WO | WO 00/33844 | 6/2000 |
| WO | WO 00/35909 | 6/2000 |
| WO | WO 00/39101 | 7/2000 |
| WO | WO 00/40562 A1 | 7/2000 |
| WO | WO 00/43373 | 7/2000 |
| WO | WO 00/46209 A1 | 8/2000 |
| WO | WO 00/56303 A2 | 9/2000 |
| WO | WO 00/56738 | 9/2000 |
| WO | WO 00/64872 | 11/2000 |
| WO | WO 00/75118 | 12/2000 |
| WO | WO 00/78731 | 12/2000 |
| WO | WO 01/04083 A1 | 1/2001 |
| WO | WO 01/12609 | 2/2001 |
| WO | WO 01/12621 | 2/2001 |
| WO | WO 01/14375 | 3/2001 |
| WO | WO 01/19807 A1 | 3/2001 |
| WO | WO 01/23382 | 4/2001 |
| WO | WO 01/24798 A1 | 4/2001 |
| WO | WO 01/27089 | 4/2001 |
| WO | WO 01/28329 A1 | 4/2001 |
| WO | WO 01/28497 A2 | 4/2001 |
| WO | WO 01/28498 A2 | 4/2001 |
| WO | WO 01/28557 A1 | 4/2001 |
| WO | WO 01/28588 A1 | 4/2001 |
| WO | WO 01/29007 A1 | 4/2001 |
| WO | WO 01/29009 | 4/2001 |
| WO | WO 01/32169 A1 | 5/2001 |
| WO | WO 01/32629 A1 | 5/2001 |
| WO | WO 01/32663 A2 | 5/2001 |
| WO | WO 01/53268 | * 7/2001 |
| WO | WO 01/58445 A1 | 8/2001 |
| WO | WO 01/58450 A2 | 8/2001 |
| WO | WO 01/58869 A2 | 8/2001 |
| WO | WO 01/64212 A1 | 9/2001 |
| WO | WO 01/64632 A1 | 9/2001 |
| WO | WO 01/64633 A1 | 9/2001 |
| WO | WO 01/64634 A1 | 9/2001 |
| WO | WO 01/70700 A1 | 9/2001 |
| WO | WO 01/74763 A1 | 10/2001 |
| WO | WO 01/87297 A1 | 11/2001 |
| WO | WO 01/89589 A1 | 11/2001 |
| WO | WO 01/91749 | 12/2001 |
| WO | WO 01/95899 A2 | 12/2001 |
| WO | WO 01/96330 A2 | 12/2001 |
| WO | WO 01/98289 A1 | 12/2001 |
| WO | WO 02/10135 A1 | 2/2002 |
| WO | WO 02/10137 | 2/2002 |
| WO | WO 02/19383 A2 | 3/2002 |
| WO | WO 02/24630 A1 | 3/2002 |
| WO | WO 02/26702 A1 | 4/2002 |
| WO | WO 02/28346 A2 | 4/2002 |
| WO | WO 02/36590 A1 | 5/2002 |
| WO | WO 02/42248 A2 | 5/2002 |
| WO | WO 02/42269 A1 | 5/2002 |
| WO | WO 02/46170 | 6/2002 |
| WO | WO 02/47691 A1 | 6/2002 |
| WO | WO 02/053543 A1 | 7/2002 |
| WO | WO 02/058636 A2 | 8/2002 |
| WO | WO 02/060447 A1 | 8/2002 |
| WO | WO 02/062750 A1 | 8/2002 |
| WO | WO 02/065997 A1 | 8/2002 |
| WO | WO 02/066450 | 8/2002 |
| WO | WO 02/072562 A1 | 9/2002 |
| WO | WO 02/080903 A1 | 10/2002 |
| WO | WO 02/085396 | 10/2002 |
| WO | WO 02/085866 A1 | 10/2002 |

OTHER PUBLICATIONS

Somasundaram et al. Dietary Curcumin Inhibits Chemotherapy-induced Apoptosis in Models of Human Breast Cancer. Cancer Research 62, 3868-3875, Jul. 1, 2002.*

Iwamura et al., "In Vitro and in Vivo Pharmacological Characterization of JTE-907, a Novel Selective Ligand for Cannabinoid $CB_2$ Receptor," *The Journal of Pharmacology and Experimental Therapeutics*, 2001, pp. 420-425, vol. 296, No. 2, The American Society for Pharmacology and Experimental Therapeutics, USA.

Nagai et al., "Immunoglobulin E production in mice by means of contact sensitization with a simple chemical, hapten," *J. Allergy Clin. Immunol.*, Dec. 1997, pp. S39-S44, vol. 100, No. 6, Part 2, Mosby-Year Book, Inc.

Satoh et al., "Differential Effect of Antiallergic Drugs on IgE-Mediated Cutaneous Reaction in Passively Sensitized Mice," *Pharmacology*, Feb. 2000, pp. 97-104, vol. 60, Karger AG, Basel.

Munro et al., "Molecular characterization of a peripheral receptor for cannabinoids," *Nature*, Sep. 2, 1993, pp. 61-65, vol. 365, No. 6441.

Yamaguchi et al., "Characterization of itch-associated responses of NC mice with mite-induced chronic dermatitis," *Journal of Dermatological Science*, 2001, pp. 20-28, vol. 25, Elsevier.

Ames et al., 1987, "An integrated concept of amebicidal action: electron transfer and oxy radicals", Free Radical Biol. Med. 3:85-96.

Aspenström et al., 1996, "Two GTPases, Cdc42 and Rac, bind directly to a protein implicated in the immunodeficiency disorder Wiskott-Aldrich syndrome", Curr. Biol. 6:70-75.

Baeuerle and Baichwal, 1997, "NF-kappa B as a frequent target for immunosuppressive and anti-inflammatory molecules", *Advances in Immunology* 65:111-137.

Beg et al., 1995, "Embryonic lethality and liver degeneration in mice lacking the RelA component of NF-kappa B", Nature 376(6536):167-70.

Bohrer et al., 1997, "Role of NFkappaB in the mortality of sepsis.", J. Clin. Inv. 100:972-985.

Brand et al., 1997, "Activated transcription factor nuclear factor-kappa B is present in the atherosclerotic lesion", J Clin Inv. 97:1715-1722.

Burke et al., 1999, "Peptides corresponding to the N and C termini of IkappaB-alpha, -beta, and -epsilon as probes of the two catalytic subunits of IkappaB kinase, IKK-1 and IKK-2", Journal of Biological Chemistry 274:36146-36152.

CAS No. 130:153598d for Gwon et al., Direct amination of 6H-anthra(9,1-cd)isothiazol-6-one 2,2-dioxides:, Doki. Akad. Nauk, 359:357-61, 1998.

CAS No. 86:121031 v for Shah et al., "Thiocyanation of 1-aminoanthraquinones", Indian J. Chem. 14b:625-626. 1976.

CAS No. 102:205411f for Mitsubishi Chemical Industries Co., Ltd., JP 60 028,454.

CAS No. 104:208328m for Mitusbishi Chemical Industries Co., Ltd., Jp 60 250,052.

CAS No. 103:143360y for Mitsubishi Chemical Industries Co., Ltd., JP 60 92,355.

Chen et al., 1996, "Activation and inhibition of the AP-1 complex in human breast cancer cells", Mol. Carcinogenesis 15:215-226.

Cramer et al., 1999, "A firm hand on NFkappaB: structures of the IkappaBalpha-NFkappaB complex", Structure 7:R1-R6.

Deacon et al., 1999, "MEK kinase 3 directly activates MKK6 and MKK7, specific activators of the p38 and c-Jun NH2-terminal kinases", J. Biol. Chem. 274:16604-16610.

Delhase et al., 1999, "Positive and negative regulation of IkappaB kinase activity through IKKbeta subunit phosphorylation", Science 284:309 313.

Dong et al., 1998, "Defective T cell differentiation in the absence of Jnk1", Science 282:2092-2095.

Faris et al., 1996, "Regulation of interleukin-2 transcription in inducible stabile expression of dominant negative and dominant active mitogen-activated protein kinase kinase kinase in Jurkat T cells", J. Biol. Chem. 271:27366-27373.

Galushko and Dokunikhin, 1997, "Pyrazoloanthrone derivatives I. Reactivity of 3-aminopyrazoloanthrone", Khimiya Geterotsiklicheskikh Soedinenii, 7:956-961.

Gosset et al., 1995, "Expression of E-selectin, ICAM-I and VCAM-I on bronchial biopsies from allergic and non-allergic asthmatic patients", Int Arch Allergy Immunol. 106:69-77.

Gum et al., 1997, "Regulation of 92 kDa type IV collagenase expression by the jun aminoterminal kinase- and the extracellular signal-regulated kinase- dependent signaling cascades", Oncogene 14:1481-1493.

Gvon et al., 1994, "Amino-imino tautomerism and intramolecular cyclization of 4, 9-diamino-1, 10-anthraquinone-1—tosylimines" Dokl. Akad. Nauk, 334:465-468 (in Russian with English abstract).

Han et al., 1999, "Jun N-terminal kinase in rheumatoid arthritis", J. Pharmacol. Exp. Therap. 291:124-130.

Hartley et al., 1988, "Characteristics of the interaction of anthrapyrazole anticancer agents with deoxyribonucleic acids: structural requirements for DNA binding, intercalation, and photosensitization", Mol. Pharmacol. 33:265-271.

Herdegen et al., 1998, "Lasting N-terminal phosphorylation of c-Jun and activation of c-Jun N-terminal kinases after neuronal injury", J. Neurosci. 18:5124-5135.

Hibi et al., 1993, "Identification of an oncoprotein- and UV-responsive protein kinase that binds and potentiates the c-Jun activation domain", Genes Dev. 7:2135-2148.

Hirosumi et al., 2002, "A central role for JNK in obesity and insulin resistance", Letters to Nature 420:333-336.

Hu et al., 1999, "Abnormal morphogenesis but intact IKK activation in mice lacking the IKKalpha subunit of IkappaB kinase", Science 284:316-320.

Ishizuka et al., 1997, "Mast cell tumor necrosis factor α production is regulated by MEK kinases", Proc. Natl. Acad. Sci. USA 94:6358-6363.

Ivanova et al., 1997,"XPS investigation of electronic structure of pyrazolanthrone and its derivatives" Poverkhnost, 4-5:193-201.

Judson, 1992, "The anthrapyrazoles: a new class of compounds with clinical activity in breast cancer", Semin. Oncol. 19:687-694.

Karin et al., 1997, "AP-1 function and regulation", Curr. Opin. Cell. Biol. U9:240-246.

Kiyooka et al., 1990, "Photochemical Intramolecular Cyclization Reactions of Acylgermanes", Jr. J. Org. Chem. 55, 5562-4.

Koch et al., 1995, "Angiogenesis mediated by soluble forms of E-selectin and vascular cell adhesion molecule-1", Nature 376:517-519.

Lange-Carter et al., 1993, "A divergence in the MAP kinase regulatory network defined by MEK kinase and Raf", Science 260:315-319.

Li et al., 1996, "Blocked signal transduction to the ERK and JNK protein kinases in anergic CD4+ T cells", Science 271:1272-1276.

Li et al., 1996, "The Ras-JNK pathway is involved in shear-induced gene expression", Mol. Cell. Biol. 16:5947-5954.

Li et al., 1999, "IKK1-deficient mice exhibit abnormal development of skin and skeleton", Genes & Development 13:1322-1328.

Li et al., 1999, "Severe liver degeneration in mice lacking the IkappaB kinase 2 gene.", Science 284:321-324.

Lin et al., 1995, "Identification of a dual specificity kinase that activates the Jun kinases and p38-Mpk2", Science 268:286-290.

Maj et al, 1992, "PNU 151774E protects against kainate-induced status epilepticus and hippocampal lesions in the rat", Eur. J. Pharm. 359:27-32, 1992.

Malinin et al., 1997, MAP3K-related kinase involved in NF-kappaB induction by TNF, CD95 and IL-1, Nature 385:540-544.

Manning and Mercurio, 1997, "Transcription inhibitors in inflammation", Exp. Opin. Invest. Drugs 6:555-567.

Maroney et al., 1998, "Motoneuron apoptosis is blocked by CEP-1347 (KT 7515), a novel inhibitor of the JNK signaling pathway", J. Neurosci. 18:104-111.

Mercurio et al., 1997, "IKK-1 and IKK-2: cytokine-activated IkappaB kinases essential for NF-kappaB activation", Science 278:860-866.

Mercurio et al., 1999, "IkappaB kinase (IKK)-associated protein 1, a common component of the heterogeneous IKK complex", Mol Cell Biol. 19:1526-1538.

Mielke et al., 2000, "JNK and p38 stresskinases—degenerative effectors of signal-transduction-cascades in thenervous system", Prog. Neurobiol. 61:45-60.

Milne et al., 1995, "p53 is phosphorylated in vitro and in vivo by an ultraviolet radiation-induced protein kinase characteristic of the c-Jun kinase, JNK1", J. Biol. Chem. 270:5511-5518.

Mohit et al., 1995, "p49$^{3F12}$ kinase: a novel MAP kinase expressed in a subset of neurons in the human nervous system", Neuron 14:67-78.

Nishina et al., 1997, "Impaired CD28-mediated interleukin 2 production and proliferation in stress kinase SAPK/ERK1 kinase (SEK1)/mitogen-activated protein kinase kinase 4 (MKK4)-deficient T lymphocytes", J. Exp. Med. 186:941-953.

Okamoto et al., 1997, "Selective activation of the JNK/AP-1 pathway in Fas-mediated apoptosis of rheumatoid arthritis synoviocytes", Arthritis & Rheumatism 40:919-926.

Panes et al., 1995, "Regional differences in constitutive and induced ICAM-1 expression in vivo", Am J Physiol. 269:H1955-H1964.

Peet and Li, 1999, "kappaB kinases alpha and beta show a random sequential kinetic mechanism and are inhibited by staurosporine and quercetin", Journal of Biological Chemistry 274:32655-32661.

Pombo et al., 1994, "The stress-activated protein kinases are major c-Jun amino-terminal kinases activated by ischemia and reperfusion", J. Biol. Chem. 269:26546-26551.

Raitano et al., 1995, "The Bcr-Abl leukemia oncogene activates Jun kinase and requires Jun for transformation", Proc.Natl. Acad. Sci. USA 92:11746-11750.

Sabapathy et al., 1999, "JNK2 is required for efficient T-cell activation and apoptosis but not for normal lymphocyte development", Curr. Biol. 9:116-125.

Saporito et al., 1998, Preservation of cholinergic activity and prevention of neuron death by CEP-1347/KT-7515 following excitotoxic injury of the nucleus basalis magnocellularis:, *Neuroscience* 86:461-472.

Saporito et al., 1999, "CEP-1347/KT-7515, an inhibitor of c-jun N-terminal kinase activation, attenuates the 1-methyl-4-phenyl tetrahydropyridine-mediated loss of nigrostriatal dopaminergic neurons In vivo", *J Pharmacol Exp Ther.* 288(2):421-7.

Showalter et al, "Design, Tumor Biology, and Biochemical Pharmacology of Anthrapyrazoles" Bioact Mol. Chapter V1:201-243 (1988).

Showalter et al., 1984, "5-[(Aminoalkyl)amino]-substituted anthra[1,9-*cd*]pyrazol-6(2*H*)-ones as novel anticancer agents. Synthesis and biological evaluation", J. Med. Chem. 27:253-255.

Showalter et al., 1987, "Anthrapyrazole anticancer agents. Synthesis and structure-activity relationships against murine leukemias", J. Med. Chem. 30:121-131.

Singh and Shah, 1978, "Reactions of 2,2'-ethylene-bis-anthrapyrazolone", Indian J. -Chem. 16B:100-102.

Sokolyuk et al., 1992, "Synthesis and photochemical properties of peri-phenoxy derivatives of 6H-anthra[1,9-cd]-6-pyrazolone (pyrazolanthrone)", Zhurnal Organicheskoi Khimii 28:2193-200.

Spiegelman et al., "regulation of Adipocyte Gene Expression in Differentiation and Syndromes of Obesity/Diabetes" J. Of Biol. Chem 268:6823-6826 (1993).

Su et al., 1994, "JNK is involved in signal integration during costimulation of T lymphocytes", Cell 77:727-736.

Swantek et al., 1997, "Jun N-terminal kinase/stress-activated protein kinase (JNK/SAPK) is required for lipopolysaccharide stimulation of tumor necrosis factor alpha (TNF-α) translation: glucocorticoids inhibit TNF-α translation by blocking JNK/SAPK", Mol. Cell. Biol. 17:6274-6282.

Szabo et al., 1996, "Altered cJUN expression: an early event in human lung carcinogenesis", Cancer Res. 56:305-315.

Takeda et al., 1999, "Limb and Skin Abnormalities in Mice Lacking IKKα", *Science* 284:313-316, 1999.

Tanaka et al., 1999, "Embryonic lethality, liver degeneration, and impaired NF-kappa B activation in IKK-beta-deficient mice", *Immunity* 10:421-429.

Teramoto et al., 1996, "Signaling from the small GTP-binding proteins Rac1 and Cdc42 to the c-Jun N-terminal kinase/stress-activated protein kinase pathway. A role for mixed lineage kinase 3/protein-tyrosine kinase 1, a novel member of the mixed lineage kinase family", *J. Biol. Chem.* 271:27225-27228.

Tournier et al., 1997, "Mitogen-activated protein kinase kinase 7 is an activator of the c-Jun $NH_2$-terminal kinase", Proc. Natl. Acad. Sci. USA 94:7337-7342.

Web page printout of Dec. 18, 2002 for http://www.calbiochem.com/Products/PrdocutDetail_CBCB.asp?cat NO=420119 (cat. No. 420119).

Whitmarsh and Davis, 1996, "Transcription factor AP-1 regulation by mitogen-activated protein kinase signal transduction pathways", Mol. Med. 74:589-607.

Winter et al, *Arthritis and Rheumatism* 9(3):394-404, 1966; Weichman et al, *Pharmacological Methods in the Control of Inflammation*, Chang and Lewis Eds., Alan R. Liss, Inc., Publ., New York, 1989.

Yan et al., 1994, "Activation of stress-activated protein kinase by MEKK1 phosphorylation of its activator SEK1", Nature 372:798-800.

Yang et al., 1997, "Absence of excitotoxicity-induced apoptosis in the hippocampus of mice lacking the Jnk3 gene", *Nature* 389:865-870.

Yang et al., 1998, "Differentiation of $CD4^+$ T cells to Th1 cells requires MAP kinase JNK2", Immunity 9:575-585.

Yaron et al., 1998, "Identification of the receptor component of the IkappaBalpha-ubiquitin ligase", *Nature 396*:590-594.

Yin et al., 1997, "Tissue-specific pattern of stress kinase activation in ischemic/reperfused heart and kidney", J. Biol. Chem. 272:19943-19950.

Yujiri et al., 1998, "Role of MEKK1 in cell survival and activation of JNK and ERK pathways defined by targeted gene discruption", *Science* 282:1911-1914.

Zwacka et al., 1998, "Redox gene therapy for ischemia/reperfusion injury of the liver reduces AP1 and NF-kappaB activation.", *Nature Medicine* 4:698-704.

Force et al., "Inhibitors of Protein Kinase Signaling Pathways—Emerging Therapies for Cardiovascular Disease," *Circulation 109*:1196-1205 (2004).

* cited by examiner

JNK INHIBITORS FOR USE IN COMBINATION THERAPY FOR TREATING OR MANAGING PROLIFERATIVE DISORDERS AND CANCERS

This application claims the benefit of U.S. provisional application 60/362,705, filed Mar. 8, 2002, the contents of which are incorporated by reference herein in their entirety.

1. FIELD OF THE INVENTION

The invention relates to combination therapies for the treatment, prevention or management of a disease or disorder in cancer patients or patients having other proliferative diseases or disorders.

2. BACKGROUND OF THE INVENTION

Jun N-Terminal Kinase (JNK)

The Jun N-terminal kinase (JNK) pathway is activated by exposure of cells to environmental stress or by treatment of cells with pro-inflammatory cytokines and growth factors. Targets of the JNK pathway include the transcription factors c-jun and ATF2 (Whitmarsh A. J., and Davis R. J. *J. Mol. Med.* 74:589-607, 1996). These transcription factors are members of the basic leucine zipper (bZIP) group that bind as homo- and hetero-dimeric complexes to AP1 and AP-1-like sites in the promoters of many genes (Karin M., Liu Z. G. and Zandi E. *Curr Opin Cell Biol* 9:240-246, 1997). JNK binds to the N-terminal region of c-jun and ATF-2 and phosphorylates two sites within the activation domain of each transcription factor (Hibi M., Lin A., Smeal T., Minden A., Karin M. *Genes Dev.* 7:2135-2148, 1993; Mohit A. A., Martin M. H., and Miller C. A. *Neuron* 14:67-78, 1995). Three JNK enzymes have been identified as products of distinct genes (Hibi et al, supra; Mohit et al., supra). Ten different isoforms of JNK have been identified. These represent alternatively spliced forms of three different genes: JNK1, JNK2, and JNK3. JNK1 and 2 are ubiquitously expressed in human tissues, whereas JNK3 is selectively expressed in the brain, heart, and testis (Dong, C., Yang, D., Wysk, M., Whitmarsh, A., Davis, R., Flavell, R. *Science* 270:1-4, 1998). Gene transcripts are alternatively spliced to produce four-JNK1 isoforms, four-JNK2 isoforms, and two-JNK3 isoforms. JNK1 and 2 are expressed widely in mammalian tissues, whereas JNK3 is expressed almost exclusively in the brain. Selectivity of JNK signaling is achieved via specific interactions of JNK pathway components and by use of scaffold proteins that selectively bind multiple components of the signaling cascade. JIP-1 (JNK-interacting protein-1) selectively binds the MAPK module, MLK→JNKK1→JNK. It has no binding affinity for a variety of other MAPK cascade enzymes. Different scaffold proteins are likely to exist for other MAPK signaling cascades to preserve substrate specificity.

JNKs are activated by dual phosphorylation on Thr-183 and Tyr-185. JNKK1 (also known as MKK 4) and JNKK2 (MKK7), two MAPKK level enzymes, can mediate JNK activation in cells (Lin A., Minden A., Martinetto H., Claret F.-Z., Lange-Carter C., Mercurio F., Johnson G. L., and Karin M. *Science* 268:286-289, 1995; Tournier C., Whitmarsh A. J., Cavanagh J., Barrett T., and Davis R. J. *Proc. Nat. Acad. Sci. USA* 94:7337-7342, 1997). JNKK2 specifically phosphorylates JNK, whereas JNKK1 can also phosphorylate and activate p38. Both JNKK1 and JNKK2 are widely expressed in mammalian tissues. JNKK1 and JNKK2 are activated by the MAPKKK enzymes, MEKK1 and 2 (Lange-Carter C. A., Pleiman C. M., Gardner A. M., Blumer K. J., and Johnson G. L., *Science*, 260:315-319, 1993; Yan M., Dai J. C., Deak J. C., Kyriakis J. M., Zon L. I., Woodgett J. R., and Templeton D. J., *Nature*, 372:798-781, 1994). Both MEKK1 and MEKK2 are widely expressed in mammalian tissues.

Activation of the JNK pathway has been documented in a number of disease settings, providing the rationale for targeting this pathway for drug discovery. In addition, molecular genetic approaches have validated the pathogenic role of this pathway in several diseases. For example, autoimmune and inflammatory diseases arise from the over-activation of the immune system. Activated immune cells express many genes encoding inflammatory molecules, including cytokines, growth factors, cell surface receptors, cell adhesion molecules, and degradative enzymes. Many of these genes are regulated by the JNK pathway, through activation of the transcription factors AP-1 and ATF-2, including TNF-alpha, IL-2, E-selectin, and matrix metalloproteinases such as collagenase-1 (Manning A. M. and Mercurio F., *Exp Opin Invest Drugs*, 6: 555-567, 1997). Monocytes, tissue macrophages, and tissue mast cells are key sources of TNF-alpha production. The JNK pathway regulates TNF-alpha production in bacterial lipopolysaccharide-stimulated macrophages, and in mast cells stimulated through the FceRII receptor (Swantek J. L., Cobb M. H., Geppert T. D., *Mol. Cell. Biol.*, 17:6274-6282, 1997; Ishizuka, T., Tereda N., Gerwins, P., Hamelmann E., Oshiba A., Fanger G. R., Johnson G. L., and Gelfiand E. W., *Proc. Nat. Acad. Sci. USA*, 94:6358-6363, 1997). Inhibition of JNK activation effectively modulates TNF-alpha secretion from these cells. The JNK pathway therefore regulates production of this key pro-inflammatory cytokine. It is believed that JNK is pro-apoptotic under stress or inflammatory conditions such as exposure to UV-radiation. (Leppa and Bohman, *Oncogene* 18:6158-6162 (1999)). Matrix metalloproteinases (MMPs) promote cartilage and bone erosion in rheumatoid arthritis, and generalized tissue destruction in other autoimmune diseases. Inducible expression of MMPs, including MMP-3 and MMP-9, type II and IV collagenases, are regulated via activation of the JNK pathway and AP-1 (Gum, R., Wang, H., Lengyel, E., Juarez, J., and Boyd, D., *Oncogene*, 14:1481-1493, 1997). In human rheumatoid synoviocytes activated with TNF-alpha, IL-1, or Fas ligand the JNK pathway is activated (Han Z., Boyle D. L., Aupperle K. R., Bennett B., Manning A. M., Firestein G. S., *J. Pharm. Exp. Therap.*, 291:1-7, 1999; Okamoto K., Fujisawa K., Hasunuma T., Kobata T., Sumida T., and Nishioka K., *Arth & Rheum*, 40: 919, 1997). Inhibition of JNK activation results in decreased AP-1 activation and collagenase-1 expression (Han et al., supra). The JNK pathway therefore regulates MMP expression in cells involved in rheumatoid arthritis.

Role of JNK in Cancer and Stroke

Cancer is characterized by uncontrolled growth, proliferation and migration of cells. Cancer is the second leading cause of death with 500,000 deaths and an estimated 1.3 million new cases in the United States in 1996. The role of signal transduction pathways contributing to cell transformation and cancer is a generally accepted concept. The JNK pathway leading to AP-1 appears to play a critical role in cancer. Expression of c-jun is altered in early lung cancer and may mediate growth factor signaling in non-small cell lung cancer (Yin T., Sandhu G., Wolfgang C. D., Burrier A., Webb R. L., Rigel D. F. Hai T., and Whelan J., *J. Biol. Chem.*

272:19943-19950, 1997). Indeed, over-expression of c-jun in cells results in transformation, and blocking c-jun activity inhibits MCF-7 colony formation (Szabo E., Riffe M., Steinberg S. M., Birrer M. J., Linnnoila R. I., *Cancer Res.* 56:305-315, 1996). DNA-damaging agents, ionizing radiation, and tumor necrosis factor activate the JNK pathway. In addition to regulating c-jun production and activity, JNK activation can regulate phosphorylation of p53 and, thus, can modulate cell cycle progression (Chen T. K., Smith L. M., Gebhardt D. K., Birrer M. J., Brown P. H,. *Mol. Carcinogenesis*, 15:215-226, 1996). The oncogene BCR-Abl, associated with t(9,22) Philadelphia chromosome translocation of chronic myelogenous leukemia, activates JNK and leads to transformation of hematopoietic cells (Milne D. M., Campbell L. E., Campbell D. G., Meek D. W., *J. Biol. Chem.* 270:5511-5518, 1995). Selective inhibition of JNK activation by a naturally occurring JNK inhibitory protein, called JIP-1, blocks cellular transformation caused by BCR-Abl expression (Raitano A. B., Halpern J. R., Hambuch T. M., Sawyers C. L., *Proc. Nat. Acad. Sci USA*, 92:11746-11750, 1995). Thus, JNK inhibitors may block transformation and tumor cell growth.

JNK is also believed to partly responsible for cancer and/or tumor resistance to certain chemotherapeutics. The number one cause of cancers refractory against traditional chemo drugs is the upregulation of the mdr1 gene. The mdr1/p-glycoprotein gene has an AP-1 binding site in its promoter and is believed to be stimulated by JNK. Upregulation of JNK activity has also been found in tamoxifen-resistant tumors. DN-Jun inhibits tumor growth in tamoxifen-resistant animals and delays development of tamoxifen-resistant phenotype (Daschner, et al. *Breast Cancer Res.* 53:229, 1999; Schiff, et al. *J. Natl. Cancer Inst.* 92:1926, 2000).

Stroke is the $3^{rd}$ leading cause of death and a leading cause of disability in the U.S. Stroke, along with neurodegenerative diseases, such as Alzheimer's (AD) and Parkinson's disease (PD) impose a huge burden on the health care industry by impacting the quality of life of those affected. Loss of neuronal cell populations in stroke, AD, or PD underlies the motor and/or cognitive deficiencies in these patient populations. The mechanism by which neurons die in response to insult has not been fully elucidated; however, activation of the JNK pathway has been implicated as a major signaling pathway for neuronal apoptosis. (For review see Mielke K. and Herdegen T. *Prog. Neurobiol.* 61:45-60, 2000). There have been a number of conflicting reports as to the role of JNK activity in the regulation of apoptosis. Some studies suggest that activating JNK activity induces phosphorylation of C-Jun protein and protects cells from apoptosis (Potapova, O., Basu, S., Mercola, D., Holbrook, N., *J. Biol. Chem.* 276:28546-28553, 2001). However, both pro-survival and pro-apoptotic roles of activated JNK activity have also been described (Kolbus, A., Herr, I., Schreiber, M., Piu, F., Beeche, M., Wagner, E. F., Karin, M., 103:897-907, 2000; Wisdom, R., Johnson, R. S., Moore, C., *EMBO J.*, 18:1888-197, 1999). A variety of insults have been shown to activate the JNK pathway in neurons. For example, activation of JNKs and phosphorylation of c-jun has been shown in brains of rats subjected to axotomy or ischemia with reperfusion, where neuronal cell loss was observed (Herdegen T., Claret F.-X., Kallunki, T., Matin-Villalba A., Winter C., Hunter T. and Karin M. *J. Neurosci.* 18:5124-5135, 1998). Further, inhibition of the mixed lineage kinase (MLK)-3, an upstream kinase in the JNK pathway, by CEP-1347 prevented motor neuron cell death following growth factor withdrawal in vitro (Maroney A. C., Glicksman M. A., Basma A. N., Walton K. M., Knight Jr. E., Murphy C. A., Bartlett B. A., Finn J. P., Angeles T., Matsuda Y., Neff N. T. and Dionne C. A., *J. Neurosci.* 18:104-111, 1998), protected cholinergic neurons following excitotoxic injury of the nucleus basalis magnocellularis (Saporito M. S., Brown, E. R., Miller M. S., Murakata C., Neff N. H., Vaught J. L., and Carswell S. *Neuroscience* 86:461-472, 1998), and blocked the degeneration of midbrain dopamine neurons in mice treated with the neurotoxin, 1-methyl-4-phenyl tetrahydropyridine (Saporito M. S., Brown E. M., Miller M. S. and Carswell S. *J. Pharm. Exp. Ther.*, 1999). While JNK1 and JNK2 enzymes have a widespread tissue distribution, JNK3 is selectively expressed in brain and to a lesser extent in the heart and testis (Dong C., Yang D., Wysk M., Whitmarsh A., Davis R., and Flavell R. *Science* 270:1-4, 1998). Because of this restricted distribution, JNK3 may be the prevailing kinase mediating neuronal apoptosis. In support of JNK3's involvement in neuronal apoptosis, disruption of the gene encoding JNK3 in mice confers resistance to kainic acid—induced seizures and subsequent hippocampal neuronal cell death (Yang D. D., Kuan C.-Y., Whitmarsh A. J., Rincon M., Zheng T. S., Davis R. J., Rakic P. and Flavell R. A. *Nature* 389:865-870, 1997). Mounting evidence points to a role for the JNK pathway in neuronal apoptosis. Therefore, selective JNK inhibitors should prevent neuronal cell death observed in disorders and diseases of the CNS.

Cancer Therapy

Currently, cancer therapy may involve surgery, chemotherapy, hormonal therapy and/or radiation treatment to eradicate neoplastic cells in a patient (see, for example, Stockdale, 1998, "Principles of Cancer Patient Management", in Scientific American: Medicine, vol. 3, Rubenstein and Federman, eds., Chapter 12, Section IV). Recently, cancer therapy could also involve biological therapy or immunotherapy. All of these approaches pose significant drawbacks for the patient. Surgery, for example, may be contraindicated due to the health of the patient or may be unacceptable to the patient. Additionally, surgery may not completely remove the neoplastic tissue. Radiation therapy is only effective when the neoplastic tissue exhibits a higher sensitivity to radiation than normal tissue, and radiation therapy can also often elicit serious side effects. Hormonal therapy is rarely given as a single agent and although can be effective, is often used to prevent or delay recurrence of cancer after other treatments have removed the majority of the cancer cells. Biological therapies/immunotherapies are limited in number and may produce side effects such as rashes or swellings, flu-like symptoms, including fever, chills and fatigue, digestive tract problems or allergic reactions.

With respect to chemotherapy, there are a variety of chemotherapeutic agents available for treatment of cancer. A significant majority of cancer chemotherapeutics act by inhibiting DNA synthesis, either directly, or indirectly by inhibiting the biosynthesis of the deoxyribonucleotide triphosphate precursors, to prevent DNA replication and concomitant cell division (see, for example, Gilman et al., Goodman and Gilman's: The Pharmacological Basis of Therapeutics, Eighth Ed. (Pergamom Press, New York, 1990)). These agents, which include alkylating agents, such as nitrosourea, anti-metabolites, such as methotrexate and hydroxyurea, and other agents, such as etoposides, campathecins, bleomycin, doxorubicin, daunorubicin, etc., although not necessarily cell cycle specific, kill cells during S phase because of their effect on DNA replication. Other agents, specifically colchicine and the vinca alkaloids, such as vinblastine and vincristine, interfere with microtubule assembly resulting in mitotic arrest. Chemotherapy protocols generally involve administration of a combination of chemotherapeutic agents to increase the efficacy of treatment.

Despite the availability of a variety of chemotherapeutic agents, chemotherapy has many drawbacks (see, for example, Stockdale, 1998, "Principles Of Cancer Patient Management" in Scientific American Medicine, vol. 3, Rubenstein and Federman, eds., ch. 12, sect. 10). Almost all chemotherapeutic agents are toxic, and chemotherapy causes significant, and often dangerous, side effects, including severe nausea, bone marrow depression, immunosuppression, etc. Additionally, even with administration of combinations of chemotherapeutic agents, many tumor cells are resistant or develop resistance to the chemotherapeutic agents. In fact, those cells resistant to the particular chemotherapeutic agents used in the treatment protocol often prove to be resistant to other drugs, even those agents that act by mechanisms different from the mechanisms of action of the drugs used in the specific treatment; this phenomenon is termed pleiotropic drug or multidrug resistance. Thus, because of drug resistance, many cancers prove refractory to standard chemotherapeutic treatment protocols.

There is a significant need for alternative cancer treatments, particularly for treatment of cancer that has proved refractory to standard cancer treatments, such as surgery, radiation therapy, chemotherapy, and hormonal therapy. Further, it is uncommon for cancer to be treated by only one method. Thus, there is a need for development of new therapeutic agents for the treatment of cancer and new, more effective, therapy combinations for the treatment of cancer.

There is also a clear need for cancer chemotherapeutics or therapeutic regimens for treating cancer patients while reducing or avoiding the toxicities and/or side effects associated with conventional therapies.

Citations or identification of any reference in Section 2 of this application is not to be construed that such reference is prior art to the present application.

3. SUMMARY OF THE INVENTION

The present invention is based, in part, on the recognition that inhibitors of JNK potentiate and synergize with, enhance the effectiveness of, improve the tolerance of, and/or reduce side effects caused by, other cancer therapies, including conventional and experimental chemotherapies, hormonal therapies, bone marrow transplants, stem cell replacement therapies, biological therapies/immunotherapies and radiation therapies. Thus, the invention encompasses treatment regimens or protocols that provide better therapeutic profiles than current single agent therapies or current combination therapy regimens. Encompassed by the invention are combination therapies that have additive potency or an additive therapeutic effect. The invention also encompasses synergistic combinations where the therapeutic efficacy is greater than additive. Preferably, such combinations also reduce or avoid unwanted or adverse effects. In certain embodiments, the combination therapies encompassed by the invention provide an improved overall therapy relative to administration of either a JNK inhibitor or any other cancer therapy alone. Given the invention, in certain embodiments, doses of existing or experimental cancer therapies can be reduced or administered less frequently which increases patient compliance, improves therapy and reduces unwanted or adverse effects.

In one embodiment, the inhibitor of JNK is a small organic molecule capable of directly inhibiting JNK activity. In another embodiment, the inhibitor of JNK is an antibody or a fragment thereof that immunospecifically binds to JNK or another component of the JNK pathway thus inhibiting JNK activity.

Accordingly, the present invention relates to pharmaceutical compositions and prophylactic and therapeutic regimens designed to prevent, treat, or manage cancer in a patient comprising administering one or more inhibitors of JNK in combination with one or more other cancer therapies other than the administration of a JNK inhibitor. In particular, the present invention provides methods of preventing, treating, or managing cancer in a patient comprising administering to said patient a therapeutically or prophylactically effective of one or more inhibitors of JNK in combination with the administration of a therapeutically or prophylactically effective amount of one or more chemotherapies, hormonal therapies, bone marrow transplants, stem cell replacement therapies, biological therapies/immunotherapies and/or radiation therapies other than the administration of a JNK inhibitor. It is also contemplated that such methods can include the administration of one or more JNK inhibitors in combination with surgery, alone or in combination with the administration of one or more chemotherapies, hormonal therapies, bone marrow transplants, stem cell replacement therapies, biological therapies/immunotherapies and/or radiation therapies other than the administration of a JNK inhibitor. In certain embodiments, the administration of inhibitors of JNK and the other cancer therapies is a therapeutic or prophylactic regimen or protocol. Such methods and regimens can encompass concurrent, sequential, synchronized or alternating/cyclic administration of the inhibitors of JNK with one or more other cancer therapies.

The present invention is directed to methods of treating or preventing cancer by administering an effective amount of JNK inhibitor to a patient in need thereof (referred to herein as a "patient"), typically a warm-blooded animal (including a human) in combination with one or more anti-cancer agents or radiation therapy or both. Prior to administration, one or more compounds of this invention are typically formulated as a pharmaceutical composition which contains an effective dosage amount of one or more of such compounds in combination with one (or more) pharmaceutically acceptable carrier(s). Conditions that may be treated by the compounds of this invention, or a pharmaceutical composition containing the same, include cancer.

In one embodiment, the JNK inhibitor is 2H-Dibenzo(cd, g) indazol-6-one. In another embodiment, the JNK inhibitor is 3-(4-fluoro-phenyl)-5-(2H-(1,2,4) triazol-3-yl)-1H-indazole. In another embodiment, the JNK inhibitor is 3-(4-(2-Piperidin-1-yl-ethoxy)-cyclohexa-1,5-dienyl)-5-(2H-(1,2,4) triazol-3-yl)-1H-indazole.

These and other aspects of this invention will be evident upon reference to the following detailed description. To that end, certain patent and other documents are cited herein to more specifically set forth various aspects of this invention. Each of these documents are hereby incorporated by reference herein in their entirety.

3.1. BRIEF DESCRIPTION OF THE FIGURES

FIG. 1A: FIG. 1A shows the effect of JNK inhibitor A (2H-Dibenzo(cd,g) indazol-6-one) in combination with various chemotherapeutic agents on Lewis Lung Carcinoma (LLC) proliferation.

Figure 1B:
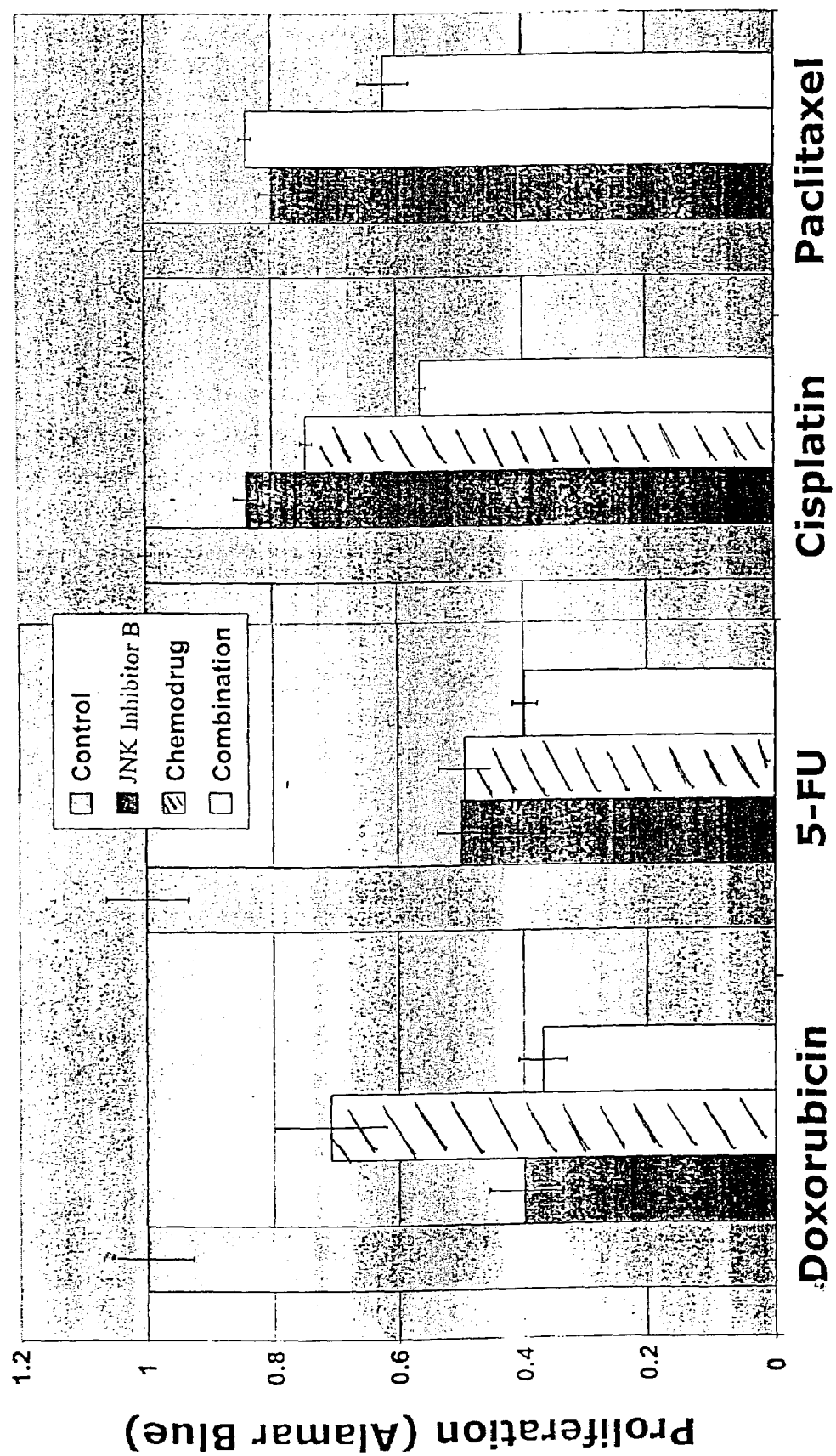

FIG. 1B: FIG. 1B shows the effect of JNK inhibitor B (3-(4-fluoro-phenyl)-5-(2H-(1,2,4) triazol-3-yl)-1H-indazole) in combination with various chemotherapeutic agents on tumor cell proliferation.

Figure 2:
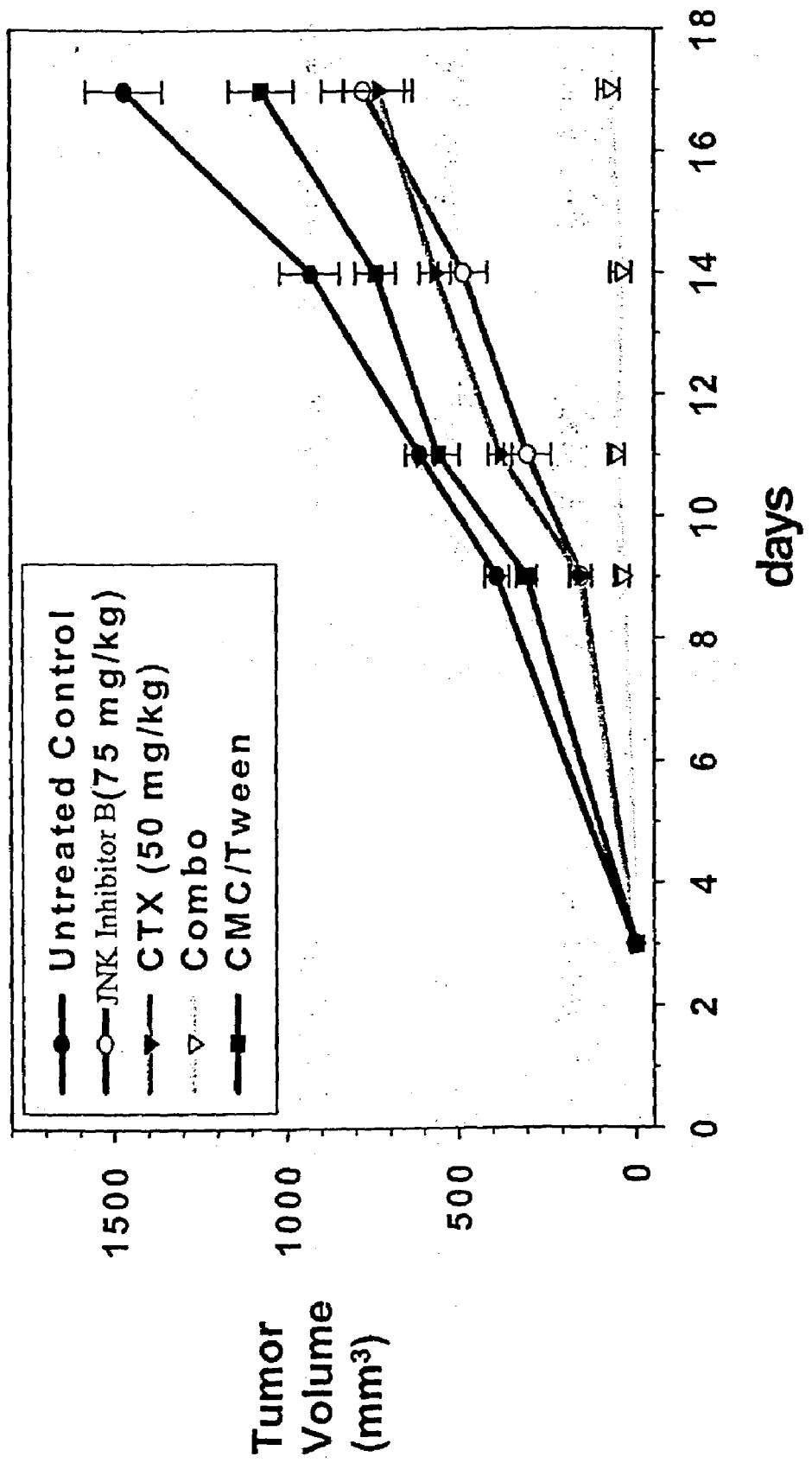

FIG. 2: FIG. 2 shows the JNK inhibitor B (3-(4-fluorophenyl)-5-(2H-(1,2,4)triazol-3-yl)-1H-indazole) in combination with cyclophosphamide, a chemotherapeutic agent on tumor growth.

Figure 3:
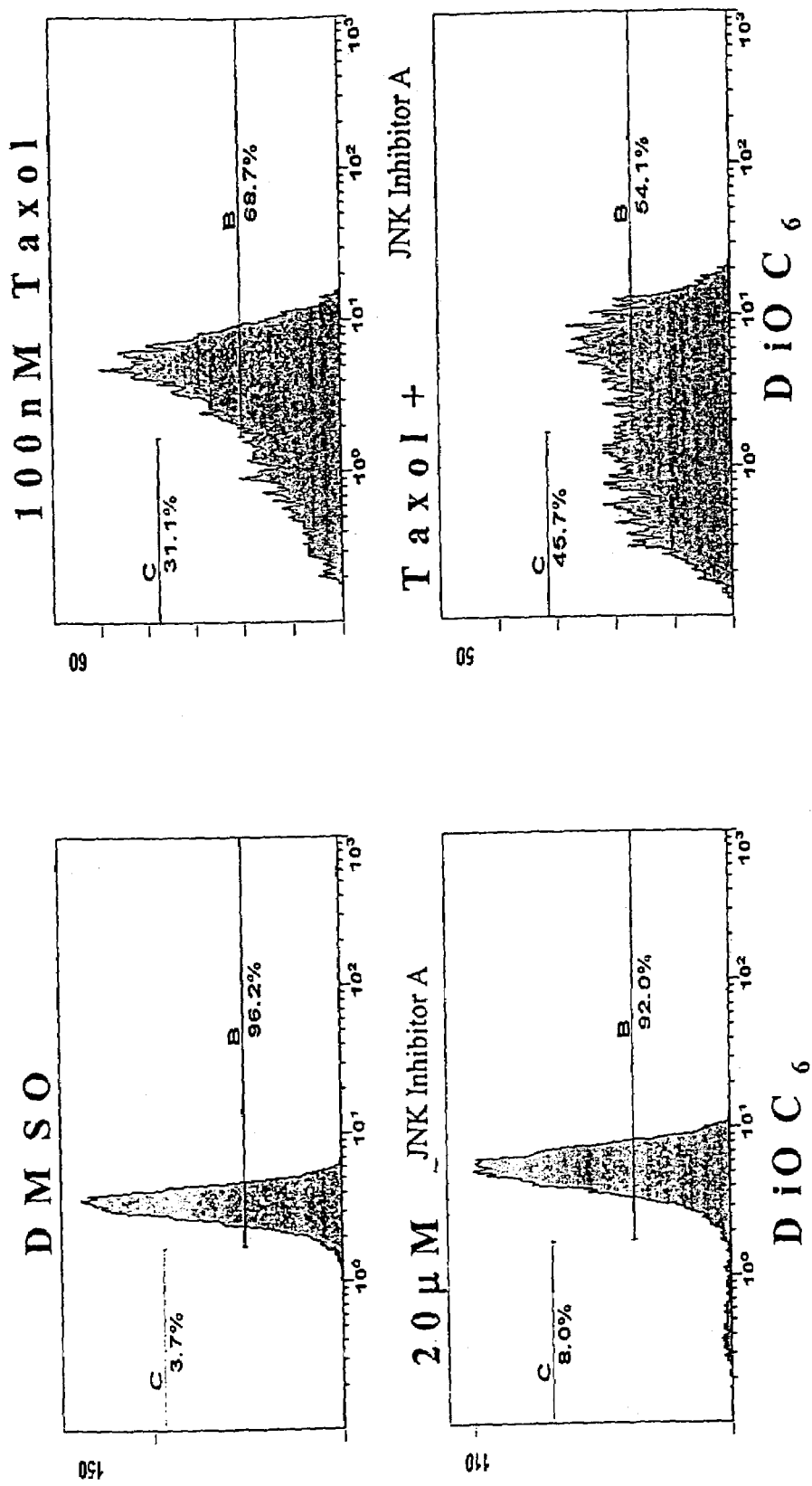

FIG. 3: FIG. 3 shows the effect of JNK inhibitor A (2H-Dibenzo(cd,g) indazol-6-one) in combination with a chemotherapeutic agent on the apoptosis of tumor cells.

Figure 4:
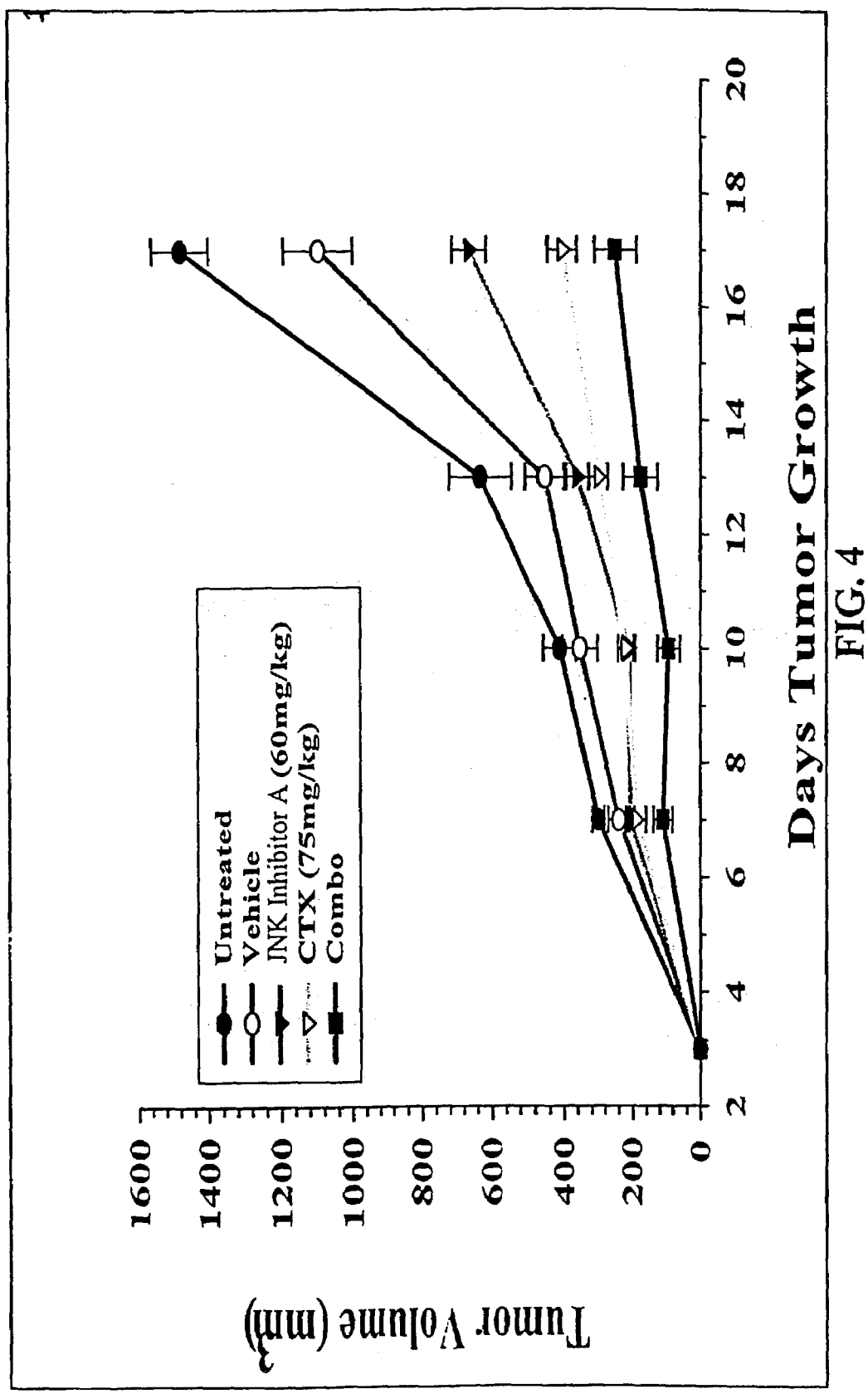

FIG. 4: FIG. 4 shows the effect of JNK inhibitor A (2H-Dibenzo(cd,g) indazol-6-one) in combination with a chemotherapeutic agent (CTX) on Lewis Lung Carcinoma proliferation.

Figure 5:
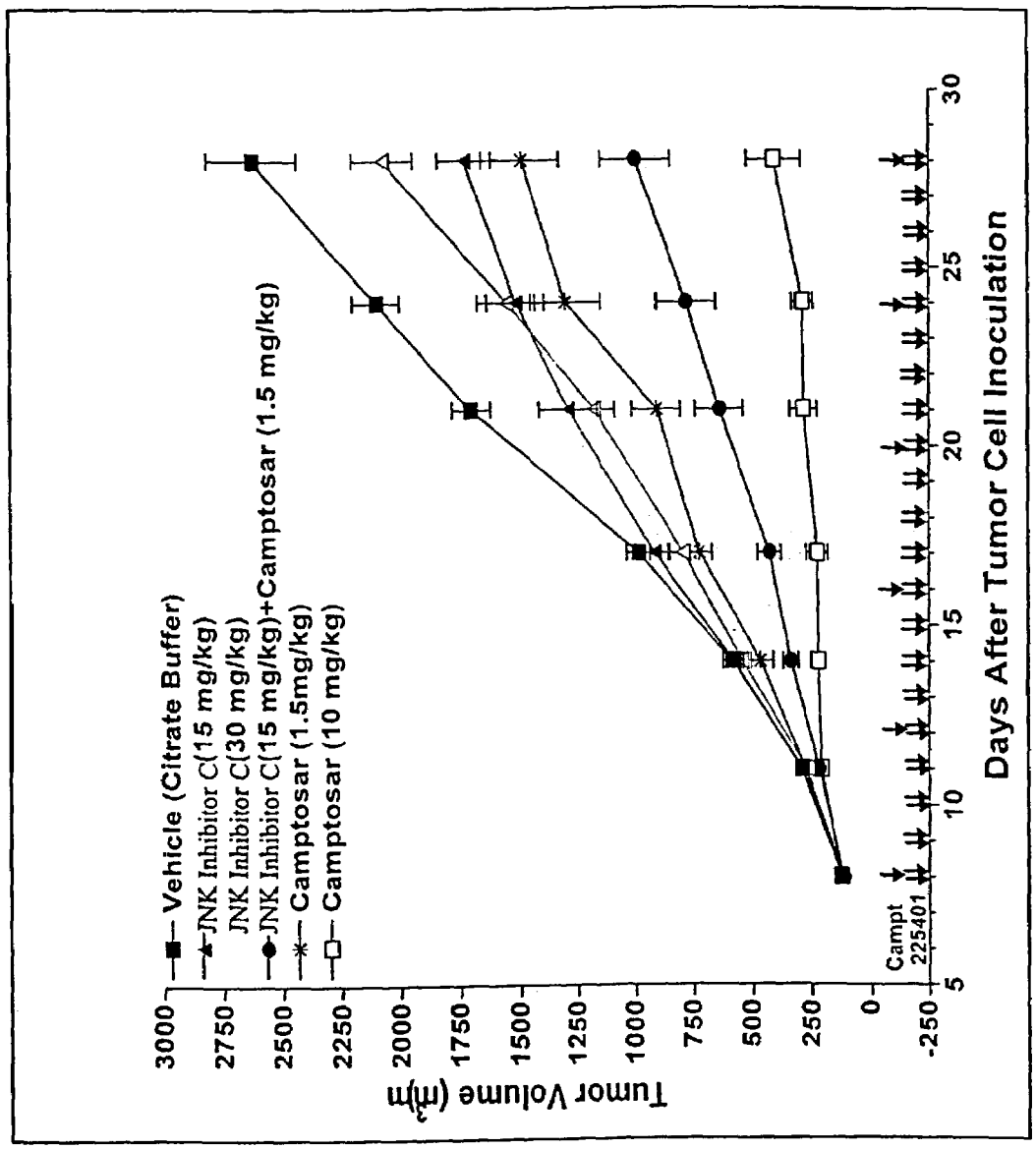

FIG. 5: FIG. 5 shows the effect of JNK inhibitor C (3-(4-(2-Piperidin-1-yl-ethoxy)-cyclohexa-1,5-dienyl)-5-(2H-(1,2,4)triazol-3-yl)-1H-indazole) in combination with a chemotherapeutic agent (camptosar) on human colorectal cancer cell (HCT-116) proliferation.

Figure 6:
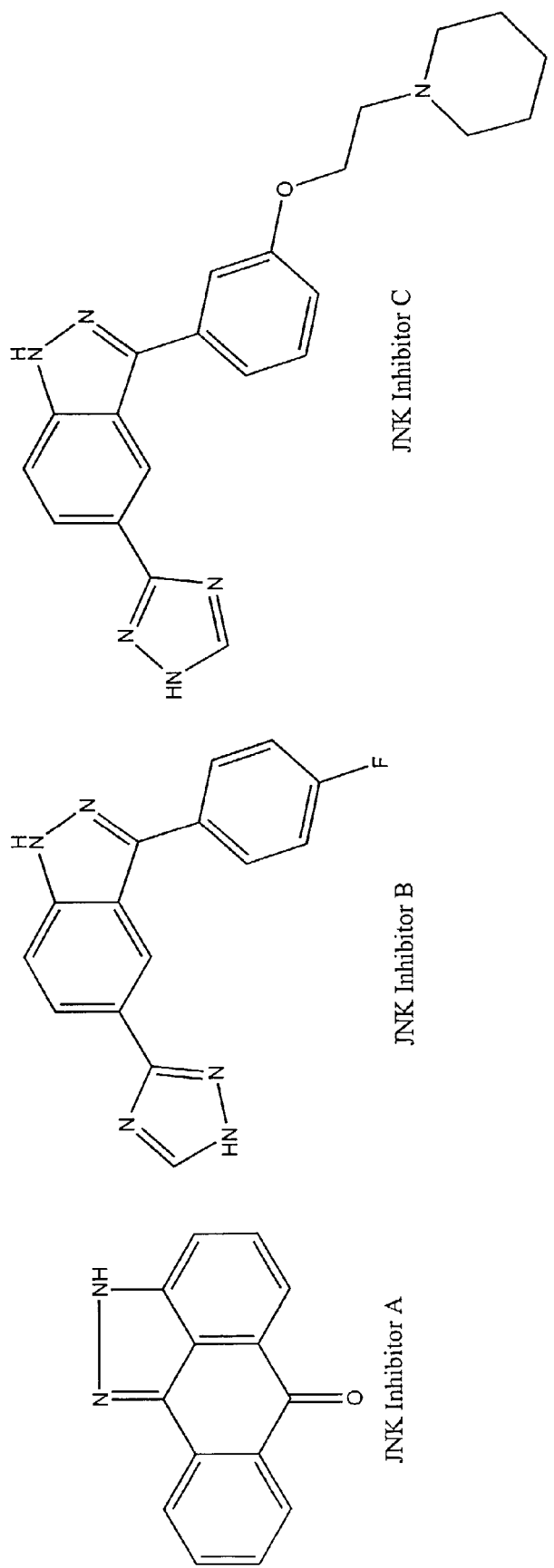

FIG. 6: FIG. 6 shows the structure of JNK inhibitors A, B and C.

3.2 DEFINITIONS

The terms used herein having the following meaning:

"Alkyl" means a saturated straight chain or branched non-cyclic hydrocarbon having from 1 to 10 carbon atoms. Representative saturated straight chain alkyls include -methyl, -ethyl, -n-propyl, -n-butyl, -n-pentyl, -n-hexyl, -n-heptyl, -n-octyl, -n-nonyl and -n-decyl; while saturated branched alkyls include -isopropyl, -sec-butyl, -isobutyl, -tert-butyl, -isopentyl, 2-methylbutyl, 3-methylbutyl, 2-methylpentyl, 3-methylpentyl, 4-methylpentyl, 2-methylhexyl, 3-methylhexyl, 4-methylhexyl, 5-methylhexyl, 2,3-dimethylbutyl, 2,3-dimethylpentyl, 2,4-dimethylpentyl, 2,3-dimethylhexyl, 2,4-dimethylhexyl, 2,5-dimethylhexyl, 2,2-dimethylpentyl, 2,2-dimethylhexyl, 3,3-dimtheylpentyl, 3,3-dimethylhexyl, 4,4-dimethylhexyl, 2-ethylpentyl, 3-ethylpentyl, 2-ethylhexyl, 3-ethylhexyl, 4-ethylhexyl, 2-methyl-2-ethylpentyl, 2-methyl-3-ethylpentyl, 2-methyl-4-ethylpentyl, 2-methyl-2-ethylhexyl, 2-methyl-3-ethylhexyl, 2-methyl-4-ethylhexyl, 2,2-diethylpentyl, 3,3-diethylhexyl, 2,2-diethylhexyl, 3,3-diethylhexyl and the like.

An "alkenyl group" means a straight chain or branched non-cyclic hydrocarbon having from 2 to 10 carbon atoms and including at least one carbon-carbon double bond. Representative straight chain and branched ($C_2$-$C_{10}$)alkenyls include -vinyl, -allyl, -1-butenyl, -2-butenyl, -isobutylenyl, -1-pentenyl, -2-pentenyl, -3-methyl-1-butenyl, -2-methyl-2-butenyl, -2,3-dimethyl-2-butenyl, -1-hexenyl, -2-hexenyl, -3-hexenyl, -1-heptenyl, -2-heptenyl, -3-heptenyl, -1-octenyl, -2-octenyl, -3-octenyl, -1-nonenyl, -2-nonenyl, -3-nonenyl, -1-decenyl, -2-decenyl, -3-decenyl and the like. An alkenyl group can be unsubstituted or substituted.

An "alkynyl group" means a straight chain or branched non-cyclic hydrocarbon having from 2 to 10 carbon atoms and including at lease one carbon-carbon triple bond. Representative straight chain and branched —($C_2$-$C_{10}$)alkynyls include -acetylenyl, -propynyl, -1-butynyl, -2-butynyl, -1-pentynyl, -2-pentynyl, -3-methyl-1-butynyl, -4-pentynyl, -1-hexynyl, -2-hexynyl, -5-hexynyl, -1-heptynyl, -2-heptynyl, -6-heptynyl, -1-octynyl, -2-octynyl, -7-octynyl, -1-nonynyl, -2-nonynyl, -8-nonynyl, -1-decynyl, -2-decynyl, -9-decynyl, and the like. An alkynyl group can be unsubstituted or substituted.

"Halogen" means fluorine, chlorine, bromine or iodine.

"Keto" means a carbonyl group (i.e., C=O).

"Acyloxy means an —OC(O)alkyl group, wherein alkyl is defined above, including —OC(O)$CH_3$, —OC(O)$CH_2CH_3$, —OC(O)($CH_2$)$_2CH_3$, —OC(O)($CH_2$)$_3CH_3$, —OC(O)($CH_2$)$_4CH_3$, —OC(O)($CH_2$)$_5CH_3$, and the like.

"Alkoxy" means —O-(alkyl), wherein alkyl is defined above, including —O$CH_3$, —O$CH_2CH_3$, —O($CH_2$)$_2CH_3$, —O($CH_2$)$_3CH_3$, —O($CH_2$)$_4CH_3$, —O($CH_2$)$_5CH_3$, and the like.

"Alkoxyalkoxy" means —O-(alkyl)-O-(alkyl), wherein each alkyl is independently an alkyl group defined above, including —O$CH_2$O$CH_3$, —O$CH_2CH_2$O$CH_3$, —O$CH_2CH_2$O$CH_2CH_3$, and the like.

"Alkoxycarbonyl" means —C(=O)O-(alkyl), wherein alkyl is defined above, including —C(=O)O—$CH_3$, —C(=O)O—$CH_2CH_3$, —C(=O)O—($CH_2$)$_2CH_3$, —C(=O)O—($CH_2$)$_3CH_3$, —C(=O)O—($CH_2$)$_4CH_3$, —C(=O)O—($CH_2$)$_5CH_3$, and the like.

"Alkoxycarbonylalkyl" means -(alkyl)-C(=O)O-(alkyl), wherein each alkyl is independently defined above, including —$CH_2$—C(=O)O—$CH_3$, —$CH_2$—C(=O)O—$CH_2CH_3$, —$CH_2$—C(=O)O—($CH_2$)$_2CH_3$, —$CH_2$—C(=O)O—($CH_2$)$_3CH_3$, —$CH_2$—C(=O)O—($CH_2$)$_4CH_3$, —$CH_2$—C(=O)O—($CH_2$)$_5CH_3$, and the like.

"Alkoxyalkyl" means -(alkyl)-O-(alkyl), wherein each alkyl is independently an alkyl group defined above, including —$CH_2$O$CH_3$, —$CH_2$O$CH_2CH_3$, —($CH_2$)$_2$O$CH_2CH_3$, —($CH_2$)$_2$O($CH_2$)$_2CH_3$, and the like.

"Aryl" means a carbocyclic aromatic group containing from 5 to 10 ring atoms. Representative examples include, but are not limited to, phenyl, tolyl, anthracenyl, fluorenyl, indenyl, azulenyl, pyridinyl and naphthyl, as well as benzo-fused carbocyclic moieties including 5,6,7,8-tetrahydronaphthyl. A carbocyclic aromatic group can be unsubstituted or substituted. In one embodiment, the carbocyclic aromatic group is a phenyl group.

"Aryloxy" means —O-aryl group, wherein aryl is as defined above. An aryloxy group can be unsubstituted or substituted. In one embodiment, the aryl ring of an aryloxy group is a phenyl group "Arylalkyl" means -(alkyl)-(aryl), wherein alkyl and aryl are as defined above, including —($CH_2$)phenyl, —($CH_2$)$_2$phenyl, —($CH_2$)$_3$phenyl, —CH(phenyl)$_2$, —CH(phenyl)$_3$, —($CH_2$)tolyl, —($CH_2$)anthracenyl, —($CH_2$)fluorenyl, —($CH_2$)indenyl, —($CH_2$)azulenyl, —($CH_2$)pyridinyl, —($CH_2$)naphthyl, and the like.

"Arylalkyloxy" means —O-(alkyl)-(aryl), wherein alkyl and aryl are defined above, including —O—($CH_2$)$_2$phenyl, —O—($CH_2$)$_3$phenyl, —O—CH(phenyl)$_2$, —O—CH(phenyl)$_3$, —O—($CH_2$)tolyl, —O—($CH_2$)anthracenyl, —O—($CH_2$)fluorenyl, —O—($CH_2$)indenyl, —O—($CH_2$)azulenyl, —O—($CH_2$)pyridinyl, —O—($CH_2$)naphthyl, and the like.

"Aryloxyalkyl" means -(alkyl)-O-(aryl), wherein alkyl and aryl are defined above, including —$CH_2$—O-(phenyl), —($CH_2$)$_2$—O-phenyl, —($CH_2$)$_3$—O-phenyl, —($CH_2$)—O-tolyl, —($CH_2$)—O-anthracenyl, —($CH_2$)—O-fluorenyl, —($CH_2$)—O-indenyl, —($CH_2$)—O-azulenyl, —($CH_2$)—O-pyridinyl, —($CH_2$)—O-naphthyl, and the like.

"Cycloalkyl" means a monocyclic or polycyclic saturated ring having carbon and hydrogen atoms and having no carbon-carbon multiple bonds. Examples of cycloalkyl groups include, but are not limited to, ($C_3$-$C_7$)cycloalkyl groups, including cyclopropyl, cyclobutyl, cyclopentyl, cyclohexyl, and cycloheptyl, and saturated cyclic and bicyclic terpenes. A cycloalkyl group can be unsubstituted or substituted. In one embodiment, the cycloalkyl group is a monocyclic ring or bicyclic ring.

"Cycloalkyloxy" means —O-(cycloalkyl), wherein cycloalkyl is defined above, including —O-cyclopropyl, —O-cyclobutyl, —O-cyclopentyl, —O-cyclohexyl, —O-cycloheptyl and the like.

"Cycloalkylalkyloxy" means —O-(alkyl)-(cycloalkyl), wherein cycloalkyl and alkyl are defined above, including —O—$CH_2$-cyclopropyl, —O—$(CH_2)_2$-cyclopropyl, —O—$(CH_2)_3$-cyclopropyl, —O—$(CH_2)_4$-cyclopropyl, O—$CH_2$-cyclobutyl, O—$CH_2$-cyclopentyl, O—$CH_2$-cyclohexyl, O—$CH_2$-cycloheptyl, and the like.

"Aminoalkoxy" means —O-(alkyl)-$NH_2$, wherein alkyl is defined above, such as —O—$CH_2$—$NH_2$, —O—$(CH_2)_2$—$NH_2$, —O—$(CH_2)_3$—$NH_2$, —O—$(CH_2)_4$—$NH_2$, —O—$(CH_2)_5$—$NH_2$, and the like.

"Mono-alkylamino" means —NH(alkyl), wherein alkyl is defined above, such as —$NHCH_3$, —$NHCH_2CH_3$, —NH$(CH_2)_2CH_3$, —NH$(CH_2)_3CH_3$, —NH$(CH_2)_4CH_3$, —NH$(CH_2)_5CH_3$, and the like.

"Di-alkylamino" means —N(alkyl)(alkyl), wherein each alkyl is independently an alkyl group defined above, including —$N(CH_3)_2$, —$N(CH_2CH_3)_2$, —$N((CH_2)_2CH_3)_2$, —$N(CH_3)(CH_2CH_3)$, and the like.

"Mono-alkylaminoalkoxy" means —O-(alkyl)-NH(alkyl), wherein each alkyl is independently an alkyl group defined above, including —O—$(CH_2)$—$NHCH_3$, —O—$(CH_2)$—$NHCH_2CH_3$, —O—$(CH_2)$—$NH(CH_2)_2CH_3$, —O—$(CH_2)$—$NH(CH_2)_3CH_3$, —O—$(CH_2)$—$NH(CH_2)_4CH_3$, —O—$(CH_2)$—$NH(CH_2)_5CH_3$, —O—$(CH_2)_2$—$NHCH_3$, and the like.

"Di-alkylaminoalkoxy" means —O-(alkyl)N(alkyl)(alkyl), wherein each alkyl is independently an alkyl group defined above, including —O—$(CH_2)$—$N(CH_3)_2$, —O—$(CH_2)$—$N(CH_2CH_3)_2$, —O—$(CH_2)$—$N(CH_2CH_3)_2$, —O—$(CH_2)$—N$((CH_2)_2CH_3)_2$, —O—$(CH_2)$—$N(CH_3)(CH_2CH_3)$, and the like.

"Arylamino" means —NH(aryl), wherein aryl is defined above, including —NH(phenyl), —NH(tolyl), —NH(anthracenyl), —NH(fluorenyl), —NH(indenyl), —NH(azulenyl), —NH(pyridinyl), —NH(naphthyl), and the like.

"Arylalkylamino" means —NH-(alkyl)-(aryl), wherein alkyl and aryl are defined above, including —NH—$CH_2$-(phenyl), —NH—$CH_2$-(tolyl), —NH—$CH_2$-(anthracenyl), —NH—$CH_2$-(fluorenyl), —NH—$CH_2$-(indenyl), —NH—$CH_2$-(azulenyl), —NH—$CH_2$-(pyridinyl), —NH—$CH_2$-(naphthyl), —NH—$(CH_2)_2$-(phenyl) and the like.

"Alkylamino" means mono-alkylamino or di-alkylamino as defined above.

"Cycloalkylamino" means —NH-(cycloalkyl), wherein cycloalkyl is as defined above, including —NH-cyclopropyl, —NH-cyclobutyl, —NH-cyclopentyl, —NH-cyclohexyl, —NH-cycloheptyl, and the like.

"Carboxyl" and "carboxy" mean —COOH.

"Cycloalkylalkylamino" means —NH-(alkyl)-(cycloalkyl), wherein alkyl and cycloalkyl are defined above, including —NH—$CH_2$-cyclopropyl, —NH—$CH_2$-cyclobutyl, —NH—$CH_2$-cyclopentyl, —NH—$CH_2$-cyclohexyl, —NH—$CH_2$-cycloheptyl, —NH—$(CH_2)_2$-cyclopropyl and the like.

"Aminoalkyl" means -(alkyl)-$NH_2$, wherein alkyl is defined above, including $CH_2$—$NH_2$, —$(CH_2)_2$—$NH_2$, —$(CH_2)_3$—$NH_2$, —$(CH_2)_4$—$NH_2$, —$(CH_2)_5$—$NH_2$ and the like.

"Mono-alkylaminoalkyl" means -(alkyl)-NH(alkyl), wherein each alkyl is independently an alkyl group defined above, including —$CH_2$—NH—$CH_3$, —$CH_2$—$NHCH_2CH_3$, —$CH_2$—$NH(CH_2)_2CH_3$, —$CH_2$—$NH(CH_2)_3CH_3$, —$CH_2$—$NH(CH_2)_4CH_3$, —$CH_2$—$NH(CH_2)_5CH_3$, —$(CH_2)_2$—NH—$CH_3$, and the like.

"Di-alkylaminoalkyl" means -(alkyl)-N(alkyl)(alkyl), wherein each alkyl is independently an alkyl group defined above, including —$CH_2$—$N(CH_3)_2$, —$CH_2$—$N(CH_2CH_3)_2$, —$CH_2$—$N((CH_2)_2CH_3)_2$, —$CH_2$—$N(CH_3)(CH_2CH_3)$, —$(CH_2)_2$—$N(CH_3)_2$, and the like.

"Heteroaryl" means an aromatic heterocycle ring of 5- to 10 members and having at least one heteroatom selected from nitrogen, oxygen and sulfur, and containing at least 1 carbon atom, including both mono- and bicyclic ring systems. Representative heteroaryls are triazolyl, tetrazolyl, oxadiazolyl, pyridyl, furyl, benzofuranyl, thiophenyl, benzothiophenyl, quinolinyl, pyrrolyl, indolyl, oxazolyl, benzoxazolyl, imidazolyl, benzimidazolyl, thiazolyl, benzothiazolyl, isoxazolyl, pyrazolyl, isothiazolyl, pyridazinyl, pyrimidinyl, pyrazinyl, triazinyl, cinnolinyl, phthalazinyl, quinazolinyl, pyrimidyl, oxetanyl, azepinyl, piperazinyl, morpholinyl, dioxanyl, thietanyl and oxazolyl.

"Heteroarylalkyl" means -(alkyl)-(heteroaryl), wherein alkyl and heteroaryl are defined above, including —$CH_2$-triazolyl, —$CH_2$-tetrazolyl, —$CH_2$-oxadiazolyl, —$CH_2$-pyridyl, —$CH_2$-furyl, —$CH_2$-benzofuranyl, —$CH_2$-thiophenyl, —$CH_2$-benzothiophenyl, —$CH_2$-quinolinyl, —$CH_2$-pyrrolyl, —$CH_2$-indolyl, —$CH_2$-oxazolyl, —$CH_2$-benzoxazolyl, —$CH_2$-imidazolyl, —$CH_2$-benzimidazolyl, —$CH_2$-thiazolyl, —$CH_2$-benzothiazolyl, —$CH_2$-isoxazolyl, —$CH_2$-pyrazolyl, —$CH_2$-isothiazolyl, —$CH_2$-pyridazinyl, —$CH_2$-pyrimidinyl, —$CH_2$-pyrazinyl, —$CH_2$-triazinyl, —$CH_2$-cinnolinyl, —$CH_2$-phthalazinyl, —$CH_2$-quinazolinyl, —$CH_2$-pyrimidyl, —$CH_2$-oxetanyl, —$CH_2$-azepinyl, —$CH_2$-piperazinyl, —$CH_2$-morpholinyl, —$CH_2$-dioxanyl, —$CH_2$-thietanyl, —$CH_2$-oxazolyl, —$(CH_2)_2$-triazolyl, and the like.

"Heterocycle" means a 5- to 7-membered monocyclic, or 7- to 10-membered bicyclic, heterocyclic ring which is either saturated, unsaturated, and which contains from 1 to 4 heteroatoms independently selected from nitrogen, oxygen and sulfur, and wherein the nitrogen and sulfur heteroatoms can be optionally oxidized, and the nitrogen heteroatom can be optionally quaternized, including bicyclic rings in which any of the above heterocycles are fused to a benzene ring. The heterocycle can be attached via any heteroatom or carbon atom. Heterocycles include heteroaryls as defined above. Representative heterocycles include morpholinyl, pyrrolidinonyl, pyrrolidinyl, piperidinyl, hydantoinyl, valerolactamyl, oxiranyl, oxetanyl, tetrahydrofuranyl, tetrahydropyranyl, tetrahydropyridinyl, tetrahydroprimidinyl, tetrahydrothiophenyl, tetrahydrothiopyranyl, tetrahydropyrimidinyl, tetrahydrothiophenyl, tetrahydrothiopyranyl, and the like.

"Heterocycle fused to phenyl" means a heterocycle, wherein heterocycle is defined as above, that is attached to a phenyl ring at two adjacent carbon atoms of the phenyl ring.

"Heterocycloalkyl" means -(alkyl)-(heterocycle), wherein alkyl and heterocycle are defined above, including —$CH_2$-morpholinyl, —$CH_2$-pyrrolidinonyl, —$CH_2$-pyrrolidinyl, —$CH_2$-piperidinyl, —$CH_2$-hydantoinyl, —$CH_2$-valerolactamyl, —$CH_2$-oxiranyl, —$CH_2$-oxetanyl, —$CH_2$-tetrahydrofuranyl, —$CH_2$-tetrahydropyranyl, —$CH_2$-tetrahydropyridinyl, —$CH_2$-tetrahydroprimidinyl, —$CH_2$-tetrahydrothiophenyl, —$CH_2$-tetrahydrothiopyranyl, —$CH_2$-tetrahydropyrimidinyl, —$CH_2$-tetrahydrothiophenyl, —$CH_2$-tetrahydrothiopyranyl, and the like.

The term "substituted" as used herein means any of the above groups (i.e., aryl, arylalkyl, heterocycle and heterocycloalkyl) wherein at least one hydrogen atom of the moiety being substituted is replaced with a substituent. In one embodiment, each carbon atom of the group being substituted is substituted with no more that two substituents. In another embodiment, each carbon atom of the group being substituted is substituted with no more than one substituent. In the case of a keto substituent, two hydrogen atoms are replaced with an oxygen which is attached to the carbon via a double bond. Substituents include halogen, hydroxyl, alkyl, haloalkyl, mono- or di-substituted aminoalkyl, alkyloxyalkyl, aryl, arylalkyl, heterocycle, heterocycloalkyl, —$NR_aR_b$, —$NR_aC(=O)R_b$, —$NR_aC(=O)NR_aR_b$, —$NR_aC(=O)OR_b$—$NR_aSO_2R_b$, —$OR_a$, —$C(=O)R_a$ $C(=O)OR_a$—$C(=O)NR_aR_b$, —$OC(=O)R_a$, —$OC(=O)OR_a$, —$OC(=O)NR_aR_b$, —$NR_aSO_2R_b$, or a radical of the formula —Y—Z—$R_a$ where Y is alkanediyl, or a direct bond, Z is —O—, —S—, —N($R_b$)—, —C(=O)—, —C(=O)O—, —OC(=O)—, —N($R_b$)C(=O)—, —C(=O)N($R_b$)— or a direct bond, wherein $R_a$ and $R_b$ are the same or different and independently hydrogen, amino, alkyl, haloalkyl, aryl, arylalkyl, heterocycle, or heterocylealkyl, or wherein $R_a$ and $R_b$ taken together with the nitrogen atom to which they are attached form a heterocycle.

"Haloalkyl" means alkyl, wherein alkyl is defined as above, having one or more hydrogen atoms replaced with halogen, wherein halogen is as defined above, including —$CF_3$, —$CHF_2$, —$CH_2F$, —$CBr_3$, —$CHBr_2$, —$CH_2Br$, —$CCl_3$, —$CHCl_2$, —$CH_2Cl$, —$CI_3$, —$CHI_2$, —$CH_2I$, —$CH_2$—$CF_3$, —$CH_2$—$CHF_2$, —$CH_2$—$CH_2F$, —$CH_2$—$CBr_3$, —$CH_2$—$CHBr_2$, —$CH_2$—$CH_2Br$, —$CH_2$—$CCl_3$, —$CH_2$—$CHCl_2$, —$CH_2$—$CH_2Cl$, —$CH_2$—$CI_3$, —$CH_2$—$CHI_2$, —$CH_2$—$CH_2I$, and the like.

"Hydroxyalkyl" means alkyl, wherein alkyl is as defined above, having one or more hydrogen atoms replaced with hydroxy, including —$CH_2OH$, —$CH_2CH_2OH$, —$(CH_2)_2CH_2OH$, —$(CH_2)_3CH_2OH$, —$(CH_2)_4CH_2OH$, —$(CH_2)_5CH_2OH$, —CH(OH)—$CH_3$, —$CH_2CH(OH)CH_3$, and the like.

"Hydroxy" means —OH.

"Sulfonyl" means —$SO_3H$;

"Sulfonylalkyl" means —$SO_2$-(alkyl), wherein alkyl is defined above, including —$SO_2$—$CH_3$, —$SO_2$—$CH_2CH_3$, —$SO_2$—$(CH_2)_2CH_3$, —$SO_2$—$(CH_2)_3CH_3$, —$SO_2$—$(CH_2)_4CH_3$, —$SO_2$—$(CH_2)_5CH_3$, and the like.

"Sulfinylalkyl" means —SO-(alkyl), wherein alkyl is defined above, including —SO—$CH_3$, —SO—$CH_2CH_3$, —SO—$(CH_2)_2CH_3$, —SO—$(CH_2)_3CH_3$, —$SO_2$—$(CH_2)_4CH_3$, —$SO_2$—$(CH_2)_5CH_3$, and the like.

"Thioalkyl" means —S-(alkyl), wherein alkyl is defined above, including —S—$CH_3$, —S—$CH_2CH_3$, —S—$(CH_2)_2CH_3$, —S—$(CH_2)_3CH_3$, —S—$(CH_2)_4CH_3$, —S—$(CH_2)_5CH_3$, and the like.

An "effective amount" when used in connection with a JNK Inhibitor is an amount of the JNK Inhibitor that is useful for treating or preventing a cardiovascular or renal disease.

An "effective amount" when used in connection with another active agent is an amount of the other active agent that is useful for providing the agent's therapeutic or prophylactic effect.

As used herein, the term "pharmaceutically acceptable salt(s)" refer to salts prepared from pharmaceutically acceptable non-toxic acids or bases including inorganic acids and bases and organic acids and bases. Suitable pharmaceutically acceptable base addition salts for the compound of the present invention include, but are not limited to metallic salts made from aluminum, calcium, lithium, magnesium, potassium, sodium and zinc or organic salts made from lysine, N,N'-dibenzylethylenediamine, chloroprocaine, choline, diethanolamine, ethylenediamine, meglumine (N-methylglucamine) and procaine. Suitable non-toxic acids include, but are not limited to, inorganic and organic acids such as acetic, alginic, anthranilic, benzenesulfonic, benzoic, camphorsulfonic, citric, ethenesulfonic, formic, fumaric, furoic, galacturonic, gluconic, glucuronic, glutamic, glycolic, hydrobromic, hydrochloric, isethionic, lactic, maleic, malic, mandelic, methanesulfonic, mucic, nitric, pamoic, pantothenic, phenylacetic, phosphoric, propionic, salicylic, stearic, succinic, sulfanilic, sulfuric, tartaric acid, and p-toluenesulfonic acid. Specific non-toxic acids include hydrochloric, hydrobromic, phosphoric, sulfuric, and methanesulfonic acids. Examples of specific salts thus include hydrochloride and mesylate salts. Others are well-known in the art, see for example, *Remington's Pharmaceutical Sciences*, 18th eds., Mack Publishing, Easton Pa. (1990) or *Remington: The Science and Practice of Pharmacy*, 19th eds., Mack Publishing, Easton Pa. (1995).

As used herein and unless otherwise indicated, the term "prodrug" means a a compound that can hydrolyze, oxidize, or otherwise react under biological conditions (in vitro or in vivo) to provide a JNK Inhibitor. Examples of prodrugs include, but are not limited to, biohydrolyzable amides, biohydrolyzable esters, biohydrolyzable carbamates, biohydrolyzable carbonates, biohydrolyzable ureides, and biohydrolyzable phosphate analogues. In one embodiment, prodrugs are the lower alkyl esters of a carboxylic acid group of a JNK Inhibitor. The carboxylate esters are conveniently formed by esterification. Prodrugs can typically be prepared using well-known methods, such as those described by *Burger's Medicinal Chemistry and Drug Discovery* 6th ed. (Donald J. Abraham ed., 2001, Wiley) and *Design and Application of Prodrugs* (H. Bundgaard ed., 1985, Harwood Academic Publishers Gmfh).

Various JNK Inhibitors can contain one or more chiral centers and can exist as racemic mixtures of enantiomers or mixtures of diastereomers. This invention encompasses the use of enantiomers, as well as the use of mixtures of those forms. For example, enantiomers or racemates of a JNK Inhibitor, or mixtures thereof, can be used in the methods of the Invention.

The phrase "modulation of JNK" or "by modulating JNK" means the inhibition or activation, preferably the inhibition, of a protein known as Jun N-terminal kinase (JNK) and all isoforms thereof expressed by JNK 1, JNK 2, and JNK 3 genes (Hibi M., Lin A., Smeal T., Minden A., Karin M. *Genes Dev*. 7:2135-2148, 1993; Mohit A. A., Martin M. H., and Miller C. A. *Neuron* 14:67-78, 1995; Gupta, S., Barrett, T., Whitmarsh, A. J., Cavanagh, J., Sluss, H. K., Derijard, B. and Davis, R. J. *The EMBO J*. 15:2760-2770, 1996). The modulation of JNK can be achieved on the mRNA level, protein level and kinase activity level.

"JNK" means a protein and all isoforms thereof expressed by JNK 1, JNK 2, and JNK 3 genes (Gupta, S., Barrett, T., Whitmarsh, A. J., Cavanagh, J., Sluss, H. K., Derijard, B. and Davis, R. J. *The EMBO J*. 15:2760-2770, 1996).

"JNK inhibitor" or "inhibitors of JNK" means any molecule that blocks, reduces or retards the phosphorylation of c-Jun or other substrates by JNK or reduces the amount of JNK present in the cell. Inhibition may be either direct or indirect, preferably inhibition is direct. Inhibitors of JNK include, but are not limited to, small organic molecules (preferable with a molecular weight of less than 1000) which are not peptides, proteins, nucleic acids, polypeptides or oligonucleotides; or antibodies or a fragment thereof that immunospecifically binds to JNK or another component of the JNK pathway. In certain embodiments, inhibitors of JNK or another component of the JNK pathway, can inhibit either upstream or downstream. In one embodiment, JNK inhibitor means a compound capable of inhibiting the activity of JNK in vitro or in vivo. The JNK inhibitor can be in the form of a or a pharmaceutically acceptable salt, free base, solvate, hydrate, stereoisomer, clathrate or prodrug thereof. Such inhibitory activity can be determined by an assay or animal model well-known in the art. In one embodiment, the JNK inhibitor is a compound of structure (I)-(XX).

"JNK pathway" means any biological molecule which has a direct or indirect effect on the activity of JNK.

"Direct inhibition" means that the JNK inhibitor directly interacts with JNK.

"Indirect inhibition" means that the JNK inhibitor blocks, reduces or retards JNK activity by interacting with a component of the JNK pathway other than JNK.

As used herein, a "therapeutically effective amount" refers to that amount of the therapeutic agent sufficient to destroy, modify, control or remove primary, regional or metastatic cancer tissue. A therapeutically effective amount may refer to the amount of therapeutic agent sufficient to delay or minimize the spread of cancer. A therapeutically effective amount may also refer to the amount of the therapeutic agent that provides a therapeutic benefit in the treatment or management of cancer. Further, a therapeutically effective amount with respect to a therapeutic agent of the invention means that amount of therapeutic agent alone, or in combination with other therapies, that provides a therapeutic benefit in the treatment or management of cancer, including the amelioration of symptoms associated with the disease being treated. Used in connection with an amount of an inhibitor of JNK, the term can encompass an amount that improves overall therapy, reduces or avoids unwanted effects, or enhances the therapeutic efficacy of or synergizes with another therapeutic agent.

As used herein, a "prophylactically effective amount" refers to that amount of the prophylactic agent sufficient to result in the prevention of the recurrence or spread of cancer. A prophylactically effective amount may refer to the amount of prophylactic agent sufficient to prevent the recurrence or spread of cancer or the occurrence of cancer or metastasis in a patient, including, but not limited to, those predisposed to cancer or previously exposed to carcinogens. A prophylactically effective amount may also refer to the amount of the prophylactic agent that provides a prophylactic benefit in the prevention of cancer. Further, a prophylactically effective amount with respect to a prophylactic agent of the invention means that amount of prophylactic agent alone, or in combination with other agents, that provides a prophylactic benefit in the prevention of cancer. Used in connection with an amount of an inhibitor of JNK, the term can encompass an amount that improves overall prophylaxis or enhances the prophylactic efficacy of or synergizes with another prophylactic or therapeutic agent.

As used herein, the terms "therapies" and "therapy" can refer to any protocol(s), method(s) and or agent(s) that can be used in the prevention, treatment, or management of cancer. In certain embodiments, the terms "therapy" and "therapies" refer to cancer chemotherapy, radiation therapy, hormonal therapy, biological therapy, and/or other therapies useful for the treatment of cancer known to an oncologist skilled in the art.

As used herein, a "therapeutic protocol" refers to a regimen of timing and dosing of one or more therapeutic agents.

As used herein, a "prophylactic protocol" refers to a regimen of timing and dosing of one or more prophylactic agents.

A used herein, a "protocol" includes dosing schedules and dosing regimens. The protocols herein are methods of use.

As used herein, "in combination" refers to the use of more than one prophylactic and/or therapeutic agents against a disease or disorder.

As used herein, the phrase "non-responsive/refractory" is used to describe patients treated with currently available cancer therapies such as chemotherapy, radiation therapy, surgery, hormonal therapy and/or biological therapy/immunotherapy wherein the therapy is not clinically adequate to treat the patients such that these patients need additional effective therapy, e.g., remain unsusceptible to therapy. The phrase can also describe patients who respond to therapy yet suffer from side effects, relapse, develop resistance, etc. In various embodiments, "non-responsive/refractory" means that at least some significant portion of the cancer cells are not killed or their cell division arrested. The determination of whether the cancer cells are "non-responsive/refractory" can be made either in vivo or in vitro by any method known in the art for assaying the effectiveness of treatment on cancer cells, using the art-accepted meanings of "refractory" in such a context. In various embodiments, a cancer is "non-responsive/refractory" where the number of cancer cells has not been significantly reduced, or has increased.

As used herein, the phrase "low tolerance" refers to a state in which the patient suffers from side effects from treatment so that the patient does not benefit from and/or will not continue therapy because of the adverse effects.

As used herein, the term "patient" means an animal (e.g., cow, horse, sheep, pig, chicken, turkey, quail, cat, dog, mouse, rat, rabbit or guinea pig), in one embodiment a mammal such as a non-primate and a primate (e.g., monkey, baboon, chimpanzee and human), and in another embodiment a human. In certain embodiments, the patient is an infant, child, adolescent or adult.

As used herein, the term "adjunctive" is used interchangeably with "in combination" or "combinatorial." Such terms are also used where two or more therapeutic or prophylactic agents affect the treatment or prevention of the same disease.

As used herein, the term "potentiate" refers to an improvement in the efficacy of a therapeutic agent at its common or approved dose.

As used herein, the phrase "side effects" encompasses unwanted and adverse effects of a prophylactic or therapeutic agent. Adverse effects are always unwanted, but unwanted effects are not necessarily adverse. An adverse effect from a prophylactic or therapeutic agent might be harmful or uncomfortable or risky. Side effects from chemotherapy include, but are not limited to, gastrointestinal toxicity such as, but not limited to, early and late-forming diarrhea and flatulence; nausea; vomiting; anorexia; leukopenia; anemia; neutropenia; asthenia; abdominal cramping; fever; pain; loss of body weight; dehydration; alopecia; dyspnea; insomnia; dizziness, mucositis, xerostomia, and kidney or renal failure, as well as constipation, nerve and muscle effects, temporary or permanent damage to kidneys and bladder, flu-like symptoms, fluid retention, and temporary or permanent infertility. Side effects from radiation therapy include but are not limited to fatigue, dry mouth, and loss of appetite. Other side effects include gastrointestinal toxicity such as, but not limited to, early and late-forming diarrhea and flatulence; nausea; vomiting; anorexia; leukopenia; anemia; neutropenia; asthenia; abdominal cramping; fever; pain; loss of body weight; dehydration; alopecia; dyspnea; insomnia; dizziness, mucositis, xerostomia, and kidney failure. Side effects from biological therapies/immunotherapies include but are not limited to rashes or swellings at the site of administration, flu-like symptoms such as fever, chills and fatigue, digestive tract problems and allergic reactions. Side effects from hormonal therapies include but are not limited to nausea, fertility problems, depression, loss of appetite, eye problems, headache, and weight fluctuation. Additional undesired effects typically experienced by patients are numerous and known in the art. Many are described in the *Physicians' Desk Reference* ($56^{th}$ ed., 2002).

As used herein, the terms "manage", "managing" and "management" refer to the beneficial effects that a patient derives from a prophylactic or therapeutic agent, which does not result in a cure of the disease. In certain embodiments, a patient is administered one or more prophylactic or therapeutic agents to "manage" a disease so as to prevent the progression or worsening of the disease.

As used herein, the terms "prevent", "preventing" and "prevention" refer to the prevention of the recurrence, spread or onset of primary cancer or metastasis in a patient resulting from the administration of a prophylactic or therapeutic agent.

As used herein, the terms "treat", "treating" and "treatment" refer to the eradication, removal, modification, or control of primary, regional, or metastatic cancer tissue that results from the administration of one or more prophylactic or therapeutic agents. In certain embodiments, such terms refer to the minimizing or delay of the spread of cancer resulting from the administration of one or more prophylactic or therapeutic agents to a patient with such a disease.

4. DETAILED DESCRIPTION OF THE INVENTION

As mentioned above, the present invention is directed to methods useful for treating, preventing or managing cancer by administering to a patient in need thereof one or more JNK inhibitors in combination with one or more anti-cancer agents and/or radiation therapy. Representative JNK inhibitors of the present invention include, but are not limited to, indazoles, anilinopyrimidine, isothiazoloanthrones, isoxazoloanthrones, isoindolanthrones, pyrazoloanthrones and derivatives thereof.

In certain embodiments, inhibitors of JNK decrease the activity of JNK. In other embodiments, inhibitors of JNK decrease the amount of JNK present in the cell. In other embodiments, inhibitors of JNK decrease the amount of JNK mRNA, or mRNA of another component of the JNK pathway, in the cell.

In one embodiment, the inhibitor of JNK is a small organic molecule capable of inhibiting JNK activity or another component of the JNK pathway. In another embodiment, the inhibitor of JNK is an antibody or a fragment thereof that immunospecifically binds to JNK or another component of the JNK pathway. In another embodiment, the JNK inhibitor is triplex DNA that inhibits DNA transcription or replication of JNK or of another component of the JNK pathway. In another embodiment, JNK or another component of the JNK pathway, is inhibited through viral therapy. In another embodiment, the inhibitor of JNK, or another component of the JNK pathway, is dominant-negative JNK (DN-JNK). In certain embodiments, inhibitors of JNK can inhibit either upstream or downstream of JNK.

In a preferred embodiment, the invention encompasses the use of a JNK inhibitor in combination with a chemotherapeutic agent such as an apoptosis inducing agent to treat, prevent or manage cancer. In a further embodiment, the chemotherapeutic includes, but is not limited to, paclitaxel, irinotecan, camptothecin, cyclophosphamide, 5-fluorouracil, cisplatinum, carboplatin, methotrexate, trimetrexate, Erbitux™, thalidomide, any SelCid™ or IMiD™ compound, in particular Actimid™ or Revimid™.

The present invention is based, in part, on the recognition that inhibitors of JNK potentiate and synergize with, enhance the effectiveness of, improve the tolerance of, and/or reduce side effects caused by, other cancer therapies, including current standard and experimental chemotherapies, hormonal therapies, biological therapies/immunotherapies, bone marrow transplants, stem cell replacement therapies and radiation therapies. Thus, the invention encompasses treatment regimens or protocols that provide better therapeutic profiles than current single agent therapies or current combination therapy regimens. Encompassed by the invention are combination therapies that have additive potency or an additive therapeutic effect. The invention also encompasses synergistic combinations where the therapeutic ratio is greater than additive. Preferably, such combinations also reduce or avoid unwanted or adverse effects. In certain embodiments, the combination therapies encompassed by the invention provide an improved overall therapy relative to administration of either an inhibitors of JNK or any other cancer therapy alone. Given the invention, in certain embodiments, doses of existing or experimental cancer therapies can be reduced or administered less frequently which increases patient compliance, improves therapy and reduces unwanted or adverse effects. In one embodiment, the cancer is resistant to cancer treatment, such as chemotherapy or radiation therapy.

Accordingly, the present invention relates to pharmaceutical compositions and prophylactic and therapeutic regimens designed to prevent, treat, or manage cancer in a patient comprising administering one or more inhibitors of JNK in combination with one or more other cancer therapies other than the administration of a JNK inhibitor. In particular, the present invention provides methods of preventing, treating, or managing cancer in a patient comprising administering to said patient a therapeutically or prophylactically effective of one or more inhibitors of JNK in combination with the administration of a therapeutically or prophylactically effective amount of one or more chemotherapies, hormonal therapies, biological therapies/immunotherapies, bone marrow transplants, stem cell replacement therapies and radiation therapies other than the administration of a JNK inhibitor. It is also contemplated that such methods can include the administration of one or more JNK inhibitors in combination with surgery, alone or in combination with the administration of one or more chemotherapies, hormonal therapies, biological therapies/immunotherapies, bone marrow transplants, stem cell replacement therapies and radiation therapies other than the administration of a JNK inhibitor. In certain embodiments, the administration of inhibitors of JNK and the other cancer therapies is a therapeutic or prophylactic regimen or protocol. Such methods and regimens can encompass concurrent, sequential or alternating/cyclic administration of the inhibitors of JNK with one or more other cancer therapies.

In one embodiment, the inhibitor of JNK is administered with another cancer therapy that works by the same mechanism as the inhibitor of JNK. In another embodiment, an inhibitor of JNK is administered with another cancer therapy that works by a different mechanism than the inhibitor of JNK. By example and not by limitation, the cancer therapy can be apoptosis inducing, cytotoxic, antimitotic, anti-angiogenic, a modulator of TNF-alpha, tubulin stabilizing, microtubule formation inhibiting, topoisomerase active, antimetabolite, or DNA interactive agents. In other embodiments, the cancer therapy administered with an inhibitor of JNK is gene based. In other embodiments, the therapy is another antibody that is not an inhibitor of JNK such as Erbitux™.

In other embodiments, the invention encompasses the use of anti-cancer vaccines; or antibodies that immunoreact with Ecr, the RGD-directed adhesion receptor found on the surface of both endothelial and melanoma cells with one or more JNK inhibitors. Similarly, the JNK inhibitor can be used with antibodies which are useful for inhibiting the ability of cells that contain the adhesion receptor to adhere to a subendothelial matrix composed of vitronectin, fibrinogen or von Willegrand factor. Accordingly, the invention encompasses the use of JNK inhibitors with agents that are useful for inhibition of angiogenesis or inhibition of other functions including, but not limited to, cell proliferation, cell attachment, cell migration, granulation tissue development, and/or inflammation.

The methods and compositions of the invention are useful not only in untreated patients but are also useful in the treatment of patients partially or completely refractory to current standard and experimental cancer therapies, including, but not limited to, chemotherapies, hormonal therapies, biological therapies/immunotherapies, bone marrow transplants, stem cell replacement therapies and radiation therapies, and/or surgery. In one embodiment, the methods and compositions of the invention are useful in the treatment of patients with cancer(s) which is refractory against current chemotherapeutic agents. In another embodiment, the methods and compositions of the invention are useful in the treatment of patients with cancer(s) which is refractory against current multidrug therapies. In another embodiment, the methods and compositions of the invention are useful in the treatment of patients with cancer(s) which is refractory against tamoxifen. In a preferred embodiment, the invention provides therapeutic and prophylactic methods for the treatment or prevention of cancer that has been shown to be or may be refractory or non-responsive to therapies other than those comprising administration of JNK inhibitors. In another preferred embodiment, the invention provides therapeutic and prophylactic methods for the treatment or prevention of cancer that has been shown to be or may be refractory or non-responsive to therapies comprising administration of JNK inhibitors.

Further, the methods of the invention permit the treatment of cancer using lower and/or less frequent doses of chemotherapies, hormonal therapies, biological therapies/immunotherapies, bone marrow transplants, stem cell replacement therapies and radiation therapies to reduce the incidence of unwanted or adverse effects caused by administration of current/conventional agents while maintaining or enhancing the efficacy of treatment. In other embodiments of the invention, lower and/or less frequent doses of JNK inhibitors can be used for the treatment and/or prevention of cancer.

In certain embodiments, the invention provides prophylactic and therapeutic regimen or protocols comprising the administration of an inhibitor of JNK in combination with one or more chemotherapies, hormonal therapies, biological therapies/immunotherapies, bone marrow transplants, stem cell replacement therapies and radiation therapies other than the administration of a JNK inhibitor.

It is contemplated that the methods of treatment also include surgery in combination with the administration of an inhibitor of JNK in combination with one or more chemotherapies, hormonal therapies, biological therapies/immunotherapies, bone marrow transplants, stem cell replacement therapies and radiation therapies other than the administration of a JNK inhibitor.

In other embodiments, the invention provides prophylactic and therapeutic protocols comprising the administration of an inhibitor of JNK in combination with one or more hormonal therapies alone or, optionally, in combination with chemotherapies, hormonal therapies, biological therapies/immunotherapies, bone marrow transplants, stem cell replacement therapies and radiation therapies other than the administration of a JNK inhibitor.

In other embodiments, the invention provides prophylactic and therapeutic protocols comprising the administration of an inhibitor of JNK in combination with one or more biological therapies/immunotherapies alone or, optionally, in combination with chemotherapies, hormonal therapies, biological therapies/immunotherapies, bone marrow transplants, stem cell replacement therapies and radiation therapies other than the administration of a JNK inhibitor.

In yet other embodiments, the invention provides prophylactic and therapeutic protocols comprising the administration of a JNK inhibitor in combination with one or more radiation therapies alone or, optionally, in combination with chemotherapies, hormonal therapies, bone marrow transplants, stem cell replacement therapies, and/or biological therapies/immunotherapies other than the administration of a JNK inhibitor.

The present invention also contemplates methods of treatment comprising the administration of a JNK inhibitor in combination with surgery alone.

In a specific embodiment, the invention provides prophylactic and therapeutic protocols comprising the administration of a JNK inhibitor in combination with one or more cancer chemotherapeutic agents, such as but not limited to: doxorubicin, epirubicin, cyclophosphamide, 5-fluorouracil, taxanes such as docetaxel and paclitaxel, leucovorin, levamisole, irinotecan, estramustine, etoposide, vinblastine, dacarbazine, nitrosoureas such as carmustine and lomustine, vinca alkaloids, platinum compounds, cisplatin, mitomycin, vinorelbine, gemcitabine, carboplatin, hexamethylmelamine, topotecan, Erbitux™, thalidomide, any SelCid™ or IMiD™ compounds, in particular Actimid™ and Revimid™. Such methods can optionally further comprise the administration of other cancer therapies, such as but not limited to radiation therapy, biological therapies, hormonal therapies and/or surgery other than the administration of a JNK inhibitor.

In another specific embodiment, the invention provides prophylactic and therapeutic protocols comprising the administration of a JNK inhibitor in combination with one or more anti-metastatic agents, including, but not limited to sulphated polysaccharides and sulphaminoheparosanssulphates.

In another specific embodiment, the invention provides prophylactic and therapeutic regimens or protocols comprising the administration of a JNK inhibitor in combination with administration of one or more types of radiation therapy, such as external-beam radiation therapy, interstitial implantation of radioisotopes (I-125, palladium, iridium), radioisotopes such as strontium-89, thoracic radiation therapy, intraperitoneal P-32 radiation therapy, and/or total abdominal and pelvic radiation therapy. Such methods can optionally further comprise the administration of other cancer therapies, such as but not limited to chemotherapies, biological therapies/immunotherapies, bone marrow transplants, stem cell replacement therapies, hormonal therapies and/or surgery other than the administration of a JNK inhibitor.

In yet another specific embodiment, the invention provides prophylactic and therapeutic protocols comprising the administration of a JNK inhibitor in combination with one or more biological therapies/immunotherapies or hormonal therapies other than the administration of a JNK inhibitor, such as faslodex, tamoxifen, leuprolide or other LHRH agonists, non-steroidal antiandrogens (flutamide, nilutamide, bicalutamide), steroidal antiandrogens (cyproterone acetate), anti-inflammatory steroids (dexamethasone), estrogens (DES, chlorotrianisene, ethinyl estradiol, congugated estrogens U.S.P., DES-diphosphate), aromatase inhibitors (e.g., Arimidex®, anastrozole, letrozole and exemestane), aminoglutethimide, hydrocortisone, flutamide, progesterone, ketoconazole, prednisone, interferon alpha, interleukin-2, tumor necrosis factor-alpha, and/or melphalan. Such methods can optionally further comprise the administration of other cancer therapies, such as but not limited to radiation therapy, chemotherapies, bone marrow transplants, stem cell replacement therapies and/or surgery.

The invention provides methods of preventing, treating or managing cancer, including, but not limited to, the cancers discussed in Section 4.1.1.1. Specific examples of cancers that can be treated by the methods and compositions of the invention include, but are not limited to, cancer of the head, neck, eye, mouth, throat, esophagus, chest, bone, lung, colon, rectum, stomach, prostate, breast, ovaries, testicles or other reproductive organs, skin, thyroid, blood, lymph nodes, kidney, liver, pancreas, and brain or central nervous system. In particular embodiments, the prophylactic and/or therapeutic protocols are designed to prevent, treat or manage breast cancer. In certain embodiments, the prophylactic and/or therapeutic protocols are designed to prevent, treat, or manage colon cancer. The prophylactic and therapeutic regimens or protocols of the invention are also designed to prevent, treat, or manage prostate cancer. In other embodiments, the prophylactic and/or therapeutic protocols are designed to prevent, treat, or manage melanoma. In other embodiments, the prophylactic and/or therapeutic protocols are designed to prevent, treat, or manage multiple myeloma. In other embodiments, prophylactic and/or therapeutic protocols are designed to prevent, treat, or manage lung cancer. In yet other embodiments, prophylactic and/or therapeutic protocols are designed to prevent, treat, or manage ovarian cancer.

Preferred embodiments encompassed by the invention are methods of delivering one or more inhibitors of JNK as adjunctive therapy in combination with existing and experimental cancer therapies; pharmaceutical compositions and formulas for administration comprising one or more inhibitors of JNK and one or more existing cancer therapies; kits comprising said pharmaceutical compositions; and methods of treating, preventing, and/or managing cancer using the prophylactic or therapeutic protocols and pharmaceutical compositions of the invention. The invention also encompasses the administration of one or more inhibitors of JNK alone to patients refractory to other cancer treatments or that do not tolerate other such treatments because of unwanted or adverse effects.

4.1 Prophylactic/Therapeutic Methods

The present invention encompasses methods for treating, preventing, or managing cancer in a patient comprising administering one or more inhibitors of JNK in combination with one or more other therapeutic agents useful in the treatment, prevention or management of cancer. In certain embodiments, an inhibitor of JNK is administered to a mammal, preferably a human, concurrently with one or more other therapeutic agents useful for the treatment of cancer. The term "concurrently" is not limited to the administration of prophylactic or therapeutic agents at exactly the same time, but rather it is meant that an inhibitor of JNK and the other agent are administered to a mammal in a sequence and within a time interval such that the JNK inhibitor can act together with the other agent to provide an increased benefit than if they were administered otherwise. For example, each prophylactic or therapeutic agent (e.g., chemotherapy, radiation therapy, hormonal therapy or biological therapy) may be administered at the same time or sequentially in any order at different points in time; however, if not administered at the same time, they should be administered sufficiently close in time so as to provide the desired therapeutic or prophylactic effect. Each therapeutic agent can be administered separately, in any appropriate form and by any suitable route. In other embodiments, the JNK inhibitor is administered before, concurrently or after surgery. Preferably the surgery completely removes localized tumors or reduces the size of large tumors. Surgery can also be done as a preventive measure or to relieve pain. In various embodiments, the prophylactic or therapeutic agents are administered less than 1 hour apart, at about 1 hour apart, at about 1 hour to about 2 hours apart, at about 2 hours to about 3 hours apart, at about 3 hours to about 4 hours apart, at about 4 hours to about 5 hours apart, at about 5 hours to about 6 hours apart, at about 6 hours to about 7 hours apart, at about 7 hours to about 8 hours apart, at about 8 hours to about 9 hours apart, at about 9 hours to about 10 hours apart, at about 10 hours to about 11 hours apart, at about 11 hours to about 12 hours apart, no more than 24 hours apart or no more than 48 hours apart. In preferred embodiments, two or more components are administered within the same patient visit.

In other embodiments, the prophylactic or therapeutic agents are administered at about 2 to 4 days apart, at about 4 to 6 days apart, at about 1 week part, at about 1 to 2 weeks apart, or more than 2 weeks apart. In preferred embodiments, the prophylactic or therapeutic agents are administered in a time frame where both agents are still active. One skilled in the art would be able to determine such a time frame by determining the half life of the administered agents.

In certain embodiments, the prophylactic or therapeutic agents of the invention are cyclically administered to a patient. Cycling therapy involves the administration of a first agent for a period of time, followed by the administration of a second agent and/or third agent for a period of time and repeating this sequential administration. Cycling therapy can reduce the development of resistance to one or more of the therapies, avoid or reduce the side effects of one of the therapies, and/or improves the efficacy of the treatment.

In certain embodiments, prophylactic or therapeutic agents are administered in a cycle of less than about 3 weeks, about once every two weeks, about once every 10 days or about once every week. One cycle can comprise the administration of a therapeutic or prophylactic agent by infusion over about 90 minutes every cycle, about 1 hour every cycle, about 45 minutes every cycle. Each cycle can comprise at least 1 week of rest, at least 2 weeks of rest, at least 3 weeks of rest. The number of cycles administered is from about 1 to about 12 cycles, more typically from about 2 to about 10 cycles, and more typically from about 2 to about 8 cycles.

In other preferred embodiments, the JNK inhibitor is administered once a week or every two weeks; chemotherapy is administered daily for several days. In other preferred embodiments, chemotherapy is administered continuously for several days to several weeks. In yet other preferred embodiments, chemotherapy is administered in sessions of a few hours to a few days. It is contemplated that such methods include rest periods of a few weeks where no chemotherapy is administered.

In other preferred embodiments, the JNK inhibitor is administered once a week or every two weeks; radiation therapy is administered daily for several days. In other preferred embodiments, radiation therapy is administered three times per month for up to eight weeks. In yet other preferred embodiments, radiation therapy is administered one day per week for up to eight weeks. It is contemplated that such methods include rest periods of a few days or a few weeks where no radiation therapy is administered.

In other preferred embodiments, the JNK inhibitor is administered once a week or every two weeks; hormonal therapy is administered daily; biological therapy/immunotherapy is administered once a week or every two weeks.

In yet other embodiments, the therapeutic and prophylactic agents of the invention are administered in metronomic dosing regimens, either by continuous infusion or frequent administration without extended rest periods. Such metronomic administration can involve dosing at constant intervals without rest periods. Typically the therapeutic agents, in particular cytotoxic agents, are used at lower doses. Such dosing regimens encompass the chronic daily administration of relatively low doses for extended periods of time. In preferred embodiments, the use of lower doses can minimize toxic side effects and eliminate rest periods. In certain embodiments, the therapeutic and prophylactic agents are delivered by chronic low-dose or continuous infusion ranging from about 24 hours to about 2 days, to about 1 week, to about 2 weeks, to about 3 weeks to about 1 month to about 2 months, to about 3 months, to about 4 months, to about 5 months, to about 6 months. The scheduling of such dose regimens can be optimized by the skilled oncologist.

In other embodiments, courses of treatment are administered concurrently to a mammal, i.e., individual doses of the therapeutics are administered separately yet within a time interval such that the JNK inhibitor can work together with the other agent or agents. For example, one component may be administered one time per week in combination with the other components that may be administered one time every two weeks or one time every three weeks. In other words, the dosing regimens for the therapeutics are carried out concurrently even if the therapeutics are not administered simultaneously or within the same patient visit.

When used in combination with other prophylactic and/or therapeutic agents, the JNK inhibitor and the prophylactic and/or therapeutic agent can act additively or, more preferably, synergistically. In one embodiment, a JNK inhibitor is administered concurrently with one or more therapeutic agents in the same pharmaceutical composition. In another embodiment, a JNK inhibitor is administered concurrently with one or more other therapeutic agents in separate pharmaceutical compositions. In still another embodiment, a JNK inhibitor is administered prior to or subsequent to administration of another prophylactic or therapeutic agent.

The invention contemplates administration of a JNK inhibitor in combination with other prophylactic or therapeutic agents by the same or different routes of administration, e.g., oral and parenteral. In certain embodiments, when a JNK inhibitor is administered concurrently with another prophylactic or therapeutic agent that potentially produces adverse side effects including, but not limited to, toxicity, the prophylactic or therapeutic agent can advantageously be administered at a dose that falls below the threshold that the adverse side effect is elicited.

The dosage amounts and frequencies of administration provided herein are encompassed by the terms therapeutically effective and prophylactically effective. The dosage and frequency further will typically vary according to factors specific for each patient depending on the specific therapeutic or prophylactic agents administered, the severity and type of cancer, the route of administration, as well as age, body weight, response, and the past medical history of the patient. Suitable regimens can be selected by one skilled in the art by considering such factors and by following, for example, dosages reported in the literature and recommended in the *Physician's Desk Reference* (56$^{th}$ ed., 2002).

In one embodiment, the present invention provides methods of treating or preventing cancer by administering to a patient in need thereof JNK inhibitors in combination with anti-cancer agents or radiation therapy, wherein the JNK inhibitors have the following Illustrative JNK Inhibitors are set forth below.

In one embodiment, the JNK inhibitor has the following structure (I):

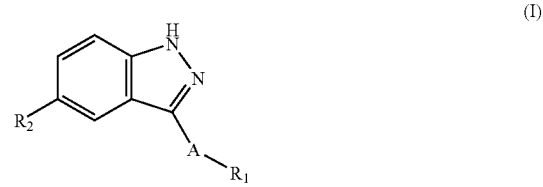

wherein:
A is a direct bond, —$(CH_2)_a$—, —$(CH_2)_b CH=CH(CH_2)_c$—, or —$(CH_2)_b C\equiv C(CH_2)_c$—;

$R_1$ is aryl, heteroaryl or heterocycle fused to phenyl, each being optionally substituted with one to four substituents independently selected from $R_3$;

$R_2$ is —$R_3$, —$R_4$, —$(CH_2)_b C(=O)R_5$, —$(CH_2)_b C(=O)OR_5$, —$(CH_2)_b C(=O)NR_5 R_6$, —$(CH_2)_b C(=O)NR_5(CH_2)C(=O)R_6$, —$(CH_2)_b NR_5 C(=O)R_6$, —$(CH_2)_b NR_5 C(=O)NR_6 R_7$, —$(CH_2)_b NR_5 R_6$, —$(CH_2)_b OR_5$, —$(CH_2)_b SO_d R_5$ or —$(CH_2)_b SO_2 NR_5 R_6$;

a is 1, 2, 3, 4, 5 or 6;

b and c are the same or different and at each occurrence independently selected from 0, 1, 2, 3 or 4;

d is at each occurrence 0, 1 or 2;

$R_3$ is at each occurrence independently halogen, hydroxy, carboxy, alkyl, alkoxy, haloalkyl, acyloxy, thioalkyl, sulfinylalkyl, sulfonylalkyl, hydroxyalkyl, aryl, arylalkyl, heterocycle, heterocycloalkyl, —$C(=O)OR_8$, —$OC(=O)R_8$, —$C(=O)NR_8 R_9$, —$C(=O)NR_8 OR_9$, —$SO_2 NR_8 R_9$, —$NR_8 SO_2 R_9$, —$CN$, —$NO_2$, —$NR_8 R_9$, —$NR_8 C(=O)R_9$, —$NR_8 C(=O)(CH_2)_b OR_9$, —$NR_8 C(=O)(CH_2)_b R_9$, —$O(CH_2)_b NR_8 R_9$, or heterocycle fused to phenyl;

$R_4$ is alkyl, aryl, arylalkyl, heterocycle or heterocycloalkyl, each being optionally substituted with one to four substituents independently selected from $R_3$, or $R_4$ is halogen or hydroxy;

$R_5$, $R_6$ and $R_7$ are the same or different and at each occurrence independently hydrogen, alkyl, aryl, arylalkyl, heterocycle or heterocycloalkyl, wherein each of $R_5$, $R_6$ and $R_7$ are optionally substituted with one to four substituents independently selected from $R_3$; and $R_8$ and $R_9$ are the same or different and at each occurrence independently hydrogen, alkyl, aryl, arylalkyl, heterocycle, or heterocycloalkyl, or $R_8$ and $R_9$ taken together with the atom or atoms to which they are bonded form a heterocycle, wherein each of $R_8$, $R_9$, and $R_8$ and $R_9$ taken together to form a heterocycle are optionally substituted with one to four substituents independently selected from $R_3$.

In one embodiment, -A-$R_1$ is phenyl, optionally substituted with one to four substituents independently selected from halogen, alkoxy, —NR$_8$C(=O)R$_9$, —C(=O)NR$_8$R$_9$, and —O(CH$_2$)$_b$NR$_8$R$_9$, wherein b is 2 or 3 and wherein $R_8$ and $R_9$ are defined above.

In another embodiment, $R_2$ is —R$_4$, —(CH$_2$)$_b$C(=O)R$_5$, —(CH$_2$)$_b$C(=O)OR$_5$, —(CH$_2$)$_b$C(=O)NR$_5$R$_6$, —(CH$_2$)$_b$C(=O)NR$_5$(CH$_2$)$_c$C(=O)R$_6$, —(CH$_2$)$_b$NR$_5$C(=O)R$_6$, —(CH$_2$)$_b$NR$_5$C(=O)NR$_6$R$_7$, —(CH$_2$)$_b$NR$_5$R$_6$, —(CH$_2$)$_b$OR$_5$, —(CH$_2$)$_b$SO$_d$R$_5$ or —(CH$_2$)$_b$SO$_2$NR$_5$R$_6$, and b is an integer ranging from 0-4.

In another embodiment, $R_2$ is —(CH$_2$)$_b$C(=O)NR$_5$R$_6$, —(CH$_2$)$_b$NR$_5$C(=O)R$_6$, 3-triazolyl or 5-tetrazolyl, wherein b is 0 and wherein $R_8$ and $R_9$ are defined above.

In another embodiment, $R_2$ is 3-triazolyl or 5-tetrazolyl.

In another embodiment:
(a) -A-$R_1$ is phenyl, optionally substituted with one to four substituents independently selected from halogen, alkoxy, —NR$_8$C(=O)R$_9$, —C(=O)NR$_8$R$_9$, and —O(CH$_2$)$_b$NR$_8$R$_9$, wherein b is 2 or 3; and
(b) $R_2$ is —(CH$_2$)$_b$C(=O)NR$_5$R$_6$, —(CH$_2$)$_b$NR$_5$C(=O)R$_6$, 3-triazolyl or 5-tetrazolyl wherein b is 0 and wherein $R_8$ and $R_9$ are defined above.

In another embodiment:
(a) -A-$R_1$ is phenyl, optionally substituted with one to four substituents independently selected from halogen, alkoxy, —NR$_8$C(=O)R$_9$, —C(=O)NR$_8$R$_9$, and —O(CH$_2$)$_b$NR$_8$R$_9$, wherein b is 2 or 3; and
(b) $R_2$ is 3-triazolyl or 5-tetrazolyl.

In another embodiment, $R_2$ is $R_4$, and $R_4$ is 3-triazolyl, optionally substituted at its 5-position with:
(a) a $C_1$-$C_4$ straight or branched chain alkyl group optionally substituted with a hydroxyl, methylamino, dimethylamino or 1-pyrrolidinyl group; or
(b) a 2-pyrrolidinyl group.

In another embodiment, $R_2$ is $R_4$, and $R_4$ is 3-triazolyl, optionally substituted at its 5-position with:

methyl, n-propyl, isopropyl, 1-hydroxyethyl, 3-hydroxypropyl, methylaminomethyl, dimethylaminomethyl, 1-(dimethylamino)ethyl, 1-pyrrolidinylmethyl or 2-pyrrolidinyl.

In another embodiment, the compounds of Structure (I) have Structure (IA) when A is a direct bond, or have Structure (IB) when A is —(CH$_2$)$_a$—:

(IA)

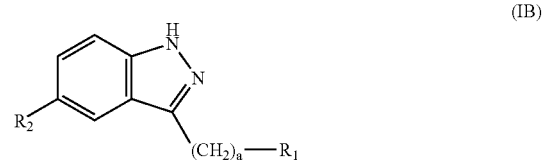

(IB)

In other embodiments, the compounds of structure (I) have structure (IC) when A is a —CH$_2$)$_b$CH=CH(CH$_2$)$_c$—, and have structure (ID) when A is —(CH$_2$)$_b$C≡C(CH$_2$)$_c$—:

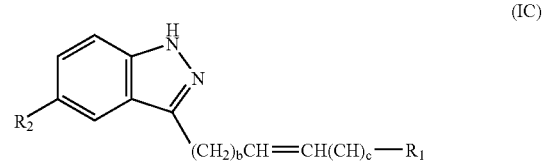

(IC)

(ID)

In further embodiments of this invention, $R_1$ of structure (I) is aryl or substituted aryl, such as phenyl or substituted phenyl as represented by the following structure (IE):

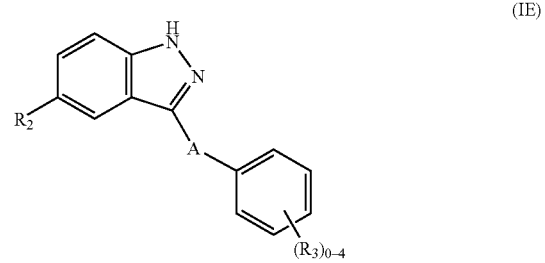

(IE)

In another embodiment, $R_2$ of structure (I) is —(CH$_2$)$_b$NR$_4$(C=O)R$_5$. In one aspect of this embodiment, b=0 and the compounds have the following structure (IF):

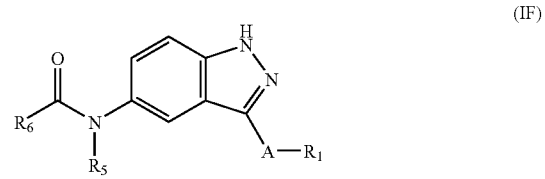

(IF)

Representative $R_2$ groups of the compounds of structure (I) include alkyl (such as methyl and ethyl), halo (such as chloro and fluoro), haloalkyl (such as trifluoromethyl), hydroxy, alkoxy (such as methoxy and ethoxy), amino, arylalkyloxy (such as benzyloxy), mono- or di-alkylamine (such as —NHCH$_3$, —N(CH$_3$)$_2$ and —NHCH$_2$CH$_3$), —NHC(=O)R$_4$ wherein R$_6$ is a substituted or unsubstituted phenyl or heteroaryl (such as phenyl or heteroaryl substituted with hydroxy, carboxy, amino, alkylester, alkoxy, alkyl, aryl, haloalkyl, halo, —CONH$_2$ and —CONH alkyl), —NH(heteroarylalkyl) (such as —NHCH$_2$(3-pyridyl), —NHCH$_2$(4-pyridyl), heteroaryl (such as pyrazolo, triazolo and tetrazolo), —C(=O)NHR$_6$ wherein R$_6$ is hydrogen, alkyl, or as defined above (such as —C(=O)NH$_2$, —C(=O)NHCH$_3$, —C(=O)NH(H-carboxyphenyl), —C(=O)N(CH$_3$)$_2$), arylalkenyl (such as phenylvinyl, 3-nitrophenylvinyl, 4-carboxyphenylvinyl), heteroarylalkenyl (such as 2-pyridylvinyl, 4-pyridylvinyl).

Representative R$_3$ groups of the compounds of structure (I) include halogen (such as chloro and fluoro), alkyl (such as methyl, ethyl and isopropyl), haloalkyl (such as trifluoromethyl), hydroxy, alkoxy (such as methoxy, ethoxy, n-propyloxy and isobutyloxy), amino, mono- or di-alkylamino (such as dimethylamine), aryl (such as phenyl), carboxy, niftro, cyano, sulfinylalkyl (such as methylsulfinyl), sulfonylalkyl (such as methylsulfonyl), sulfonamidoalkyl (such as —NHSO$_2$CH$_3$), —NR$_8$C(=O)(CH$_2$)$_b$OR$_9$ (such as NHC(=O)CH$_2$OCH$_3$), NHC(=O)R$_9$ (such as —NHC(=O)CH$_3$, —NHC(=O)CH$_2$C$_6$H$_5$, —NHC(=O)(2-furanyl)), and —O(CH$_2$)$_b$NR$_8$R$_9$ (such as —O(CH$_2$)$_2$N(CH$_3$)$_2$).

The compounds of structure (I) can be made using organic synthesis techniques known to those skilled in the art, as well as by the methods described in U.S. application Ser. No. 09/910,950, filed Jul. 23, 2001 and International Publication No. WO 02/10137, published Feb. 7, 2002, which are incorporated herein by reference in their entirety (particularly in Examples 1-430, at page 35, line 1 to page 396, line 12). Further, specific examples of these compounds are found in the application and publication.

In another embodiment, the JNK inhibitor has the following structure (II):

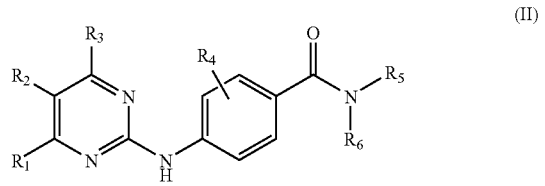

(II)

wherein:

R$_1$ is aryl or heteroaryl optionally substituted with one to four substituents independently selected from R$_7$;

R$_2$ is hydrogen;

R$_3$ is hydrogen or lower alkyl;

R$_4$ represents one to four optional substituents, wherein each substituent is the same or different and independently selected from halogen, hydroxy, lower alkyl and lower alkoxy;

R$_5$ and R$_6$ are the same or different and independently —R$_8$, —(CH$_2$)$_a$C(=O)R$_9$, —(CH$_2$)$_a$C(=O)OR$_9$, —(CH$_2$)$_a$C(=O)N$_9$R$_{10}$, —(CH$_2$)$_a$C(=O)NR$_9$(CH$_2$)$_b$C(=O)R$_{10}$, —(CH$_2$)$_a$NR$_9$C(=O)R$_{10}$, (CH$_2$)$_a$NR$_{11}$C(=O)NR$_9$R$_{10}$, —(CH$_2$)$_a$NR$_9$R$_{10}$, —(CH$_2$)$_a$OR$_9$, —(CH$_2$)$_a$SO$_c$R$_9$ or —(CH$_2$)$_a$SO$_2$N$_9$R$_{10}$;

or R$_5$ and R$_6$ taken together with the nitrogen atom to which they are attached to form a heterocycle or substituted heterocycle;

R$_7$ is at each occurrence independently halogen, hydroxy, cyano, nitro, carboxy, alkyl, alkoxy, haloalkyl, acyloxy, thioalkyl, sulfinylalkyl, sulfonylalkyl, hydroxyalkyl, aryl, aralkyl, heterocycle, substituted heterocycle, heterocyclealkyl, —C(=O)OR$_8$, —OC(=O)R$_8$, —C(=O)NR$_8$R$_9$, —C(=O)NR$_8$OR$_9$, —SO$_c$R$_8$, —SO$_c$NR$_8$R$_9$, —NR$_8$SO$_c$R$_9$, —NR$_8$R$_9$, —NR$_8$C(=O)R$_9$, —NR$_8$C(=O)(CH$_2$)$_b$OR$_9$, —NR$_8$C(=O)(CH$_2$)$_b$R$_9$, —O(CH$_2$)$_b$NR$_8$R$_9$, or heterocycle fused to phenyl;

R$_8$, R$_9$, R$_{10}$ and R$_{11}$ are the same or different and at each occurrence independently hydrogen, alkyl, aryl, aralkyl, heterocycle, heterocyclealkyl;

or R$_8$ and R$_9$ taken together with the atom or atoms to which they are attached to form a heterocycle;

a and b are the same or different and at each occurrence independently selected from 0, 1, 2, 3 or 4; and c is at each occurrence 0, 1 or 2.

In one embodiment, R$_1$ is a substituted or unsubstituted aryl or heteroaryl. When R$_1$ is substituted, it is substituted with one or more substituents defined below. In one embodiment, when substituted, R$_1$ is substituted with a halogen, sulfone or sulfonamide.

In another embodiment, R$_1$ is substituted or unsubstituted aryl, furyl, benzofuranyl, thiophenyl, benzothiophenyl, quinolinyl, pyrrolyl, indolyl, oxazolyl, benzoxazolyl, imidazolyl, benzimidazolyl, thiazolyl, benzothiazolyl, isoxazolyl, pyrazolyl, isothiazolyl, pyridazinyl, pyrimidinyl, pyrazinyl, triazinyl, cinnolinyl, phthalazinyl or quinazolinyl.

In another embodiment R$_1$ is substituted or unsubstituted aryl or heteroaryl. When R$_1$ is substituted, it is substituted with one or more substituents defined below. In one embodiment, when substituted, R$_1$ is substituted with a halogen, sulfone or sulfonamide.

In another embodiment, R$_1$ is substituted or unsubstituted aryl, preferably phenyl. When R$_1$ is a substituted aryl, the substituents are defined below. In one embodiment, when substituted, R$_1$ is substituted with a halogen, sulfone or sulfonamide.

In another embodiment, R$_5$ and R$_6$, taken together with the nitrogen atom to which they are attached form a substituted or unsubstituted nitrogen-containing non-aromatic heterocycle, preferably piperazinyl, piperidinyl or morpholinyl.

When R$_5$ and R$_6$, taken together with the nitrogen atom to which they are attached form substituted piperazinyl, piperadinyl or morpholinyl, the piperazinyl, piperadinyl or morpholinyl is substituted with one or more substituents defined below. In one embodiment, when substituted, the substituent is alkyl, amino, alkylamino, alkylether, acyl, pyrrolidinyl or piperidinyl.

In one embodiment, R$_3$ is hydrogen and R$_4$ is not present, and the compounds have the following structure (IIA):

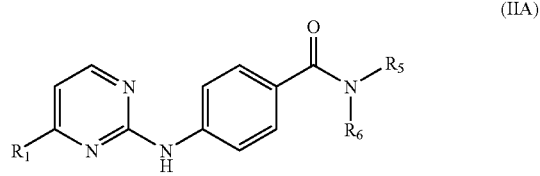

(IIA)

and pharmaceutically acceptable salts thereof.

In a more specific embodiment, $R_1$ is phenyl optionally substituted with $R_7$, and having the following structure (IIB):

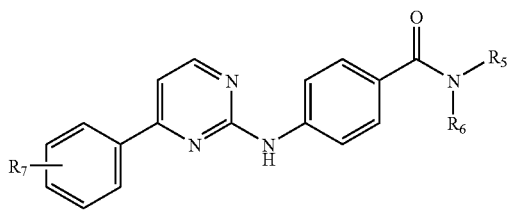

(IIB)

and pharmaceutically acceptable salts thereof

In still a further embodiment, $R_7$ is at the para position of the phenyl group relative to the pyrimidine, as represented by the following structure (IIC):

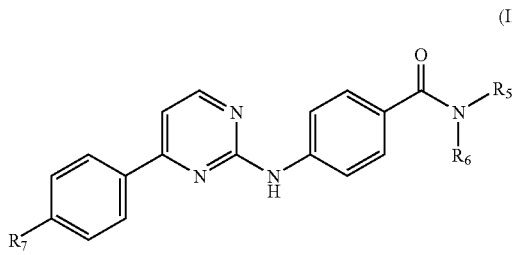

(IIC)

and pharmaceutically acceptable salts thereof.

The compounds of structure (II) can be made using organic synthesis techniques known to those skilled in the art, as well as by the methods described in U.S. application Ser. No. 10/004,645, filed Dec. 4, 2001, and International Publication No. WO 02/46170, published Jun. 13, 2002, which are hereby incorporated by reference in their entirety (particularly Examples 1-27 at page 23, line 5 to page 183, line 25). Further, specific examples of these compounds are found in said application and publication.

In another embodiment, the JNK inhibitor has the following structure (III):

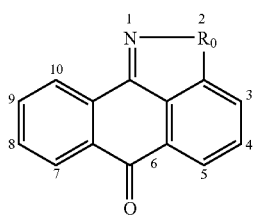

wherein $R_0$ is —O—, —S—, —S(O)—, —S(O)$_2$—, NH or —CH$_2$—;

the compound being (i) unsubstituted, (ii) monosubstituted and having a first substituent, or (iii) disubstituted and having a first substituent and a second substituent;

the first or second substituent, when present, is at the 3, 4, 5, 7, 8, 9, or 10 position, wherein the first and second substituent, when present, are independently alkyl, hydroxy, halogen, nitro, trifluoromethyl, sulfonyl, carboxyl, alkoxycarbonyl, alkoxy, aryl, aryloxy, arylalkyloxy, arylalkyl, cycloalkylalkyloxy, cycloalkyloxy, alkoxyalkyl, alkoxyalkoxy, aminoalkoxy, mono-alkylaminoalkoxy, di-alkylaminoalkoxy, or a group represented by formula (a), (b), (c), (d), (e), or (f):

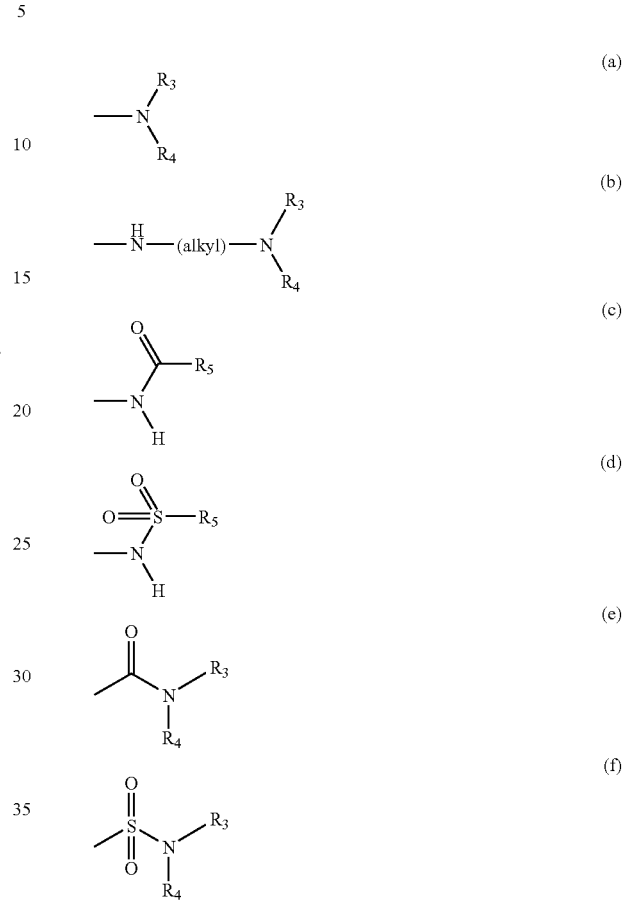

wherein $R_3$ and $R_4$ are taken together and represent alkylidene or a heteroatom-containing alkylidene or $R_3$ and $R_4$ are independently hydrogen, alkyl, cycloalkyl, aryl, arylalkyl, cycloalkylalkyl, aryloxyalkyl, alkoxyalkyl, aminoalkyl, mono-alkylaminoalkyl, or di-alkylaminoalkyl; and $R_5$ is hydrogen, alkyl, cycloalkyl, aryl, arylalkyl, cycloalkylalkyl, alkoxy, alkoxyalkyl, alkoxycarbonylalkyl, amino, mono-alkylamino, di-alkylamino, arylamino, arylalkylamino, cycloalkylamino, cycloalkylalkylamino, aminoalkyl, mono-alkylaminioalkyl, or di-alkylaminoalkyl;

or a pharmaceutically acceptable salt thereof.

In another embodiment, the JNK inhibitor has the following structure (IV):

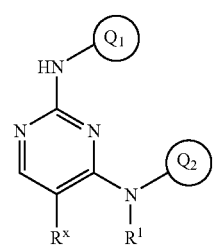

(IV)

wherein:

R$_1$ is selected from hydrogen, C$_{1-6}$ alkyl (optionally substituted by one or two substituents independently selected from halo, amino, C$_{1-4}$ alkylamino, di-(C$_{1-4}$ alkyl) amino, hydroxy, cyano, C$_{1-4}$ alkoxy, C$_{1-4}$ alkoxy, C$_{1-4}$ alkoxycarbonyl, carbamoyl, —NHCOC$_{1-4}$ alkyl, trifluoromethyl, phenylthio, phenoxy, pyridyl, morpholino), benzyl, 2-phenylethyl, C$_{3-5}$ alkenyl (optionally substituted by up to three halo substituents, or by one trifluoromethyl substituent, or one phenyl substituent), N-phthalimido-C$_{1-4}$ alkyl, C$_{3-5}$ alkynyl (optionally substituted by one phenyl substitutent) and C$_{3-6}$ cycloalkyl-C$_{1-6}$ alkyl; wherein any phenyl or benzyl group in R$^1$ is optionally substituted by up to three substituents independently selected from halo, hydroxy, nitro, amino, C$_{1-3}$ alkylamino, di-(C$_{1-3}$ alkyl) amino, cyano, trifluoromethyl, C$_{1-3}$alkyl (optionally substituted by 1 or 2 substituents independently selected from halo, cyano, amino, C$_{1-3}$ alkylamino, di-(C$_{1-3}$ alkyl) amino, hydroxy and trifluoromethyl), C$_{3-5}$ alkenyl (optionally substituted by up to three halo substituents, or by one trifluoromethyl substituent), C$_{3-5}$ alkynyl, C$_{1-3}$ alkoxy, mercapto, C$_{1-3}$ alkylthio, carboxy, C$_{1-3}$ alkoxycarbonyl;

R$^x$ is selected from halo, hydroxy, nitro, amino, cyano, mercapto, carboxy, sulphamoyl, formamido, ureido or carbamoyl or a group of structure (IVb):

A-B-C            (IVb)

wherein:

A is C$_{1-6}$ alkyl, C$_{2-6}$ alkenyl, C$_{1-6}$ alkynyl, C$_{3-8}$ cycloalkyl, phenyl, heterocycle or heteroaryl, wherein said C$_{1-6}$ alkyl, C$_{3-6}$ alkynyl are are optionally substituted by one or more substituents selected from halo, nitro, cyano, amino, hydroxy, mercapto, carboxy, formamido, ureido, C$_{1-3}$ alkylamino, di-(C$_{1-3}$ alkyl) amino, C$_{1-3}$ trifluoromethyl, C$_{3-8}$ cycloalkyl, phenyl, heterocycle or heteroaryl; wherein any phenyl, C$_{3-8}$ cycloalkyl, heterocycle or heteroaryl may be optionally substituted by one or more halo, nitro, cyano, hydroxy, trifluoromethyl, tri fluorometlioxy, amino, carboxy, carbamoyl, mercapto, formamido, ureido, sulphamoyl, C$_{1-4}$ alkyl, C$_{2-4}$ alkenyl, C$_{2-4}$ alkynyl, C$_{1-4}$ alkoxy, C$_{1-4}$ alkanoyl, C$_{1-4}$ alkanoyloxy, C$_{1-4}$ alkylamino, di-(C$_{1-4}$ alkyl)amino, C$_{1-4}$ alkanoylamino, N-C$_{1-4}$ alkylcarbamoyl, N,N-di-(C$_{1-4}$ alkyl)carbamoyl, C$_{1-4}$ alkylthio, C$_{1-4}$ alkylsulphinyl, C$_{1-4}$ alkylsulphonyl and C$_{1-4}$ alkoxycarbonyl;

B is —O—, -5-, —C(O)—, —NH—, —N(C$_{1-4}$ alkyl)-, —C(O)NH—, —C(O)N(C$_{1-4}$ alkyl)-, NHC(O)—, —N(C$_{1-4}$ alkyl)C(O)— or B is a direct bond;

C is C$_{1-4}$ alkylene or a direct bond;

Q$_1$ and Q$_2$ are independently selected from aryl, a 5- or 6-membered monocyclic moiety (linked via a ring carbon atom and containing one to three heteroatoms independently selected from nitrogen, oxygen and sulphur); and a 9- or 10-membered bicyclic heterocyclic moiety (linked via a ring carbon atom and containing one or two nitrogen heteroatoms and optionally containing a further one or two heteroatoms selected from nitrogen, oxygen and sulphur);

and one or both of Q$_1$ and Q$_2$ is substituted on any available carbon atom with one substituent of the structure (IVa) and Q$_2$, may optionally be further substituted on any available carbon atom with a substituent of the structure (IVa):

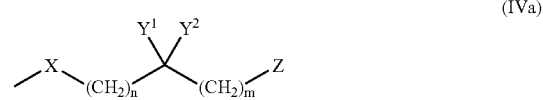

(IVa)

(provided that when present in Q$_1$ the substituent of formula (IVa) is not adjacent to the —NH-link);

wherein:

X is —CH$_2$—, —O—, —NH—, —NR$^y$— or —S— (wherein R$^y$ is C$_{1-4}$ alkyl, optionally substituted by one substituent selected from halo, amino, cyano, C$_{1-4}$ alkoxy or hydroxy);

Y$^1$ is H, C$_{1-4}$ alkyl or as defined for Z;

Y$^2$ is H or C$_{1-4}$ alkyl;

Z is R$^3$O—, R$^b$R$^c$N—, R$^d$S—, R$^e$R$^f$NNR$^g$—, a nitrogen linked heteroaryl or a nitrogen linked heterocyclic (wherein said heterocycle is optionally substituted on a ring carbon or a ring nitrogen by C$_{1-4}$ alkyl or C$_{2-4}$ alkanoyl) wherein R$^a$, R$^b$, R$^c$, R$^d$, R$^e$, R$^f$ and R$^g$ are independently selected from hydrogen, C$_{1-4}$ alkyl, C$_{2-4}$ alkenyl, C$_{3-8}$ cycloalkyl, and wherein said C$_{1-4}$ alkyl and C$_{2-4}$ alkenyl are optionally substituted by one or more phenyl;

n is 1, 2 or 3;

m is 1, 2 or 3;

and Q$_1$ may optionally be substituted on any available carbon atom with up to four substituents independently selected from halo, thio, nitro, carboxy, cyano, C$_{2-4}$ alkenyl (optionally substituted by up to three halo substituents, or by one trifluoromethyl substituent), C$_{2-4}$ alkynyl, C$_{1-5}$ alkanoyl, C$_{1-4}$ alkoxycarbonyl, C$_{1-5}$ alkyl, hydroxy-C$_{1-3}$ alkyl, fluoro-C$_{1-4}$ alkyl, amino-C$_{1-3}$ alkyl, C$_{1-4}$ alkylamino-C$_{1-3}$ alkyl, di-(C$_{1-4}$ alkyl)amino-C$_{1-3}$ alkyl, cyano-C$_{1-4}$ alkyl, C$_{2-4}$ alkanoyloxy-C$_{1-4}$ alkyl, C$_{1-4}$ alkoxy-C$_{1-3}$ alkyl, carboxy-C$_{1-4}$ alkyl, C$_{1-4}$ alkoxycarbonyl-C$_{1-4}$ alkyl, carbamoyl-C$_{1-4}$ alkyl, N-C$_{1-4}$ alkylcarbamoyl-C$_{1-4}$ alkyl, N,N-di-(C$_{1-4}$ alkyl)-carbamoyl-C$_{1-4}$ alkyl pyrrolidin-1-yl-C$_{1-3}$ alkyl, piperidino-C$_{1-3}$ alkyl, piperazin-)-yl-C$_{1-3}$ alkyl, morpholino-C$_{1-3}$ alkyl, thiomorpholino-C$_{1-3}$ alkyl, imidazo-1-yl-C$_{1-3}$ alkyl, piperazin-1-yl, morpholino, thiomorpholino, C$_{1-4}$ alkylthio, C$_{1-4}$ alkylsulphinyl, C$_{1-4}$ alkylsulphonyl, hydroxy C$_{2-4}$ alkylthio, hydroxy C$_{2-4}$ alkylsulphinyl, hydroxy C$_{2-4}$ alkylsulphonyl, ureido, N'-(C$_{1-4}$ alkyl)ureido, N'-N'-di-(C$_{1-4}$ alkyl)ureido, N'-(C$_{1-4}$ alkyl)-N-(C$_{1-4}$ alkyl)ureido, N',N'-di-(C$_{1-4}$ alkyl)-N—(C$_{1-4}$ alkyl)ureido, carbamoyl, N—(C$_{1-4}$ alkyl)carbamoyl, N,N-di-(C$_{1-4}$ alkyl)carbamoyl, amino, C$_{1-4}$ alkylamino, di-(C$_{1-4}$ alkyl)amino, C$_{2-4}$ alkanoylamino, sulphamoyl, N—(C$_{1-4}$ alkyl)sulphamoyl, N,N-di-(C$_{1-4}$ alkyl) sulphamoyl;

and also independently, or where appropriate in addition to, the above substituents, Q$_1$ may optionally be substituted on any available carbon atom up with to two further substituents independently selected from C$_{3-8}$ cycloalkyl, phenyl-C$_{1-4}$ alkyl, phenyl-C$_{1-4}$ alkoxy, phenylthio, phenyl, naphthyl, benzoyl, benzimidazol-2-yl, phenoxy and a 5- or 6-membered aromatic heterocycle (linked via a ring carbon atom and containing one to three heteroatoms independently selected from oxygen, sulphur and nitrogen); wherein said naphthyl, phenyl, benzoyl, phenoxy, 5- or 6-membered aromatic heterocyclic substituents and the phenyl group in said phenyl-C$_{1-4}$ alkyl, phenylthio and phenyl-C$_{1-4}$ alkoxy substituents may optionally be substituted with up to five substituents independently selected from halo, C$_{1-4}$ alkyl and C$_{1-4}$ alkoxy;

and Q$_2$ may optionally be substituted on any available carbon atom with up to four substituents independently selected from halo, hydroxy, thio, nitro, carboxy, cyano, C$_{2-4}$ alkenyl (optionally substituted by up to three halo substituents, or by one trifluoromethyl substituent), C$_{2-4}$ alkynyl, C$_{1-5}$ alkanoyl, C$_{1-4}$ alkoxycarbonyl, C$_{1-6}$ alkyl, hydroxy-C$_{1-3}$ alkyl, fluoro-C$_{1-4}$ alkyl, amino-C$_{1-3}$ alkyl, C$_{1-4}$ alkylamino-C$_{1-3}$ alkyl, di-(C$_{1-4}$ alkyl)amino-C$_{1-3}$ alkyl, cyano-C$_{1-4}$ alkyl, C$_{2-4}$ alkanoyloxy-C$_{1-4}$ alkyl, C$_{1-4}$ alkoxy-C$_{1-3}$ alkyl, carboxy-C$_{1-4}$ alkyl, C$_{1-4}$ alkoxycarbonyl-C$_{1-4}$ alkyl, carbamoyl-C$_{1-4}$ alkyl, N-C$_{1-4}$ alkylcarbamoyl-C$_{1-4}$ alkyl, N,N-di-(C$_{1-4}$ alkyl)-carbamoyl-C$_{1-4}$ alkyl pyrrolidin-1-yl-C$_{1-3}$ alkyl, piperidino-C$_{1-3}$ alkyl, piperazin-)-yl-C$_{1-3}$ alkyl, morpholino-C$_{1-3}$ alkyl, thiomorpholino-C$_{1-3}$ alkyl, imidazo-1-yl-C$_{1-3}$ alkyl, piperazin-1-yl, morpholino, thiomorpholino, C$_{1-4}$ alkoxy, cyano-C$_{1-4}$ alkoxy, carbamoyl-C$_{1-4}$ alkoxy N'-(C$_{1-4}$ alkylcarbamoyl, C$_{1-4}$ alkyl)alkoxy, N,N-di-(C$_{1-4}$ alkyl)-carbamoyl-C$_{1-4}$ alkyl, 2-aminoethoxy, 2-C$_{1-4}$ alkylaminoethoxy, 2-di-(C$_{1-4}$alkyl)aminoethoxy, C$_{1-4}$ alkoxycarbonyl-C$_{1-4}$ alkoxy, halo-C$_{1-4}$ alkoxy, 2-hydroxyethoxy, C$_{2-4}$ alkanoyloxy-C$_{1-4}$ alkoxy, 2-C$_{1-4}$ alkoxyethoxy, carboxy-C$_{1-4}$ alkoxy, 2-pyrrolidin-1-yl-ethoxy, 2-piperidino-ethoxy, 2-piperazin-1-yl-ethoxy, 2-morpholino-ethoxy, 2-thiomorpholino-ethoxy, 2-imidazo-1-yl-ethoxy, C$_{3-5}$ alkenyloxy, C$_{3-5}$ alkynyloxy, C$_1$-C$_4$ alkylthio, C$_{1-4}$ alkylsulphinyl, C$_{1-4}$ alkylsulphonyl, hydroxy C$_{2-4}$ alkylthio, hydroxy C$_{2-4}$-alkylsulphinyl, hydroxy C$_{2-4}$ alkylsulphonyl, ureido, N'-(C$_{1-4}$ alkyl) ureido, N',N'-di-(C$_{1-4}$ alkyl)ureido, N'-(C$_{1-4}$ alkyl)-N-(C$_{1-4}$ alkyl)ureido, N',N'-di-(C$_{1-4}$ alkyl)-N-(C$_{1-4}$ alkyl)ureido, carbamoyl, N'-(C$_{1-4}$ alkyl)carbamoyl, N,N-di-(C$_{1-4}$ alkyl)carbamoyl, amino, C$_{1-4}$ alkylamino, di-(C$_{1-4}$ alkyl)amino, C$_{2-4}$ alkanoylamino, sulphamoyl, N-(C$_{1-4}$ 4alkyl)sulphamoyl, N,N-di-(C$_{1-4}$ alkyl)sulphamoyl, and also independently, or where appropriate in addition to, the above optional substituents, Q$_2$ may optionally be substituted on any available carbon atom with up to two further substituents independently selected from C$_{3-8}$ cycloalkyl, phenyl-C$_{1-4}$ alkyl, phenyl-C$_{1-4}$-alkoxy, phenylthio, phenyl, naphthyl, benzoyl, phenoxy, benzimidazol-2-yl, and a 5- or 6-membered aromatic heterocycle (linked via a ring carbon atom and containing one to three heteroatoms independently selected from oxygen, sulphur and nitrogen); wherein said naphthyl, phenyl, benzoyl, phenoxy, 5- or 6-membered aromatic heterocyclic substituents and the phenyl group in said phenyl-C$_{1-4}$ alkyl, phenylthio and phenyl-C$_{1-4}$ alkoxy substituents may optionally be substituted with one or two substituents independently selected from halo, C$_{1-4}$ alkyl and C$_{1-4}$ alkoxy.

The compounds of structure (IV) can be made using organic synthesis techniques known to those skilled in the art, as well as by the methods described in International Publication No. WO 00/39101, which is incorporated herein by reference in its entirety (particularly at page 2, line 10 to page 6, line 12). Further, specific examples of these compounds can be found in this publication.

In another embodiment, the JNK inhibitor has the following structure (V):

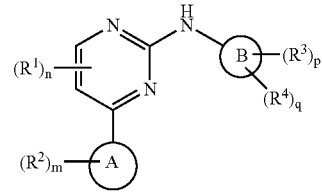

(V)

wherein:

Ring A is imidazo(1,2a)pyrid-3-yl or pyrazolo(2,3a)pyrid-3-yl;

R$^2$ is attached to a ring carbon and is selected from halo, nitro, cyano, hydroxy, trifluoromethyl, trifluoromethoxy, amino, carboxy, carbamoyl, mercapto, sulphamoyl, C$_{1-6}$ alkyl, C$_{2-6}$ alkenyl, C$_{2-6}$ alkynyl, C$_{1-6}$ alkoxy, C$_{1-6}$ alkanoyl, C$_{1-6}$ alkanoyloxy, N-(C$_{1-6}$ alkyl)amino, N,N-(C$_{1-6}$ alkyl) amino, C$_{1-6}$ alkanoylamino, N-(C$_{1-6}$ alkyl)carbamoyl, N,N-(C$_{1-6}$ alkyl)$_2$ carbamoyl, C$_{1-6}$ alkylS(O)$_a$ wherein a is 0 to 2, C$_{1-6}$ alkoxycarbonyl, N-(C$_{1-6}$ alkyl)sulphamoyl, N,N-(C$_{1-6}$ alkyl)$_2$ sulphamoyl, phenyl, heterocyclic group, phenylthio or (heterocyclic group)thio; wherein any C$_{1-6}$ alkyl, C$_{2-6}$ alkenyl, C$_{2-6}$ alkynyl, phenyl or heterocyclic group may be optionally substituted on carbon by one or more G; and wherein if said heterocyclic group contains an —NH— moiety that nitrogen may be optionally substituted by a group selected from Q;

m is 0-5; wherein the values of R$^2$ may be the same or different;

R$^1$ is halo, nitro, cyano, hydroxy, trifluoromethyl, trifluoromethoxy, amino, carboxy, carbamoyl, mercapto, sulphamoyl, C$_{1-3}$ alkyl, C$_{2-3}$ alkenyl, C$_{2-3}$ alkynyl, C$_{1-3}$ alkoxy, C$_{1-3}$ alkanoyl, N—(C$_{1-3}$ alkyl)amino, N,N-(C$_{1-2}$ alkyl)$_2$ amino, C$_{1-3}$ alkanoylamino, N-(C$_{1-3}$ alkyl)carbamoyl, N,N-(C$_{1-2}$ alkyl)$_2$ carbamoyl, C$_{1-3}$ alkylS(O)$_a$ wherein a is 0 to 2, N-(C$_{1-3}$ alkyl)sulphamoyl or N,N-(C$_{1-3}$ alkyl)$_2$ sulphamoyl; wherein any C$_{1-2}$ alkyl, C$_{1-3}$ alkyl, C$_{2-3}$ alkenyl or C$_{2-3}$ alkynyl may be optionally substituted on carbon by one or more J;

n is 0 to 2; wherein the values of R$^1$ may be the same or different;

Ring B is phenyl or phenyl fused to a C$_{5-7}$ cycloalkyl ring;

R$^3$ is halo, nitro, cyano, hydroxy, amino, carboxy, carbamoyl, mercapto, sulphamoyl, C$_{2-6}$alkenyl or C$_{2-6}$ alkynyl;

p is 0-4; wherein the values of R$^3$ may be the same or different;

R$^4$ is a group A-E; wherein

A is selected from C$_{1-6}$ alkyl, phenyl, a heterocyclic group, C$_{3-8}$ cycloalkyl, phenylC$_{1-6}$ alkyl, (heterocyclic group)C$_{1-6}$ alkyl or C$_{3-8}$ cycloalkyl C$_{1-6}$ cycloalkyl; which C$_{1-6}$ alkyl, phenyl, a heterocyclic group, C$_{3-8}$ cycloalkyl, phenyl C$_{1-6}$ alkyl, (heterocyclic group) C$_{1-6}$ alkyl, or C$_{3-8}$ cycloalkyl-C$_{1-6}$ cycloalkyl may be optionally substituted on carbon by one or more D; and wherein if said heterocyclic group contains an —NH— moiety that nitrogen may be optionally substituted by a group selected from R;

E is a direct bond or —O—, —C(O)—, —OC(O)—, —C(O)O—, —N(R$^a$)C(O)—, —C(O)N(R$^a$)—, —N(R$^a$)—, S(O)$_r$—, —SO$_2$N(R$^a$)— or N(R$^a$)SO$_2$—; wherein R$^a$ is hydrogen or C$_{1-6}$ alkyl optionally substituted by one or more D and r is 0-2;

D is independently selected from oxo, halo, nitro, cyano, hydroxy, trifluoromethyl, trifluoromethoxy, amino, carboxy, carbamoyl, mercapto, sulphamoyl, $C_{1-6}$ alkyl, $C_{2-6}$ alkenyl, $C_{1-6}$alkoxy, $C_{1-6}$ alkanoyl, $C_{1-6}$ alkanoyloxy, N-($C_{1-6}$ alkyl) amino, N,N-($C_{1-6}$ alkyl)$_2$ amino, $C_{1-6}$ alkanoylamino, N-($C_{1-6}$ alkyl)carbamoyl, N,N-($C_{1-6}$ alkyl)$_2$ carbamoyl, $C_{1-6}$ alkylS(O)$_a$ wherein a is 0 to 2, $C_{1-6}$ alkoxycarbonyl, $C_{1-6}$ alkoxycarbonylamino, benzyloxcarbonylamino, N-($C_{1-6}$ alkyl)sulphamoyl and N,N-($C_{1-6}$ alkyl)$_2$ sulphamoyl; wherein any $C_{1-6}$ alkyl, $C_{2-6}$ alkenyl, $C_{2-6}$ alkynyl or phenyl may be optionally substituted on carbon by one or more K;

q is 0-2; wherein the values of $R^4$ may be the same or different; and wherein p+q≦5;

G, J and K are independently selected from halo, nitro, cyano, hydroxy, trifluoromethyl, trifluoromethoxy, amino, carboxy, carbamoyl, mercapto, sulphamoyl, methyl, ethyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N-dimethylcarbamoyl, N,N-diethylcarbamoyl, N-methyl-N-ethylcarbamoyl, methylthio, ethylthio, methylsulphinyl, ethylsulphinyl, mesyl, ethylsulphonyl, methoxycarbonyl, ethoxycarbonyl, N-methylsulphamoyl, N-ethylsulphamoyl, N,N-dimethylsulphamoyl, N,N-diethylsulphamoyl or N-methyl-N-ethylsulphamoyl; and Q and R are independently selected from $C_{1-4}$ alkyl, $C_{1-4}$ alkanoyl, $C_{1-4}$ alkylsulphonyl, $C_{1-4}$ alkoxycarbonyl,carbamoyl, N-($C_{1-4}$ alkyl)carbamoyl, N,N-$C_{1-4}$ alkyl)carbamoyl, benzyl, benzyloxycarbonyl, benzoyl and phenylsulphonyl; or pharmaceutically acceptable in vivo hydrolyzable esters, analogs, hydrolysis products, metabolites, salts, solvates, hydrates, clathrates, polymorphs, stereoisomers, derivatives and precursors thereof.

The compounds of structure (V) can be made using organic synthesis techniques known to those skilled in the art, as well as by the methods described in International Publication No. WO 01/14375, which is incorporated herein by reference in its entirety (particularly at page 2, line 4 to page 4, line 4). Further, specific examples of these compounds can be found in this publication.

In another embodiment, the JNK inhibitor has the following structure (VI):

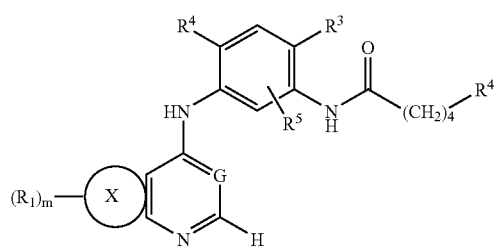

(VI)

wherein:

G is N, CH or C(CN);

ring X is a 5- or 6-membered fused heteroaryl ring which contains 1, 2 or 3 heteroatoms selected from oxygen, sulphur and nitrogen;

m is 0, 1 or 2;

$R^1$ is hydroxy, halo, trifluoromethyl, cyano, mercapto, nitro, amino, carboxy, carbamoyl, formyl, sulphamoyl, $C_{1-6}$ alkyl, $C_{2-6}$ alkenyl, $C_{2-6}$ alkynyl, $C_{1-6}$ alkoxy, —O—($C_{1-3}$ alkyl)-O—, $C_{1-6}$ alkylS(O)$_a$—(wherein n is 0-2), N-$C_{1-6}$ alkylamino, N,N-($C_{1-6}$ alkyl)$_2$amino, $C_{1-6}$ alkoxycarbonyl, N-$C_{1-6}$ alkylcarbamoyl, N,N-($C_{1-6}$ alkyl)$_2$ carbamoyl, $C_{2-6}$ alkanoyl, $C_{1-6}$ alkanoyloxy, $C_{1-6}$ alkanoylamino, N-$C_{1-6}$ alkylsulphamoyl, N,N-($C_{1-6}$ alkyl)$_2$ sulphamoyl, $C_{1-6}$ alkylsulphonylamino, $C_{1-6}$ alkylsulphonyl-N-($C_{1-6}$ alkyl)amino, or $R^1$ is of the Structure (IA):

A-(CH$_2$)$_p$-B-    (VIA)

wherein A is halo, hydroxy, $C_{1-6}$ alkoxy, $C_{1-6}$ alkylS(O)$_n$— (wherein n is 0-2), cyano, amino, N-$C_{1-6}$ alkylamino, N,N-($C_{1-6}$ alkyl)$_2$ amino, carboxy, $C_{1-6}$ alkoxycarbonyl, carbamoyl, N-$C_{1-6}$ alkylcarbamoyl or N,N-($C_{1-6}$ alkyl)$_2$ carbamoyl, p is 1-6, and B is a bond, oxy, imino, N-($C_{1-6}$ alkyl) imino or —C(O)NH—, or $R^1$ is of the Structure (VIB):

D-E-    (VIB)

wherein D is aryl, heteroaryl or heterocyclyl and E is a bond, $C_{1-6}$ alkylene, $C_{1-6}$ alkyleneoxy, oxy, imino, N-($C_{1-6}$ alkyl) imino, $C_{1-6}$ alkyleneimino, N-($C_{1-6}$ alkyl)-$C_{1-6}$ alkyleneimino, $C_{1-6}$ alkyleneoxy-$C_{1-6}$ alkylene, $C_{1-6}$ alkyleneimino-$C_{1-6}$ alkylene, N-($C_{1-6}$ alkyl)-$C_{1-6}$ alkyleneimino-$C_{1-6}$ alkylene, —C(O)NH—, —SO$_2$NH—, —NHSO$_2$— or $C_{2-6}$ alkanoylimino, and any aryl, heteroaryl or heterocyclyl group in a $R^1$ group may be optionally substituted with one or more groups selected from hydroxy, halo, $C_{1-6}$ alkyl, $C_{1-6}$ alkoxy, carboxy, $C_{1-6}$ alkoxycarbonyl, carbamoyl, N-$C_{1-6}$ alkylcarbamoyl, N-($C_{1-6}$ alkyl), carbamoyl, $C_{2-6}$ alkanoyl, amino, N-$C_{1-6}$ alkylamino and N,N-($C_{1-6}$ alkyl),amino, and any heterocyclyl group in a $R^1$ group may be optionally substituted with one or two oxo or thioxo substituents, and any of the $R^1$ groups defined hereinbefore which comprises a CH$_2$ group which is attached to 2 carbon atoms or a CH$_3$ group which is attached to a carbon atom may optionally be substituted on each said CH$_2$ or CH$_3$ group with a substituent selected from hydroxy, amino, $C_{1-6}$ alkoxy, N-$C_{1-6}$ alkylamino, N,N-($C_{1-6}$ alkyl),amino and heterocyclyl;

$R^2$ is hydrogen, halo, $C_{1-6}$ alkyl, $C_{1-6}$ alkenyl or $C_{2-6}$ alkynyl;

$R^3$ is hydrogen, halo, $C_{1-6}$ alkyl, $C_{2-6}$ alkenyl or $C_{2-6}$ alkynyl;

$R^4$ is hydrogen, hydroxy, $C_{1-6}$ alkyl, $C_{1-6}$ alkoxy, amino, N-$C_{1-6}$ alkylamino, N,N-($C_{1-6}$ alkyl)$_2$ amino, hydroxy-$C_{2-6}$ alkoxy, $C_{1-6}$ alkoxy$C_{2-6}$ alkoxy, amino-$C_{2-6}$ alkoxy, N-$C_{1-6}$ alkylamino$C_{2-6}$ alkoxy, N,N-($C_{1-6}$ alkyl), amino-$C_{2-6}$ alkoxy or $C_{3-7}$ cycloalkyl, or $R^4$ is or the Structure (VIC):

-K-J    (VIC)

wherein J is aryl, heteroaryl or heterocyclyl and K is a bond, oxy, imino, N-($C_{1-6}$ alkyl)imino, oxy-$C_{1-6}$ alkylene, imino-$C_{1-6}$ alkylene, N-($C_{1-6}$ alkyl)imino-$C_{1-6}$ alkylene, —NHC(O)—, —SO$_2$NH—, —NHSO$_2$— or —NHC(O)—$C_{1-6}$ alkylene-, and any aryl, heteroaryl or heterocyclyl group in a $R^4$ group may be optionally substituted by one or more groups selected from hydroxy, halo, trifluoromethyl, cyano, mercapto, nitro, amino, carboxy, carbamoyl, formyl, sulphamoyl, $C_{1-6}$ alkyl, $C_{2-6}$ alkenyl, $C_{2-6}$ alkynyl, $C_{1-6}$ alkoxy, —O—($C_{1-3}$ alkyl)-O—, $C_{1-6}$ alkylS(O)$_n$— (wherein n is 0-2), N-$C_{1-6}$ alkylamino, N,N-($C_{1-6}$ alkyl)$_2$amino, $C_{1-6}$ alkoxycarbonyl, N-$C_{1-6}$ alkylcarbamoyl, N,N-($C_{1-6}$ alkyl)$_2$ carbamoyl, $C_{2-6}$ alkanoyl, $C_{1-6}$ alkanoyloxy, $C_{1-6}$ alkanoylamino, N-$C_{1-6}$ alkylsulphamoyl, N,N-($C_{1-6}$ alkyl)$_2$ sulphamoyl, $C_{1-6}$ alkylsulphonylamino and $C_{1-6}$ alkylsulphonyl-N-($C_{1-6}$ alkyl) amino, or any aryl, heteroaryl or heterocyclyl group in a $R^4$ group may be optionally substituted with one or more groups of the Structure (VIA$^1$):

$$-B^1-(CH_2)_p-A^1 \qquad (VIA^1)$$

wherein A$^1$ is halo, hydroxy, C$_{1-6}$ alkoxy, cyano, amino, N-C$_{1-6}$ alkylamino, N,N-(C$_{1-6}$ alkyl)$_2$ amino, carboxy, C$_{1-6}$ alkoxycarbonyl, carbamoyl, N-C$_{1-6}$ alkylcarbamoyl or N,N-(C$_{1-6}$ alkyl)$_2$carbamoyl, p is 1-6, and B$^1$ is a bond, oxy, imino, N-(C$_{1-6}$ alkyl)imino or —NHC(O)—, with the proviso that p is 2 or more unless B$^1$ is a bond or —NHC(O)—, or any aryl, heteroaryl or heterocyclyl group in a R$^4$ group may be optionally substituted with one or more groups of the Structure (VIB$^1$):

$$-E^1-D^1 \qquad (VIB^1)$$

wherein D$^1$ is aryl, heteroaryl or heterocyclyl and E$^1$ is a bond, C$_{1-6}$ alkylene, oxy-C$_{1-6}$ alkylene, oxy, imino, N-(C$_{1-6}$ alkyl)imino, imino-C$_{1-6}$ alkylene, N-(C$_{1-6}$ alkyl)-iminoC$_{1-6}$ alkylene, C$_{1-6}$ alkylene-oxy-C$_{1-6}$ alkylene, C$_{1-6}$ alkylene-imino-C$_{1-6}$ alkylene, C$_{1-6}$ alkylene-N-(C$_{1-6}$ alkyl)-imino-C$_{1-6}$ alkylene, —NHC(O)—, —NHSO$_2$—, —SO$_2$NH— or —NHC(O)—C$_{1-6}$ alkylene-, and any aryl, heteroaryl or heterocyclyl group in a substituent on R$^4$ may be optionally substituted with one or more groups selected from hydroxy, halo, C$_{1-6}$ alkyl, C$_{1-6}$ alkoxy, carboxy, C$_{1-6}$ alkoxycarbonyl, carbamoyl, N-C$_{1-6}$ alkylcarbamoyl, N-(C$_{1-6}$ alkyl)$_2$ carbamoyl, C$_{2-6}$ alkanoyl, amino, N-C$_{1-6}$ alkylamino and N,N-(C$_{1-6}$ alkyl)$_2$ amino, and any C$_{3-7}$ cycloalkyl or heterocyclyl group in a R$^4$ group may be optionally substituted with one or two oxo or thioxo substituents, and any of the R$^4$ groups defined hereinbefore which comprises a CH$_2$ group which is attached to 2 carbon atoms or a CH$_3$ group which is attached to a carbon atom may optionally be substituted on each said CH$_2$ or CH$_3$ group with a substituent selected from hydroxy, amino, C$_{1-6}$ alkoxy, N-C$_{1-6}$ alkylamino, N,N-(C$_{1-6}$ alkyl)$_2$ amino and heterocyclyl;

R$^5$ is hydrogen, halo, trifluoromethyl, cyano, nitro, amino, hydroxy, C$_{1-6}$ alkyl, C$_{2-6}$ alkenyl, C$_{2-6}$ alkynyl, C$_{1-6}$ alkoxy, N-C$_{1-6}$ alkylamino or N,N-(C$_{1-6}$ alkyl)$_2$amino;

q is 0, 1, 2, 3 or 4.

The compounds of structure (VI) can be made using organic synthesis techniques known to those skilled in the art, as well as by the methods described in International Publication No. WO 00/56738, which is incorporated herein by reference in its entirety (particularly at page 3, line 25 to page 6, line 13). Further, specific examples of these compounds can be found in this publication.

In another embodiment, the JNK inhibitor has the following structure (VII):

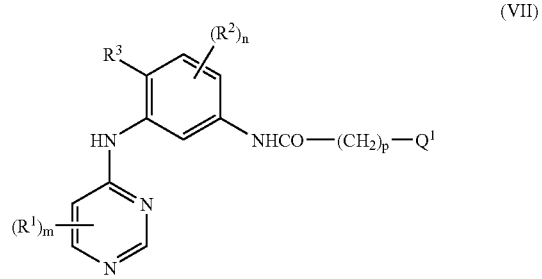

(VII)

wherein m is 0, 1, 2 or 3 and R$^1$ group, which may be the same or different, is selected from hydroxy, halogen, trifluoromethyl, cyano, mercapto, nitro, amino, carboxy, carbamoyl, formyl, sulphamoyl, C$_{1-6}$ alkyl, C$_{1-6}$ alkoxy, C$_{1-6}$ alkylthio, C$_{1-6}$ alkoxycarbonyl, N—C$_{1-6}$ alkylcarbamoyl, N,N-di-(C$_{1-6}$ alkyl)carbamoyl, C$_{2-6}$ alkanoyl, C$_{2-6}$ alkanoyloxy, C$_{2-6}$ alkanoylamino, N—C$_{1-6}$ alkyl-C$_{2-6}$ alkanoylamino, N—C$_{1-6}$ alkylsulphamoyl, N,N-di(C$_{1-6}$ alkyl)sulphamoyl, C$_{1-6}$ alkanesulphonylamino and N—C$_{1-6}$ alkanesulphonylamino, or from a group of the structure:

$$Q^2-X^1-$$

wherein X$^1$ is a direct bond or is selected from O, S, SO, SO$_2$, N(R$^4$), CO, CH(OR$^4$), CON(R$^4$), N(R$^4$)CO, SO$_2$N(R$^4$), N(R$^4$)SO$_2$, OC(R$^4$)$_2$, SC(R$^4$)$_2$, and N(R$^4$)C(R$^4$)$_2$, wherein each R$^4$ is hydrogen or C$_{1-6}$ alkyl, and Q$^2$ is aryl, C$_{1-6}$ alkyl, heteroaryl-C$_{1-6}$ alkyl, heterocyclyl or heterocyclyl-C$_{1-6}$ alkyl, or (R$^1$)$_m$ is C$_{1-3}$ alkylenedioxy, and wherein a single pair of adjacent carbon atoms in a C$_{2-6}$ alkylene chain within a R$^1$ substituent is optionally separated by the insertion of a group selected from O, S, SO, SO$_2$, N(R$^5$), CO, CH(OR$^5$), CON(R$^5$), N(R$^5$)CO, SO$_2$N(R$^5$) and N(R$^5$)SO$_2$ wherein R$^5$ is hydrogen or C$_{1-6}$ alkyl, and wherein any aryl, heteroaryl or heterocyclyl group within a substituent on R$^1$ optionally is substituted with 1,2 or 3 substituents, which may be the same or different, selected from halogeno, trifluoromethyl, cyano, nitro, hydroxy, amino, carboxy, carbamoyl, C$_{1-6}$ alkyl, C$_{1-6}$ alkoxy, C$_{1-6}$ alkylthio, C$_{1-6}$ alkylsulphinyl, C$_{1-6}$ alkylsulphonyl, C$_{1-6}$ alkylamino, di-(C$_{1-6}$ alkyl)amino, C$_{1-6}$ alkoxycarbonyl, N—C$_{1-6}$ alkylcarbamoyl, N,N-di-(C$_{1-6}$ alkyl)carbamoyl, C$_{2-6}$ alkanoyl, C$_{1-6}$ alkanoyloxy, C$_{1-6}$ alkanoylamino, N—C$_{1-6}$ alkyl-C$_{1-6}$ alkanoylamino, N—C$_{1-6}$ alkylsulphamoyl, N,N-di-(C$_{1-6}$ alkyl)sulphamoyl, C$_{1-6}$ alkanesulphonylamino and N—C$_{1-6}$ alkyl-C$_{1-6}$ alkanesulphonylamino, or from a group of the structure:

$$-X^2-Q^3$$

wherein X$^2$ is a direct bond or is selected from O and N(R), wherein R$^7$ is hydrogen or C$_{1-6}$ alkyl, and Q$^3$ is aryl, aryl-C$_{1-6}$ alkyl, heteroaryl, heteroaryl-C$_{1-6}$ alkyl, heterocyclyl or heterocyclyl-C$_{1-6}$ alkyl, and any group optionally is substituted with 1 or 2 substituents, which may be the same or different, selected from halogeno, trifluoromethyl, cyano, hydroxy; amino, C$_{1-6}$ alkyl, C$_{1-6}$ alkoxy, C$_{1-6}$ alkylamino and di-(C$_{1-6}$ alkyl)amino, and wherein any heterocyclyl group within a substituent on R' optionally is substituted with 1 or 2 oxo or thioxo substituents, and wherein any CH$_2$ or CH$_3$ group within a R$^1$ substituent optionally is substituted with on each said CH$_2$ or CH$_3$ group one or more halogeno or C$_{1-6}$ alkyl substituents or a substituent selected from hydroxy, cyano, amino, carboxy, carbamoyl, C$_{1-6}$ alkoxy, C$_{1-6}$ alkylthio, C$_{1-6}$ alkylsulphinyl, C$_{1-6}$ alkylsulphonyl, C$_{1-6}$ alkylamino, di-(C$_{1-6}$ alkyl)amino, C$_{1-6}$ alkoxycarbonyl, N—C$_{1-6}$ alkylcarbamoyl, N,N-di-(C$_{1-6}$ alkyl)carbamoyl, C$_{2-6}$ alkanoyl, C$_{2-6}$ alkanoyloxy, C$_{2-6}$ alkanoylamino, N—C$_{1-6}$ alkyl-C$_{1-6}$ alkanoylamino, N—C$_{1-6}$ alkylsulphamoyl, N,N-di-(C$_{1-6}$ alkyl)sulphamoyl, C$_{1-6}$ alkanesulphonylamino and N—C$_{1-6}$ alkyl-C$_{1-6}$ alkanesulphonylamino;

R$^3$ is hydrogen, halogeno or C$_{1-6}$ alkyl;

n is 0, 1 or 2 and each R$^2$ group, which may be the same or different, is selected from hydroxy, halogeno, trifluoromethyl, cyano, mercapto, nitro, amino, carboxy, C$_{1-6}$ alkoxycarbonyl, C$_{1-6}$ alkyl, C$_{1-6}$ alkoxy, C$_{1-6}$ alkylamino and di-(C$_{1-6}$ alkyl)amino;

p is 0, 1, 2, 3 or 4; and $Q^1$ is aryl or heteroaryl and $Q^1$ is optionally substituted with 1, 2 or 3 substituents, which may be the same or different, selected from hydroxy, halogen, trifluoromethyl, cyano, mercapto, nitro, amino, carboxy, carbamoyl, formyl, $C_{1-6}$ alkyl, $C_{1-6}$ alkoxy, $C_{1-6}$ alkylthio, $C_{1-6}$ alkylsulphinyl, $C_{1-6}$ alkylsulphonyl, $C_{1-6}$ alkylamino, di-($C_{1-6}$ alkyl)amino, $C_{1-6}$ alkoxycarbonyl, N—$C_{1-6}$ alkylcarbamoyl, N,N-di-($C_{1-6}$ alkyl)carbamoyl, $C_{2-6}$ alkanoyl, $C_{1-6}$ alkanoyloxy, $C_{1-6}$ alkanoylamino, N-$C_{1-6}$ alkyl-$C_{2-6}$ alkanoylamino, N—$C_{1-6}$ alkylsulphamoyl, N,N-di-($C_{1-6}$ alkyl)sulphamoyl, $C_{1-6}$ alkanesulphonylamino and N—$C_{1-6}$ alkyl-$C_{1-6}$ alkanesulphonylamino or with a $C_{1-3}$ alkylenedioxy group, or from a group of the structure:

$$-X^3-Q^4$$

wherein $X^3$ is a direct bond or is selected from O and N($R^8$), wherein $R^8$ is hydrogen or $C_{1-6}$ alkyl, and $Q^4$ is aryl, aryl-$C_{1-6}$ alkyl, heteroaryl, heteroaryl-$C_{1-6}$ alkyl, heterocyclyl or heterocyclyl-$C_{1-6}$ alkyl, and any group optionally is substituted with 1 or 2 substituents, which may be the same or different, selected from halogeno, trifluoromethyl, cyano, hydroxy, amino, $C_{1-6}$ alkyl, $C_{1-6}$ alkoxy, $C_{1-6}$ alkylamino and di-($C_{1-6}$ alkyl)amino, and wherein any heterocyclyl group within a substituent on $Q^1$ optionally is substituted with 1 or 2 oxo or thioxo substituents, and wherein a single pair of adjacent carbon atoms in a $C_{2-6}$ alkylene chain within a $Q^1$ substituent is optionally separated by the insertion of a group selected from O, S, SO, $SO_2$, N($R^9$), CO, CH(O$R^9$), CON($R^9$), N($R^9$)CO, $SO_2$N($R^9$) and N($R^9$)$SO_2$ wherein $R^9$ is hydrogen or $C_{1-6}$ alkyl, and wherein any $CH_2$ or $CH_3$ group within a group optionally is substituted on each said $CR_2$ or $CH_3$ group with one or more halogen or $C_{1-6}$ alkyl substituents or a substituent selected from hydroxy, cyano, amino, carboxy, carbamoyl, $C_{1-6}$ alkoxy, $C_{1-6}$ alkylthio, $C_{1-6}$ alkylsulphinyl, $C_{1-6}$ alkylsulphonyl, $C_{1-6}$ alkylamino, di-($C_{1-6}$ alkyl)amino, $C_{1-6}$ alkoxycarbonyl, N-$C_{1-6}$ alkylcarbamoyl, N,N-di-($C_{1-6}$ alkyl) carbamoyl, $C_{1-6}$ alkanoyl, $C_{1-6}$ alkanoyloxy, $C_{1-6}$ alkanoylamino, N-$C_{1-6}$ alkyl-$C_{1-6}$ alkanoylamino N-$C_{1-6}$ alkylsulphamoyl, N,N-di-($C_{1-6}$ alkyl)sulphamoyl, $C_{1-6}$ alkanesulphonylamino and N-$C_{1-6}$ alkyl-$C_{1-6}$ alkanesulphonylamino.

The compounds of structure (VII) can be made using organic synthesis techniques known to those skilled in the art, as well as by the methods described in International Publication No. WO 01/27089, which is incorporated herein by reference in its entirety (particularly at page 3, line 7 to page 5, line 29). Further, specific examples of these compounds can be found in this publication.

In another embodiment, the JNK inhibitor has the following structure (VIII):

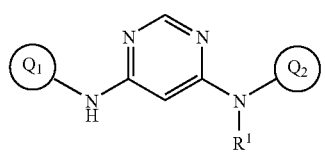

(VIII)

wherein:

$R^1$ is selected from $C_{1-6}$ alkyl (optionally substituted by one or two substituents independently selected from halo, amino, $C_{1-4}$ alkylamino, di-($C_{1-4}$ alkyl)amino, hydroxy, cyano, $C_{1-4}$ alkoxy, $C_{1-4}$ alkoxycarbonyl, carbamoyl, —NHCO $C_{1-4}$ alkyl, trifluoromethyl, phenylthio, phenoxy, pyridyl, morpholino), benzyl, 2-phenylethyl, $C_{3-5}$ alkenyl (optionally substituted by up to three halo substituents, or by one trifluoromethyl substituent, or one phenyl substituent), N-phthalimido-$C_{1-4}$ alkyl, $C_{3-5}$ alkynyl (optionally substituted by one phenyl substituent) and $C_{3-6}$ cycloalkyl-$C_{1-6}$ alkyl;

wherein any phenyl or benzyl group of $R^1$ is optionally substituted by up to three substituents independently selected from halogeno, hydroxy, nitro, amino, $C_{1-3}$ alkylamino, di-($C_{1-3}$ alkyl)amino, cyano, trifluoromethyl, $C_{1-3}$ alkyl (optionally substituted by 1 or 2 substituents independently selected from halogeno, cyano, amino, $C_{1-3}$ alkylamino, di-($C_{1-3}$ alkyl)amino, hydroxy and trifluoromethyl), $C_{1-3}$ alkenyl (optionally substituted by up to three halo substituents, or by one trifluoromethyl substituent), $C_{1-3}$ alkynyl, $C_{1-3}$ alkoxy, —SH, —S—$C_{1-3}$ alkyl, carboxy, $C_{1-3}$ alkoxycarbonyl;

$Q_1$ and $Q_2$ are independently selected from phenyl, naphthyl, indanyl and 1,2,3,4-tetrahydronaphthyl;

and one or both of $Q_1$ and $Q_2$ is substituted on any available carbon atom with one substituent of the structure (VIIIa) and $Q_2$ may optionally be substituted on any available carbon atom with further substituents of the structure (VIIIa):

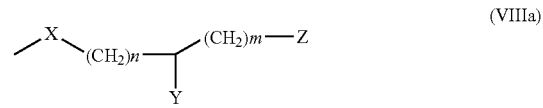

(VIIIa)

(provided that when present in $Q_1$ the substituent of structure (VIIIa) is not adjacent to the —NH-link);

wherein:

X is $CH_2$, O, S, NH or NRx (wherein Rx is $C_{1-4}$ alkyl, optionally substituted by one substituent selected from halo, amino, cyano, $C_{1-4}$ alkoxy or hydroxy);

Y is H or as defined for Z;

Z is OH, SH, NH2, $C_{1-4}$ alkoxy, $C_{1-4}$ alkylthio, —NH $C_{1-4}$ alkyl, —N($C_{1-4}$ alkyl)$_2$, —NH—$C_{3-8}$ cycloalkyl, pyrrolidin-1-yl, piperidin-1-yl, piperazin-1-yl (optionally substituted in the 4-position by $C_{1-4}$ alkyl or $C_{1-4}$ alkanoyl), morpholino or thiomorpholino;

n is 1, 2 or 3;

m is 1, 2 or 3;

and $Q_1$ and $Q_2$ may each optionally and independently be substituted on any available carbon atom with up to four substituents independently selected from halogeno, hydroxy, thio, nitro, carboxy, cyano, $C_{2-4}$ alkenyl (optionally substituted by up to three halo substituents, or by one trifluoromethyl substituent), $C_{2-4}$ alkynyl, $C_{1-5}$ alkanoyl, $C_{1-4}$ alkoxycarbonyl, $C_{1-6}$ alkyl, hydroxy-$C_{1-6}$ alkyl, fluoro-$C_{1-4}$ alkyl, amino-$C_{1-3}$ alkyl, $C_{2-4}$ alkanoyloxy-$C_{1-4}$-alkyl, $C_{1-4}$ alkoxy-$C_{1-3}$ alkyl, carboxy-$C_{1-4}$ alkyl, $C_{1-4}$ alkoxycarbonyl-$C_{1-4}$ alkyl, carbamoyl-$C_{1-4}$ alkyl, N—$C_{1-4}$ alkylcarbamoyl-$C_{1-4}$ alkyl, N,N-di-($C_{1-4}$ alkyl)-carbamoyl-$C_{1-4}$ alkyl, pyrrolidin-1-yl-$C_{1-3}$ alkyl, piperidin-1-yl-$C_{1-3}$ alkyl, piperazin-1-yl-$C_{1-3}$ alkyl, morpholino-$C_{1-3}$ alkyl, thiomorpholino-$C_{1-3}$ alkyl, piperazin-1-yl, morpholino, thiomorpholino, $C_{1-4}$ alkoxy, cyano-$C_{1-4}$ alkoxy, carbamoyl-$C_{1-4}$ alkoxy, N—$C_{1-4}$ alkylcarbamoyl-$C_{1-4}$ alkoxy, N,N-di-($C_{1-4}$ alkyl)-carbamoyl $C_{1-4}$ alkoxy 2-aminoethoxy, 2-$C_{1-4}$ alkylaminoethoxy, 2-di-($C_{1-4}$ alkyl)aminoethoxy, $C_{1-4}$ alkoxycarbonyl-$C_{1-4}$ alkoxy, halogeno-$C_{1-4}$ alkoxy, 2-hydroxyethoxy, $C_{2-4}$ alkanoyloxy-$C_{2-4}$ alkoxy, 2-$C_{1-4}$ alkoxyethoxy, carboxy-$C_{1-4}$ alkoxy, $C_{3-5}$ alkenyloxy, $C_{3-5}$ alkynyloxy, $C_{1-4}$ alkylthio, $C_{1-4}$ alkylsulphinyl, $C_{1-4}$alkylsulphonyl, hydroxy-$C_{2-4}$ alkylthio, hydroxy-$C_{2-4}$ alkylsulphinyl, hydroxy $C_{2-4}$ alkylsulphonyl, ureido ($H_2N$—CO—NH—), $C_{1-4}$ alkylNH—CO—NH—, di-($C_{1-4}$ alkyl)-N—CO—NH—, $C_{1-4}$ alkyNH—CO—N($C_{1-4}$ alkyl), di-($C_{1-4}$ alkyl)N—CO—N($C_{1-4}$ alkyl)-, carbamoyl, N-($C_{1-4}$ alkyl)carbamoyl, N,N-di-($C_{1-4}$ alkyl)carbamoyl, amino, $C_{1-4}$ alkylamino, di-($C_{1-4}$ alkyl)amino, $C_{2-4}$ alkanoylamino, and also independently, or where appropriate in addition to, the above optional substituents, $Q_1$ and/or $Q_2$ may optionally be substituted on any available carbon atom with up to two further substituents independently selected from $C_{3-8}$ cycloalkyl, phenyl-$C_{1-4}$ alkyl, phenyl-$C_{1-4}$ alkoxy, phenylthio, phenyl, naphthyl, benzoyl, phenoxy, benzimidazol-2-yl and a 5- or 6-membered aromatic heterocycle (linked via a ring carbon atom and containing one to three heteroatoms independently selected from oxygen, sulphur and nitrogen); wherein said naphthyl, phenyl, benzoyl, 5- or 6-membered aromatic heterocyclic substituents and the phenyl group in said phenyl-$C_{1-4}$ alkyl, phenylthio, phenoxy and phenyl-$C_{1-4}$ alkoxy substituents may optionally be substituted with up to five substituents independently selected from halogeno, $C_{1-4}$ alkyl and $C_{1-4}$ alkoxy.

The compounds of structure (VIII) can be made using organic synthesis techniques known to those skilled in the art, as well as by the methods described in International Publication No. WO 00/12468, which is incorporated herein by reference in its entirety (particularly at page 2, line 10 to page 4, line 14). Further, specific examples of these compounds can be found in this publication.

In another embodiment, the JNK inhibitor has the following structure (IX):

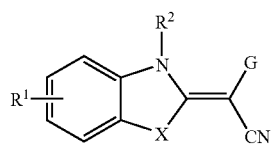

(IX)

wherein:

X is O, S or $NR^0$, with $R^0$ being H or an unsubstituted or substituted $C_1$-$C_6$ alkyl;

G is an unsubstituted or substituted pyrimidinyl group;

$R^1$ is selected from the group comprising or consisting of hydrogen, unsubstituted or substituted $C_1$-$C_6$-alkoxy, unsubstituted or substituted $C_1$-$C_6$-thioalkoxy, unsubstituted or substituted $C_1$-$C_6$-alkyl, unsubstituted or substituted $C_2$-$C_6$-alkenyl, unsubstituted or substituted $C_2$-$C_6$-alkynyl, primary, secondary or tertiary amino groups, aminoacyl, aminocarbonyl, unsubstituted or substituted $C_1$-$C_6$ alkoxycarbonyl, unsubstituted or substituted aryl, unsubstituted or substituted heteroaryl, carboxyl, cyano, halogen, hydroxy, nitro, sulfoxy, sulfonyl, sulfonamide, unsubstituted or substituted hydrazides;

$R^2$ is selected from the group comprising or consisting of hydrogen, unsubstituted or substituted $C_1$-$C_6$-alkyl, unsubstituted or substituted $C_2$-$C_6$-alkenyl, unsubstituted or substituted $C_2$-$C_6$-alkynyl, unsubstituted or substituted $C_1$-$C_6$-alkyl-aryl, unsubstituted or substituted aryl or heteroaryl, unsubstituted or substituted $C_1$-$C_6$-alkyl-heteroaryl, —C(O)—$OR^3$, —C(O)—$R^3$, —C(O)—$NR^3R^{3'}$, —($SO_2$)$R^3$, with $R^3$ and $R^{3'}$ being independently selected from the group comprising or consisting of hydrogen, unsubstituted or substituted $C_1$-$C_6$ alkyl, unsubstituted or substituted $C_2$-$C_6$ alkenyl, unsubstituted or substituted $C_2$-$C_6$ alkynyl, unsubstituted or substituted aryl, unsubstituted or substituted heteroaryl, unsubstituted or substituted $C_1$-$C_6$-alkyl aryl, unsubstituted or substituted $C_1$-$C_6$-alkyl heteroaryl.

The compounds of structure (IX) can be made using organic synthesis techniques known to those skilled in the art, as well as by the methods described in European Patent Publication 1 110 957, filed Dec. 24, 1999 which is incorporated herein by reference in its entirety (particularly at page 19, line 52 to page 21, line 9). Further, specific examples of these compounds can be found in this publication.

In another embodiment, the JNK inhibitor has the following structure (X):

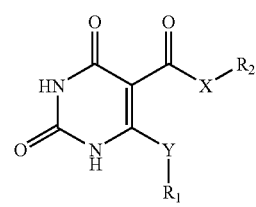

(X)

wherein:

Y is from O, NH, N(R), S, S(O) or $S(O)_2$.

X is from O, NH, or N(R).

$R_1$ and $R_2$ are each independently selected from H, a $C_1$-$C_6$ straight chain or branched alkyl or alkenyl group, optionally substituted with one to four substituents, each of which is independently selected from $NH_2$, NHR, $N(R)_2$, $NO_2$, OH, OR, $CF_3$, halo, CN, $CO_2H$, $CONH_2$, CONHR, $CON(R)_2$, COR, SR, S(O)R, $S(O)_2R$, $S(O)_2NH_2$, $S(O)_2$NHR or R; a 5-7 membered aromatic or non-aromatic carbocyclic or heterocyclic ring, optionally substituted with one to four substituents, each of which is independently selected from $NH_2$, NHR, $N(R)_2$, $NO_2$, OH, OR, $CF_3$, halo, CN, $CO_2H$, $CONH_2$, CONHR, $CON(R)_2$, COR, SR, S(O)R, $S(O)_2R$, $S(O)_2NH_2$, $S(O)_2$NHR or R; or a 9-10 membered bicyclic aromatic or non-aromatic carbocyclic or heterocyclic ring optionally substituted with one to four substituents, each of which is independently selected from $NH_2$, NHR, $N(R)_2$, $NO_2$, OH, OR, $CF_3$, halo, CN, $CO_2H$, $CONH_2$, CONHR, $CON(R)_2$, COR, SR, S(O)R, $S(O)_2R$, $S(O)_2NH_2$, $S(O)_2NH_2$, $S(O)_2$NHR or R.

The compounds of structure (X) can be made using organic synthesis techniques known to those skilled in the art, as well as by the methods described in International Publication No. WO 00/75118, which is incorporated herein by reference in its entirety (particularly at page 8, line 10 to page 11, line 26). Further, specific examples of these compounds can be found in this publication.

In another embodiment, the JNK inhibitor has the following structure (XI):

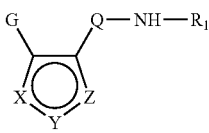

wherein:

X—Y—Z is selected from one of the following:

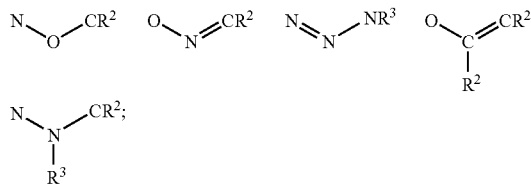

$R^1$ is H, $CONH_2$, $T_{(n)}$-R, or $T_{(n)}$-$Ar^2$;

R is an aliphatic or substituted aliphatic group;

n is zero or one;

T is C(=O), $CO_2$, CONH, $S(O)_2$, $S(O)_2NH$, $COCH_2$, or $CH_2$;

each $R^2$ is independently selected from hydrogen, —R, —$CH_2OR$, —$CH_2OH$, —CH=O, —$CH_2SR$, —$CH_2(O)_2R$, —$CH_2(C=O)R$, —$CH_2CO_2R$, —$CH_2CO_2H$, —$CH_2CN$, —$CH_2NHR$, —$CH_2N(R)_2$, —CH=N—OR, —CH=NNHR, —CH=NN(R)$_2$, —CH=NNHCOR, —CH=NNHCO$_2$R, —CH=NNHSO$_2$R, -aryl, -substituted aryl, —$CH_2$(aryl), —$CH_2$(substituted aryl), —$CH_2NH_2$, —$CH_2NHCOR$, —$CH_2NHCONHR$, —$CH_2NHCON(R)_2$, —$CH_2NHCOR$, —$CH_2NHCO_2R$, —$CH_2CONHR$, —$CH_2CON(R)_2$, —$CH_2SO_2NH_2$, —$CH_2$(heterocyclyl), —$CH_2$ (substituted heterocyclyl), -(heterocyclyl), or -(substituted heterocyclyl);

each $R^3$ is independently selected from hydrogen, R, COR, $CO_2R$, or $S(O)_2R$;

G is R or $Ar^1$;

$Ar^1$ is aryl, substituted aryl, aralkyl, substituted aralkyl, heterocyclyl, or substituted heterocyclyl, wherein $Ar^1$ is optionally fused to a partially unsaturated or fully unsaturated five to seven membered ring containing zero to three heteroatoms;

Q-NH is

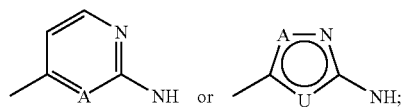

wherein the H of Q-NH is optionally replaced by $R^3$;

A or N or $CR^3$;

U is $CR^3$, O, S, or $NR^3$;

$Ar^2$ is aryl, substituted aryl, heterocyclyl or substituted heterocyclyl, wherein $Ar^2$ is optionally fused to a partially unsaturated or fully unsaturated five to seven membered ring containing zero to three heteroatoms; and wherein each substitutable carbon atom is $Ar^2$, including the fused ring when present, is optionally and independently substituted by halo, R, OR, SR, OH, $NO_2$, CN, $NH_2$, NHR, $N(R)_2$, NHCOR, NHCONHR, NHCON(R)$_2$, NRCOR, NHCO$_2$R, CO$_2$R, CO$_2$H, COR, CONHR, CON(R)$_2$, S(O)$_2$R, SONH$_2$, S(O)R, SO$_2$NHR, or NHS(O)$_2$R, and wherein each saturated carbon in the fused ring is further optionally and independently substituted by =O, =S, =NNHR, =NNR$_2$, =N—OR, =NNHCOR, =NNHCO$_2$R, =NNHSO$_2$R, =NNHSO$_2$R, or =NR;

wherein each substitutable nitrogen atom in $A^2$ is optionally substituted by R, COR, $S(O)_2R$, or $CO_2R$.

The compounds of structure (XI) can be made using organic synthesis techniques known to those skilled in the art, as well as by the methods described in International Publication No. WO 01/12621, which is incorporated herein by reference in its entirety (particularly at page 8, line 10 to page 10, line 7). Further, specific examples of these compounds can be found in this publication.

In another embodiment, the JNK inhibitor has the following structure (XII) or (XIII):

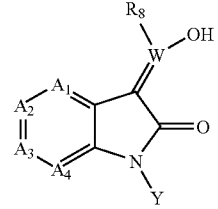

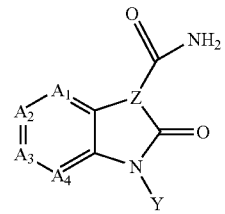

wherein:

Y is —(CH$_2$)-Q$_1$; —(CO)-Q$_1$; —(CO)NH-Q$_1$; —(CO)—O-Q$_1$; —(SO$_2$)-Q$_1$ or —(SO$_2$)NH-Q$_1$;

$Q_1$ is a $C_1$-$C_6$ straight chain or branched alkyl or alkenyl group; a 5-7 membered aromatic or non-aromatic carbocyclic or heterocyclic ring; or a 9-14 membered bicyclic or tricyclic aromatic or non-aromatic carbocyclic or heterocyclic ring system, wherein said alkyl, alkenyl, ring or ring system is optionally substituted with one to four substituents, each of which is independently selected from NH$_2$, NH—R, N(R)$_2$, NO$_2$, OH, OR, CF$_3$, halo, CN, CO$_2$H, C(O)—NH$_2$, C(O)—NH—R, C(O)—N(R)$_2$, C(O)—R, SR, S(O)—R, S(O)$_2$—R, S(O)$_2$—NH—R or —R, the heterocyclic ring system and heterocyclic ring containing 1 to 4 heteroatoms, which are independently selected from N, O, S, SO and SO$_2$;

W is N or C, when W is N, $R_8$ is a lone pair of electrons, when W is C, $R_8$ is $R_7$;

$A_1$ is N or $CR^1$;

$A_2$ is N or $CR^2$;

$A_3$ is N or $CR^3$;

$A_4$ is N or $CR^4$;

provided that at least one of $A_1$, $A_2$, $A_3$ and $A_4$ must not be N;

$R^1$ is —NHR$^5$, —OR$^5$, —SR$^5$, or —R$^5$;

$R^2$, $R^3$, and $R^4$ are independently selected from —(CO)NH$_2$, —(CO)NHR, —(CO)N(R)$_2$, —NHR$^5$, —NHCH$_2$R$^5$, —OR$^5$, —SR$^5$, —R$^5$, —NH(CO)—R$^6$, —NH(CO)—

$NHR^6$, $-NH(CO)-NH(CO)R^6$, $-NH(CO)-OR^6$, $-NH(SO_2)-R^6$, $-NH(SO_2)-NHR^6$, $-C(O)OH$, $-C(O)OR$, $-(CO)-Q_1$, $-(CO)\ NH-Q_1$, $-(CO)NR-Q_1$, $-(CO)-O-Q_1$, $-(SO_2)-Q_1$ or $-(SO_2)NH-Q_1$;

$R^5$ and $R^6$ are each independently selected from H; $N(R)_2$, NHOH, $NO_2$, C(O)OR or halo; a $C_1$-$C_6$ straight chain or branched alkyl, alkenyl or alkynyl group; a 5-7 membered aromatic or non-aromatic carbocyclic or heterocyclic ring; or a 9-14 membered bicyclic or tricyclic aromatic or non-aromatic carbocyclic or heterocyclic ring, wherein said alkyl, alkenyl, ring or ring system is optionally substituted with one to four substituents, each of which is independently selected from $NH_2$, NHR, NHC(O)OR, $N(R)_2$, $NO_2$, OH, OR, $CF_3$, halo, CN, $Si(R)_3$, $CO_2H$, COOR, $CONH_2$, CONHR, $CON(R)_2$, COR, SR, S(O)R, $S(O)_2R$, $S(O)_2NHR$ or R;

$R^7$ is H; a $C_1$-$C_6$ straight chain or branched alkyl or alkenyl group; a 5-7 membered aromatic or non-aromatic carbocyclic or heterocyclic ring; or a 9-14 membered bicyclic or tricyclic aromatic or non-aromatic carbocyclic or heterocyclic ring; wherein said alkyl, alkenyl, ring or ring system is optionally substituted with one to four substituents, each of which is independently selected from $NH_2$, NHR, $N(R)_2$, $NO_2$, OH, OR, $CF_3$, halo, CN, $CO_2H$, $CONH_2$, CONHR, $CON(R)_2$, COR, SR, S(O)R, $S(O)_2R$, $S(O)_2NHR$ or R;

R is a $C_1$-$C_6$ straight chain or branched alkyl or alkenyl group, a 5-7 membered aromatic or non-aromatic carbocyclic or heterocyclic ring, or a 9-10 membered bicyclic aromatic or non-aromatic carbocyclic or heterocyclic ring system; and Z is CH or N.

The compounds of structure (XII) and structure (XIII) can be made using organic synthesis techniques known to those skilled in the art, as well as by the methods described in International Publication No. WO 00/64872, which is incorporated herein by reference in its entirety (particularly at page 9, line 1 to page, 106, line 2). Further, specific examples of these compounds can be found in this publication.

In another embodiment, the JNK inhibitor has the following structure (XIV):

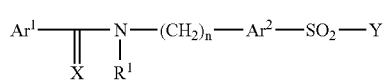

(XIV)

wherein:

$Ar^1$ and $Ar^2$ are independently from each other aryl or heteroaryl,

X is O or S;

$R^1$ is hydrogen or a $C_1$-$C_6$-alkyl group, or $R^1$ forms a 5-6-membered saturated or unsaturated ring with $Ar^1$;

n is an integer from 0 to 5;

Y is an optionally substituted 4-12-membered saturated cyclic or bicyclic alkyl containing a nitrogen, which forms a bond with the sulfonyl group of formula XIV.

The compounds of structure (XIV) can be made using organic synthesis techniques known to those skilled in the art, as well as by the methods described in International Publication No. WO 01/23378, published Apr. 5, 2001, which is incorporated herein by reference in its entirety (particularly at page 90, line 1 to page 91, line 11). Further, specific examples of these compounds are found in said publication.

In another embodiment, the JNK inhibitor has the following structure (XV):

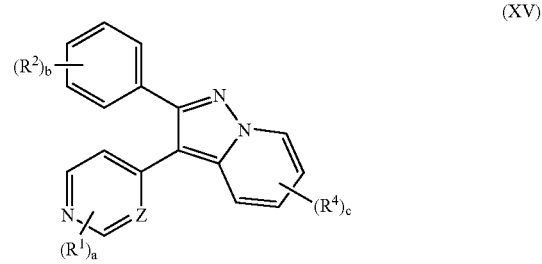

(XV)

wherein:

Z is CH or N;

a is 1 or 2;

b is 1, 2 or 3;

c is 1, 2 or 3;

each $R^1$ is independently selected from groups of the formula:

$$-(X)_d-(CH_2)_e-R^5$$

wherein:

d is 0 or 1;

e is 0 to 6;

X is O, $NR^6$ or $S(O)_f$ where f is 0, 1 or 2;

$R^5$ is hydrogen, halogen, $C_{1-6}$alkyl, $C_{2-6}$alkenyl, $C_{2-6}$alkynyl, $C_{3-12}$cycloalkyl, heterocyclyl, aryl, heteroaryl, hydroxyl, cyano, nitro, trihalomethyl, $NR^7R^8$, $C_6H_4NR^7R^8$, $C_6H_4(CH_2)NR^7R^8$, $C(O)R^7$, $C(O)NR^7R^8$, $OC(O)R^7$, $OC(O)NR^7R^8$, $CO_2R^7$, $OCO_2R^7$, $SO_2R^7$, $SO_2NR^7R^8$, $C(=NR^7)NR^7R^8$, $NR^7(C=NR^7)NR^7R^8$, $NHC(O)R^7$ or $N(C_{1-3}alkyl)C(O)R^7$;

$R^2$ is independently selected from hydrogen, cyano, halogen, trihalomethyl, $OC_{1-6}$alkyl, $C_{1-6}$alkyl, $C_{2-6}$alkenyl, $C_{2-6}$alkynyl, $S(O)_gC_{1-6}$alkyl where g is 0, 1 or 2, $NC_6$alkyl ($C_{1-6}$alkyl), hydroxyl or nitro;

each $R^4$ is independently selected from groups of the formula $$-(Y)_d-(CH_2)_e-R^3$$

wherein:

d is 0 or 1;

e is 0 to 6;

Y is O or $S(O)_f$ where f is 0, 1 or 2;

$R^3$ is hydrogen, halogen, $C_{1-6}$alkyl, $C_2$alkenyl, $C_{2-6}$alkynyl, $C_{3-12}$cycloalkyl, heterocyclyl, aryl, heteroaryl, hydroxyl, cyano, nitro, trihalomethyl, phthalamido, $C_6H_4NR^7R^8$, $C_6H_4(CH_2)NR^7R^8$, $C(O)R^7$, $C(O)NR^7R^8$, $OC(O)R^7$, $OC(O)NR^7R^8$, $CO_2R^7$, $OCO_2R^7$, $SO_2R^7$, $SO_2NR^7R^8$ or $C(=NR^7)NR^7R^8$;

$R^6$ is H, $C_{1-6}$alkyl, $C_{2-6}$alkenyl, aryl, heteroaryl, $C_{3-12}$cycloalkyl, or heterocyclyl;

$R^7$ and $R^8$ are each independently H, $C_{1-8}$alkyl, $C_{2-6}$alkenyl, $SO_2C_{1-6}$alkyl, $(CH_2)_m-C_{3-12}$cycloalkyl, $(CH_2)_m$-aryl, $(CH_2)m$heterocyclyl, $(CH_2)m$heteroaryl, wherein m=0, 1 or 2, or may, together with the nitrogen atom to which they are bound, form a heterocyclyl group; and wherein any of said alkyl, alkenyl and alkynyl groups may be optionally substituted with up to three members selected from halogen, hydroxyl, oxo, cyano, $NR^7R^8$, $C_{1-6}$alkyl, $OC_{1-6}$alkyl, $S(O)C_{1-6}$alkyl, $S(O)_2C_{1-6}$alkyl and $SO_2NR^7R^8$; and wherein any of said cycloalkyl, heterocyclyl, aryl, and heteroaryl groups may be optionally substituted with substituents selected from a group consisting of $C_{1-6}$alkyl, $C_{1-6}$alkoxy, $C_{1-6}$alkylsulfenyl, $C_{1-6}$alkylsulfinyl, $C_{1-6}$alkylsulfonyl, hydroxy, oxo, mercapto, nitro, cyano, halogen, $C_{1-6}$perfluoroalkyl, amino optionally substituted by $C_{1-6}$alkyl, carbamoyl optionally substituted by $C_{1-6}$alkyl, $NR^7R^8$, carboxy and aminosulfonyl optionally substituted by $C_{1-6}$alkyl.

The compounds of structure (XV) can be made using organic synthesis techniques known to those skilled in the art, as well as by the methods described in International Publication No. WO 02/16359, published Feb. 28, 2002, which is incorporated herein by reference in its entirety (particularly at page 163, line 1 to page 164, line 25). Further, specific examples of these compounds are found in said application and publication.

In another embodiment, the JNK inhibitor is:

2-(4-Cyanophenyl)-4-(4-fluorophenyl)-5(4 pyridyl)-1H-imidazole;

1-Methyl-2-(4-methoxyphenyl)-4-phenyl-5-(4-pyridyl)-imidazole;

2-(4-Cyanophenyl)-1-methyl-4-phenyl-5(4-pyridyl)-imidazole;

2-(4-Aminomethylphenyl)-1-methyl-4-phenyl-5-(4-pyridyl)-imidazole;

4-[1-Methyl-4-phenyl-5(4-pyridyl)-imidazol-2-yl]benzoic acid, sodium salt;

2-(4-Acetamidomethyphenyl)-1-methyl-4-phenyl-5(4-pyridyl)imidazole;

Methyl-4-[-methyl-4-phenyl-5-(4-pyridyl)imidazol-2-yl]benzoate;

4-(4-Fluorophenyl)-N-1-hydroxy-2-(4-hydroxyphenyl)-5-(4-pyridyl)imidazole;

4-(4-Fluorophenyl)-2-(4-hydroxyphenyl)-5-(4-pyridyl)-1H-imidazole;

4-[4-(4-Fluorophenyl)-5-(4-pyridyl)-1H-imidazol-2-yl]benzoic acid;

2-(4-Cyanophenyl)-4-(4-fluorophenyl)-1-N-hydroxy-5-(4-pyridyl)imidazole;

2-(4-Aminomethylphenyl)-4-(4-fluorophenyl)-5-(4-pyridyl)-1H-imidazole;

2-(4-Cyanophenyl)-4-(4-fluorophenyl)-N-1-hydroxy-5-(4-quinolyl)imidazole;

2-(4-Cyanophenyl)-4-(4-fluoropbenyl)-5-(4-quinolyl)-1H-imidazole;

2-(3,5-Dibromo-4-hydroxyphenyl)-4-(4-fluorophenyl)-5-(4-pyridyl)-1H-imidazole;

Ethyl 4-[4-(4-Fluorophenyl)-5-(4-pyridyly]-1H-ijmidazol-2-yl]-benzoate;

2-[3,5-Dimethyl-4-hydroxy (phenyl)]-4-(4-fluorophenyl)-5-(4-pyridyl)-1H-imidazole;

4-(4-Fluorophenyl 2-(2-hydroxyphenyl)-5-(4-pyridyl)-1H-imidazole;

4-(4-Fluorophenyl)-2-(4-methylthiophenyl)-5-(4-pyridyl)-1H-imidazole;

Methyl 4-[4-(4-fluorophenyl)-5-(4-pyridyl)-1H-imidazol-2-yl]-benzoate;

4-(4-Fluorophenyl)-2-(4-methylsulfonylphenyl)-5-(4-pyridyl)-1H-imidazole;

4-(4-Fluorophenyl)-2-(4-methylsulfinylphenyl)-5-(4-pyridyl)-1H-imidazole;

N,N-Dimethyl-4-[4-(4-fluorophenyl-5-(4-pyridyl)-1H-imidazol-2-yl]-benzamine;

2-[(4-N,N-Dimethyl)aminomethylphenyl]-4-(4-fluorophenyl)-5-(4-pyridyl)-1H-imidazole;

2-[4-(Dimethylamino)phenyl]-4(4-fluorophenyl)-5-(4-pyridyl)-1H-imidazole;

4-(4-Fluorophenyl)-2-phenyl-5-(4-pyridyl)-1H-imidazole;

2-[4-(3-Dimethyl aminopropoxy)phenyl]-4(4-fluorophenyl)-5-(4-pyridyl)-1H-imidazol;

4-(4-Fluorophenyl)-2-(4-nitrophenyl)-5-(4-pyridyl)-1H-imidazole;

N,N-Dimethyl-4-[2-(4-fluorophenyl)-5-(4-pyridyl)-1H-imidazol-2-yl]-benzoyloxyacetamide;

2-(4-Aminophenyl)-4-(4-fluorophenyl)-5-(4-pyridyl)-1H-imidazole;

4-(4-Fluorophenyl)-2-(4-methanesulfonamidophenyl)-5-(4-pyridyl)-1H-imidazole;

4-[4-(4-Fluorophenyl)-5-(4-pyridyl)-1H-imidazo 1-2-yl] phenyl-sulfonamide;

N'-Cyano-N-4-[4-(fluorophenyl)-5-(4-pyridyl)-1H-imidazol-2-yl]benzylguanidine;

2-[4-(Methanesulfonamido)methytpheny]-4(4-fluorophenyl)-5-(4-pyridyl)-1H-imidazole;

4-(4-Fluorophenyl)-2-(4-methoxyphenyl)-5(4 pyridyl)-1H-imidazole;

2-(4-Amino-3-iodophenyl)-4-(4-fluorophenyl)-5-(4-pyridyl)-1H-imidazole;

N-Benzyl-N-methyl-4-[4-(4-fluorophenyl-5-(4-pyridyl)-1H-imidazol-2-yl]benzamide;

2-[4-(N-Benzyl-N-methyl)aminomethyphenyl]-4-(4-fluorophenyl)-5-(4-pyridyl)-1H-imidazole;

4-(4-Fluorophenyl)-N-1-hydroxy-2-(4-methylthiophenyl)-5-(4-quinolyl)imidazole;

4-(4-Fluorophenyl)-2-(4-methylthiophenyl)-5(4-quinolyl)-1H-imidazole;

4-(4-Fluorophenyl)-2-(4-methylsulfinylphenyl)-5-(4-quinolyl)-1H-imidazole;

4-(3-Chlorophenyl)-2-(4-methytsulfinylphenyl)-5-(4-pyridyl)-1H-imidazole;

4-(3-Chlorophenyl)-N-1-hydroxy-2-(4-methylthiophenyl)-5-(4-pyridyl)-1H-imidazole;

4-(3-Chlorophenyl)-2-(4-methylthiophenyl)-5-(4-pyridyl)-1H-imidazole;

4-(4-Fluorophenyl)-2-(4-formamidomethylphenyl)-5-(4-pyridyl)-1H-imidazole;

4-[4-(4-Fluorophenyl)-5-(4-pyridyl)-1H-imidazol-2-yl]-benzohydroxamic acid;

O-Benzyl-4-[4-(4-Flurophenyl)-5-(4-pyridyl)-1H-imidazol-2-yl)-benzohydroxamic acid;

4-[4-(4-Fluorophenyl)-5-(4-pyridyl)-1H-imidazol-2-yl] benzamidoxime;

N'-Methyl-N'-cyano-N-[4(4-fluorophenyl)-5-(4-pyridyl)-1H-imidazol-2-yl]-benzylguanidine;

N-1-Hydroxy-4-(3-methoxyphenyl)-2-(4-methylthiophenyl)-5-(4-pyridyl)-1H-imidazole;

4-(3-ethoxyphenyl)-2-(4-methylthiophenyl)-5-(4-pyridyl)imidazole;

4-(3-Methoxyphenyl)-2-(4-methylsulfinylphenyl)-5-(4-pyridyl)-1H-imidazole;

Morpholino-4-[4-(4-fluorophenyl)-5-(4-pyridyl)-1H-imidazol-2-yl]benzamide;

4-(4-Fluorophenyl)-5-[4-(2-methylpyridyl)-2-(4-methylthiophenyl)-1H-imidazole;

4-(4-Fluorophenyl)-5-[4-(2-methylpyridyl)-2-(4-methylsulfinylphenyl)-1H-imidazole;

4-(4-Fluorophenyl)-N-1-hydroxy-5-(4-pyrimidinyl)-imidazole;

4-(4-Fluorophenyl)-2-(4-methylthiophenyl)-5-(4-pyrimidinyl)-1H-imidazole;

4-(4-Fluorophenyl)-2-(4-methylsulfinylphenyl)-5-(4-pyrimidinyl)-1H-imidazole;

4-(4-Fluorophenyl)-2-(4-methylsulfonylphenyl)-5-(4-pyrimidinyl)-1H-imidazole;

4-(4-Fluorophenyl)-2-(4-Morpholinomethylphenyl)-5-(4-pyridyl)-1H-imidazole;

4-(4-Fluorophenyl)-2-(4-hydroxymethyl)-5-(4-pyridyl)-1H-imidazole;

4-[4-(4-Fluorophenyl)-5-(4-pyridyl)-1H-imidazol-2-yl]-benzaldehyde;

4-(2-Methoxyphenyl)-2-(4-methylsulfinylphenyl)-5-(4-pyridyl)-1H-imidazole;

N-1-Hydroxy-4-(2-methoxyphenyl)-2-(4-methylthiophenyl)-5-(4-pyridyl)imidazole;

4-(2-Methoxyphenyl)-2-(4-methylthiophenyl)-5-(4-pyridyl)-1H-imidazole;

3-[4-(4-Fluorophenyl)-5-(4-pyridyl)-1H-imidazol-2-yl]phenyl-5-methyl-4,5-dihydro-1,2,4-oxadiazole;

3-[4-(4-Fluorophenyl)-5-(4-pyridyl)-1H-imidazol-2-yl]phenyl-5-methyl-1,2,4-oxadiazole;

4-(3-Aminophenyl)-2-(4-methylthiophenyl)-5-(4-pyridyl)-1H-imidazole;

N-1-Hydroxy-2-(4-methylthiophenyl)-4-(3-nitrophenyl)-5-(4-pyridyl)imidazole;

2-(4-Methylthiophenyl)-4-(3-nitrophenyl)-5-(4-pyridyl)-1H-imidazole;

4-(3-Methanesulfonamidophenyl)-2-(4-methylthiophenyl)-5-(4-pyridyl)-1H-imidazole;

3-[4-(4-Fluorophenyl)-5-(4-pyridyl)-1H-imidazol-2-yl]phenyl-1,2,4-oxadiazol-5(4H)-one;

4-(3-Acetamidophenyl)-2-(4-methylthiophenyl)-5-(4-pyridyl)-1H-imidazole;

4-(4-Fluorophenyl)-1-N-hydroxy-5-[4-(2-methylpyridyl)]-2-(4-methylthiophenyl)-imidazole;

3-[4-(4-Fluorophenyl)-5-(4-pyridyl)-1H-imidazol-2-yl]-phenyl-5,5-dimethyl-4,5-dihydro-1,2,4-oxadiazote;

N-Hydroxy-N-1-[4-[4-(4-fluorophenyl)-5-(4-pyridyl)-1H-imidazol-2-yl]phenyl]-ethyl]urea;

N-Hydroxy-N-[4-[4-(4-fluorophenyl)-5-(4-pyridyl)-1H-imidazol-2-yl-phenyl]-methyl urea;

4-(3-Methylthiophenyl)-2-(4-morpholinomethylphenyl)-5-(4-pyridyl)-1H-imidazole;

4-(3-Methylsulfinylphenyl)-2-(4-morpholinomethylphenyl)-5-(4-pyridyl)-1H-imidazole;

4-(3-Methanesulfonamidophenyl)-2-(4-methylsulfinylphenyl)-5-(4-pyridyl)-1H-imidazole-2-(4-Ethylthiophenyl)-4-(4-fluorophenyl)-5-(4-pyridyl)-1H-imidazole;

4-(4-Fluorophenyl)-2-[(4-(4-methyl-1-piperzinyl)-sulfonyl-phenyl]-5-(4-pyridyl) 1H-imidazole;

4-(4-Fluorophenyl)-2-[4-(N-methylmethanesulfonamido)-methylphenyl]-5-(4-pyridyl)-1H-imidazole;

Diethyl-[1-methyl-4-phenyl-5-(4-pyridyl)-imidazol-2-yl]-methoxy methylphosphonate;

4-(4-Fluorophenyl)-2-(4-methylthiophenyl)-5-(4-pyridyl)-1H-imidazole;

4-(4-Fluorophenyl)-2-(3-methylthiophenyl)-5-(4-pyridyl)-1H-imidazole;

4-(4-Fluorophenyl)-2-(3-methylsulfinylphenyl)-5-(4-pyridyl)-1H-imidazole;

4-(4-Fluorophenyl)-2-(4-methoxyphenyl)-5-(4-pyridyl) imidazole;

4-(4-Fluorophenyl)-2-(4-methylsulfinylphenyl)-1-(N-morpholinopropyl)-5-(4-pyridyl)imidazole;

4-(4-Fluorophenyl)-2-(4-methylthiophenyl)-1-(N-morpholinopropyl)-5-(4-pyridyl)imidazole;

4-(4-Fluorophenyl)-2-(4-methylsulfonylphenyl)-1-(N-morpholinopropyl)-5-(4-pyridyl)imidazole;

4-(4-Fluorophenyl)-1-(methylthio-1-propyl)-2-([4-N-morpholinomethyl]phenyl)-5-(4-pyridyl)-imidazole;

4-(4-Fluorophenyl)-1-(methylsulfinyl-1-propyl)-2-([4N-morpholinomethyl]phenyl)-5-(4-pyridyl)-imidazole; and 4-(4-Fluorophenyl)-1-(methylsulfonyl-1-propyl)-2-([4-N-morpholinomethyl]phenyl)-5-(4-pyridyl)imidazole.

These compounds can be made using organic synthesis techniques known to those skilled in the art, as well as by the methods described in U.S. Pat. No. 6,288,089, issued Sep. 11, 2001, which is incorporated herein by reference in its entirety. Further, specific examples of these compounds are found in the patent.

In another embodiment, the JNK inhibitor has the following structure (XVI):

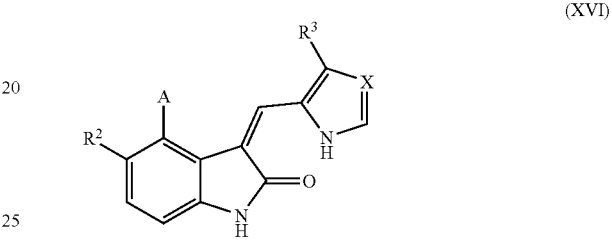

(XVI)

or pharmaceutically acceptable in vivo hydrolyzable esters, analogs, hydrolysis products, metabolites, salts, solvates, hydrates, clathrates, polymorphs, stereoisomers, derivatives and precursors thereof, wherein:

A is aryl or heteroaryl, each of which optionally substituted by one or more —$OR^4$, —$COR^4$, —$COOR^4$, —$CONR^6R^7$, —$NR^6R^7$, —CN, —$NO_2$, —$SO_2R^4$, —$SO_2NR^6R^7$, halogen, perfluoroalkyl, lower alkyl, lower alkyl substituted by (a), halogen, cycloalkyl, and/or heterocycle; cycloalkyl or cycloalkyl substituted by (a), halogen, lower alkyl, and/or heterocycle; heterocycle or heterocycle substituted by (a), halogen, lower alkyl, and/or cyoloalkyl;

where (a) is —$OR^4$, —$NR^6R^7$, —$COR^4$, —$COOR^4$, —$OCOR^4$, —$CONR^5R^7$, —CN, —$NO_2$, —$SO_2R^4$, or —$SO_2NR^6R^7$;

$R^2$ is hydrogen, —$OR^4$, —$COOR^4$, —$CONR^6R^7$, —$NR^6R^7$, halogen, —$NO_2$, —CN, —$SO_2NR^6R^7$, —$SO_2R^4$ perfluoroalkyl, lower alkyl, or lower alkyl substituted by —$OR^8$, —$NR^6R^7$, —$COR^4$, —$COOR^4$, and/or —$CONR^6R^7$;

$R^3$ is hydrogen, —$OR^4$, —$COR^4$, —$COOR^4$, —$CONR^6R^7$, halogen, —CN, —$NR^6R^7$, perfluoroalkyl, lower alkyl, or lower alkyl substituted by —$OR^8$ and/or —$NR^6R^7$;

$R^4$ is hydrogen, lower alkyl or lower alkyl substituted by (b), cycloalkyl and/or heterocycle; cycloalkyl or cyoloalkyl substituted (b), lower alkyl and/or heterocycle; heterocycle or heterocycle substituted by (b), lower alkyl and/cr cycloalkyl; where (b) is —$OR^5$, —$COOR^8$, —$COR^8$, —$CONR^8R^9$, —$NR^6R^7$, —CN, —$NO_2$, —$SO_2R^8$, or —$SO_2NR^8R^9$, $R^5$ is hydrogen, —$COR^8$, —$CONR^8R^9$, lower alkyl or lower alkyl substituted by —$OR^9$, —$NR^9R^{10}$, —$N(OCR^9)R^{10}$, —$COR^8$, —$CONR^9R^{10}$, and/or —$COOR^8$;

$R^6$ and $R^7$ are each independently hydrogen, —$COR^8$, —$COOR^8$, —$CONR^8R^9$, —$SO_2R^8$, —$SO_2NR^8R^9$, lower alkyl or lower alkyl substituted by cycloalkyl (or cycloalkyl substituted by (c), lower alkyl and/or heterocycle), heterocycle (or heterocycle substituted by (c), lower alkyl and/or cycloalkyl), aryl (or aryl substituted by (c), lower alkyl, cycloalkyl and/or heterocycle), or heteroaryl (or heteroaryl substituted by (c), lower alkyl, cyoloalkyl and/or heterocycle); or $R^6$ and $R^7$ are each independently cycloalkyl or cycloalkyl substituted by (c), lower alkyl and/or heterocycle; heterocycle (or heterocycle substituted by (c), lower alkyl and/or cycloalkyl), aryl (or aryl substituted by (c), lower alkyl, cycloalkyl and/or heterooycle), or heteroaryl (or heteroaryl substituted by (c), lower alkyl, cycloalkyl and/or heterocycle); where (c) is —$OR^5$, —$COOR^8$, —$COR^8$, —$CONR^8R^9$, —CN, —$NO_2$, —$SO_2R^8$, —$SO_2NR^8R^9$, —$NR^8R^9$; or alternatively, —$NR^6R^7$ forms a ring having 3 to 7 atoms, said ring optionally including one or more additional heteroatoms and being optionally substituted by one or more of lower alkyl, —$OR^5$, —$COR^8$, —$COOR^8$, $CONR^8R^9$, and —$NR^5R^9$;

$R^8$ is hydrogen, lower alkyl (or lower alkyl substituted by cycloalkyl, heterocycle, aryl, heteroaryl, —$OR^9$, —$NR^9R^{10}$, and/or —$N(COR^9)R^{10}$), aryl (or aryl substituted by (d), lower alkyl, cycloalkyl, heterocycle, halogen and/or —$SO_2F$), heteroaryl (or heteroaryl substituted by (d), lower alkyl, cycloalkyl, heterocycle, halogen and/or —$SO_2F$), cycloalkyl (or cycloalkyl substituted by (d), lower alkyl, heterocycle and/or aryl), or heterocycle (or heterocycle substituted by (d), lower alkyl, cyoloalkyl and/or aryl); where (d) is —$OR^9$, —$COOR^9$, —$COR^9$, —$CONR^{10}R^9$, —$NR^{10}R^9$, —CN, —$NO_2$, —$SO_2R^9$, or —$SO_2NR^{10}R^9$;

$R^9$ and $R^{10}$ are each independently hydrogen, lower alkyl or aryl; and X is =N— or =CH—.

The compounds of structure (XVI) can be made using organic synthesis techniques known to those skilled in the art, as well as by the methods described in U.S. Pat. No. 6,307,056, issued Oct. 23, 2001, which is incorporated herein by reference in its entirety (particularly at column 63, line 29 to column 66, line 12). Further, specific examples of these compounds are found in the patent.

In another embodiment, the JNK inhibitor has the following structure (XVII):

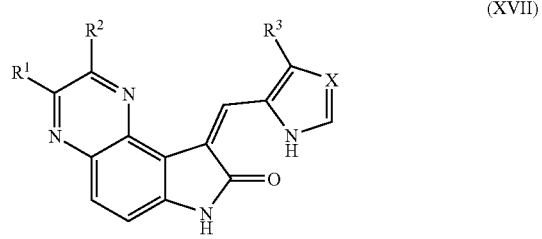

(XVII)

wherein:

$R^1$ and $R^2$ are independently selected from the group consisting of: hydrogen, —$OR^4$, —$COR^4$, —$COOR^4$, —$CONR^5R^6$, —$NR^5R^6$, lower alkyl which may be substituted by a member of the group (a) consisting of —$OR^4$, —$NR^5R^6$, halogen, —$COR^4$, —$COOR^4$, —$OCOR^4$, —$CONR^5R^6$, —CN, —$SO_2R^4$, —$SO_2NR^5R^6$; or by cycloalkyl, heterocycle, aryl, and heteroaryl, wherein the cycloalkyl and heterocycle each may be substituted by the group $R^{11}$ and the aryl and heteroaryl each may be substituted by the group $R^{12}$;

cycloalkyl which may be substituted by a member of the group (a) a defined earlier, or by lower alkyl, heterocycle, aryl, and heteroaryl, wherein the lower alkyl and heterocycle each may be substituted by the group $R^{11}$ and the aryl and heteroaryl each may be substituted by the group $R^{12}$;

heterocycle which may be substituted by a member of the group (a) as defined earlier, or by lower alkyl, cycloalkyl, aryl, and heteroaryl, wherein the lower alkyl and cycloalkyl each may be substituted by the group $R^{11}$ and the aryl and heteroaryl each maybe optionally substituted by the group $R^{12}$;

aryl which maybe substituted by a member of the group (b) consisting of —$OR^4$, —$NR^5R^6$, halogen, —$NO_2$, perfluoroalkyl, —$COR^4$, —$COOR^4$, —$OCOR^4$, —$CONR^5R^6$, —CN, —$SO_2R^4$, —$SO_2NR^5R^6$; or by lower alkyl, cycloalkyl, heterocycle, aryl, and heteroaryl, and wherein the lower alkyl, cycloalkyl and heterocycle each may be substituted by the group $R^{11}$ and the aryl and heteroaryl each maybe substituted by the group $R^{12}$, heteroaryl, which may be substituted by a member of the group (b) as defined earlier, or by lower alkyl, cycloalkyl, heterocycle, aryl, and heteroaryl and wherein the lower alkyl, cycloalkyl and heterocycle each may be optionally substituted by the group $R^{11}$ and the aryl and heteroaryl each maybe substituted by the group $R^{12}$, or alternatively, $R^1$ and $R^2$ can form a ring having 5-7 atoms, said ring optionally including one or more heteroatoms and being optionally substituted by a member of the group consisting of —$OR^8$, —$COR^7$, —$COOR^7$, —$OCOR^4$, —$CONR^7R^9$, —$NR^8R^9$, or lower alkyl which may be substituted by the group $R^{11}$;

$R^3$ is hydrogen, —$OR^4$, —$COR^4$, —$COOR^4$, —$OCOR^4$, —$CONR^5R^6$, halogen, —CN, perfluoroalkyl —$NR^5R^6$, or lower alkyl which may be substituted by —$OR^4$, —$OCOR^4$, or —$NR^5R^6$;

$R^4$ is hydrogen, lower alkyl which may be substituted by a member of the group(c) consisting of —$OR^8$, —$COOR^7$, —$COR^7$, —$CONR^5R^6$, —$NR^5R^6$, —$SO_2R^7$, —$SO_2NR^5R^6$, or by cycloalkyl, heterocycle, aryl, and heteroaryl, and wherein the cycloalkyl and heterocycle each may be substituted by the group $R^{11}$ and the aryl and heteroaryl each may be substituted by the group $R^{12}$, cycloalkyl which may be substituted by a member of the group (c) or by lower alkyl, heterocycle, aryl, and heteroaryl, and wherein the lower alkyl and heterocycle each may be substituted by the group $R^{11}$ and the aryl and heteroaryl each may be substituted by the group $R^{12}$, heterocycle which maybe substituted by a member of the group (c) or by cycloalkyl, lower alkyl, aryl, and heteroaryl, and wherein the cycloalkyl and lower alkyl each may be substituted by the group $R^{11}$ and the aryl and heteroaryl each may be substituted by the group $R^{12}$, aryl which maybe substituted by a member of the group (d) consisting of —$OR^8$, —$COOR^7$, —$COR^7$, —$CONR^5R^6$, —$NR^5R^6$, —$NO_2$, halogen, perfluoroalkyl, —$SO_2R^7$, —$SO_2NR^5R^6$ or by lower alkyl, cycloalkyl, heterocycle, aryl, and heteroaryl, and wherein the lower alkyl, cycloalkyl and heterocycle each may be substituted by the group $R^{11}$ and the aryl and heteroaryl each may be substituted by the group $R^{12}$, and heteroaryl which may be substituted by a member of the group (d) or by cycloalkyl, lower alkyl, heterocycle, aryl, and heteroaryl, and wherein the lower alkyl, cycloalkyl and heterocycle each may be substituted by the group $R^{11}$ and the aryl and heteroaryl each maybe substituted by the group $R^{12}$;

$R^5$ and $R^8$ are each independently hydrogen, —$COR^7$, —$COOR^7$, —$CONR^7R^9$, lower alkyl which may be substituted by a member of the group (e) consisting of —$OR^8$, —$COOR^7$, —$COR^7$, —$CONR^7R^8$, —$NR^7R^8$, —$SO_2R^7$, —$SO_2NR^7R^5$; or by cycloalkyl, heterocycle, aryl, and heteroaryl, and wherein the cycloalkyl and heterocycle each may be substituted by the group $R^{11}$ and the aryl and heteroaryl each may be substituted by the group $R^{12}$, cycloalkyl which may be substituted by a member of the group (e) as defined earlier, or by lower alkyl, heterocycle, aryl, and heteroaryl, and wherein the lower alkyl and heterocycle each maybe substituted by the group $R^{11}$ and the aryl and heteroaryl each may be substituted by the group $R^{12}$, heterocycle which may be substituted by a member of the group (e) as defined earlier, or by cycloalkyl, lower alkyl, aryl, and heteroaryl, and wherein the cycloalkyl and lower alkyl each may be substituted by the group $R^{11}$ and the aryl and heteroaryl each maybe substituted by the group $R^{12}$, aryl which may be substituted by a member of the group (f) consisting of $OR^8$, —$COOR^7$, —$COR^7$, —$CONR^7R^8$, —$NR^7R^8$, —$NO_2$, halogen, perfluoroalkyl, —$SO_2R^7$, —$SO_2NR^7R^8$ or by lower alkyl, cycloalkyl, heterocycle, aryl, and heteroaryl, and wherein the lower alkyl, cycloalkyl and heterocycle each may be substituted by the group $R^{11}$ and the aryl and heteroaryl each maybe substituted by the group $R^{12}$, and heteroaryl which may be substituted by a member of the group (f) as defined earlier, or by lower alkyl, cycloalkyl, heterocycle, aryl, and heteroaryl, and wherein the lower alkyl, cycloalkyl and heterocycle each may be substituted by the group $R^{11}$ and the aryl and heteroaryl each may be substituted by the group $R^{12}$ or alternatively, —$NR^5R^6$ can form a ring having 3 to 7 atoms, said ring optionally including one or more additional hetero atoms and being optionally substituted by lower alkyl, —$OR^8$, —$COR^7$, —$COOR^7$, —$CONR^7R^9$, or —$NR^8R^9$;

$R^7$ is hydrogen or lower alkyl which may be substituted by a member of the group consisting of cycloalkyl, heterocycle, aryl, heteroaryl, —$OR^9$, or —$NR^8R^9$;

$R^8$ is hydrogen, —$COR^9$, —$CONR^{10}R^9$, or lower alkyl which may be substituted by $R^{11}$;

$R^9$ and $R^{10}$ are each independently hydrogen or lower alkyl;

$R^{11}$ is —$OR^9$, —$COR^9$, —$COOR^9$, —$OCOR^9$, —$CONR^9R^{10}$, —$NR^9R^{10}$, —$N(COR^9)R^{10}$, —$SO_2R^9$, or —$SO_2NR^8R^{10}$;

$R^{12}$ is —$OR^9$, —$COR^9$, —$COOR^9$, —$OCOR^9$, —$CONR^9R^{10}$, —$NR^9R^{10}$, —$N(COR^9)R^{10}$, —$SO_2R^9$, —$SO_2NR^9R^{10}$, halogen, —CN, —$NO_2$, or perfluoroalkyl; and X is —N— or —C—.

The compounds of structure (XVII) can be made using organic synthesis techniques known to those skilled in the art, as well as by the methods described in International Publication No. WO 00/35921, published Jun. 22, 2000, which is incorporated herein by reference in its entirety (particularly at page 23, line 5 to page 26, line 14). Further, specific examples of these compounds are found in this publication.

In another embodiment, the JNK inhibitor has the following structure (XVIII):

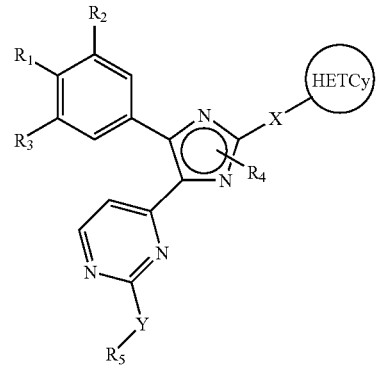

(XVIII)

wherein:
$R_1$ is —F, —Cl, —Br, —OH, —SH, —$NH_2$, or —$CH_3$;
$R_2$ is —F, —Cl, —Br, —OH, —SH, —$NH_2$, or —$CH_3$;
$R_3$ is —H, —F, —Cl, —Br, —OH, —SH, —$NH_2$, —$CH_3$, —$OCH_3$, or —$CH_2CH_3$;
$R_4$ is —$C_{1-4}$alkyl optionally substituted with a —$C_{3-7}$cycloalkyl;
$R_5$ is —$C_{1-4}$alkyl or —$C_{3-7}$cycloalkyl, wherein the —$C_{1-4}$ alkyl is optionally substituted with a phenyl;
X is a bond or an alkyl bridge having 1-3 carbons;
Y is —NH— or —$NH2^+$-; and
HETCy is a 4 to 10 membered non-aromatic heterocycle containing at least one N atom, optionally containing 1-2 additional N atoms and 0-10 or S atom, and optionally substituted with —$C_{1-4}$alkyl or —C(O)—O—$CH_2$ phenyl.

The compounds of structure (XVIII) can be made using organic synthesis techniques known to those skilled in the art, as well as by the methods described in International Publication No. WO 01/91749, published Dec. 6, 2001, which is incorporated herein by reference in its entirety (particularly at page 29, lines 1-22). Further, specific examples of these compounds are found in this publication.

In another embodiment, the JNK inhibitor has the following structure (XIX):

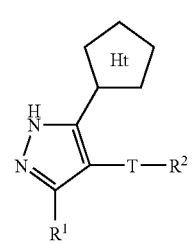

(XIX)

wherein:
Ht is a heterocyclic ring selected from pyrazol-3-yl, [1,2,4]triazol-3-yl, [1,2,3]triazol-4-yl, or tetrazol-5-yl, said pyrazol-3-yl having $R^3$ and $QR^4$ substituents, and said [1,2,4]triazol-3-yl or [1,2,3]triazol-4-yl substituted by either $R^3$ or $QR^4$;
$R^1$ is selected from R, halogen, $N(R^8)_2$, OR, NRCOR, $NRCON(R^8)_2$, $CON(R^8)_2$, $SO_2R$, $NRSO_2R$, or $SO_2N(R^8)_2$;
T is selected from a valence bond or a linker group;

each R is independently selected from hydrogen or an optionally substituted aliphatic group having one to six carbons;

$R^2$ is selected from hydrogen, CN, halogen, aryl, aralkyl, heteroaryl, heterocyclyl, an optionally substituted acyclic aliphatic chain group having one to six carbons, or an optionally substituted cyclic aliphatic group having four to ten carbons;

$R^3$ is selected from R, OH, OR, $N(R^8)_2$, halogen, or CN;

Q is a valence bond, J, or an optionally substituted $C_{1-6}$ alkylidene chain wherein up to two nonadjacent carbons of the alkylidene chain are each optionally and independently replaced by J;

J is selected from —C(=O)—, —CO$_2$—, —C(O)C(O)—, —NRCONR$^8$—, —N(R)N(R$^8$)—, —C(=O)NR$^8$—, —NRC(=O)—, —O—, —S—, —SO—, —SO$_2$—, —N(R)O—, —ON(R$^8$)—, —OC(=O)N(R$^8$)—, —N(R)COO—, —SO$_2$N(R$^8$)—, —N(R)SO$_2$—, or —NC(R$^8$);

$R^4$ is selected from —R$^8$, —R$^5$, —NH$_2$, —NHR$^5$, —N(R$^5$)$_2$, or —NR$^5$(CH$_2$)$_y$N(R$^5$)$_2$;

each $R^5$ is independently selected from R$^6$, R$^7$, —(CH$_2$)$_y$CH(R$^6$)(R$^7$), —(CH$_2$)$_y$R$^6$, —(CH$_2$)$_y$CH(R$^6$)$_2$, —(CH$_2$)$_y$CH(R$^7$)$_2$, or —(CH$_2$)$_y$R$^7$;

y is 0-6;

each $R^6$ is an optionally substituted group independently selected from an aliphatic, aryl, aralkyl, aralkoxy, heteroaryl, heteroarylalkyl, heteroarylalkoxy, heterocyclyl, heterocyclylalkyl, or heterocyclylalkoxy, group;

each $R^7$ is independently selected from an optionally substituted aliphatic, hydroxyalkyl, alkoxyalkyl, aryloxyalkyl, or alkoxycarbonyl;

each $R^8$ is independently selected from R, or two $R^8$ on the same nitrogen atom are taken together with the nitrogen to form a four to eight membered, saturated or unsaturated heterocyclic ring having one to three heteroatoms;

and each substitutable ring nitrogen is optionally substituted by R, NR$_2$, COR, CO$_2$(C$_1$-C$_6$ optionally substituted alkyl), SO$_2$(C$_2$-C$_6$ optionally substituted alkyl), CONR$_2$, and SO$_2$NR$_2$ provided that QR$^4$ is other than CON(CH$_3$)$_2$ when $R^1$ and $R^3$ are each hydrogen and when TR$^2$ is an unsubstituted phenyl ring attached at the 4-position of the pyrazole ring.

The compounds of structure (XIX) can be made using organic synthesis techniques known to those skilled in the art, as well as by the methods described in International Publication No. WO 01/56993, published Aug. 9, 2001, which is incorporated herein by reference in its entirety (particularly in at page 43 to page 45). Further, specific examples of these compounds are found in this publication.

In another embodiment, the JNK inhibitor has the following structure (XX):

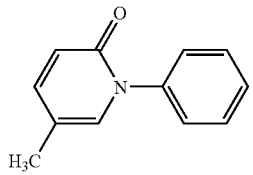

(XX)

The compound of structure (XX) can be made using organic synthesis techniques known to those skilled in the art, as well as by the methods described in International Publication No. WO 01/58448, published Aug. 16, 2001, which is incorporated herein by reference in its entirety (particularly in at page 39).

If the stereochemistry of a structure or a portion of a structure is not indicated with, for example, bold or dashed lines, the structure or portion of the structure is to be interpreted as encompassing all stereoisomers of it.

4.1.1. Patient Population

The invention provides methods for treating, preventing, and managing cancer by administrating to a patient a therapeutically or prophylactically effective amount of a JNK inhibitor in combination with one or more other therapeutic agents, or a pharmaceutical composition comprising a JNK inhibitor. The patient is preferably a mammal such as non-primate (e.g., cows, pigs, horses, cats, dogs, rats etc.) and a primate (e.g., monkey such as a cynomolgous monkey and a human). In a preferred embodiment, the patient is a human.

The invention encompasses methods for treating patients on any other treatment useful for the prevention or treatment of cancer. Using the methods of the invention, patients can be treated for the prevention, treatment or management of cancer, including, but not limited to, primary cancers, neoplasms, solid and blood born tumors, metastases, or any disease or disorder characterized by uncontrolled cell growth. The methods and compositions of the invention can be used with one or more conventional or experimental therapies that are used to prevent, manage or treat cancer.

Specific examples of cancers that can be treated by the methods encompassed by the invention include, but are not limited to, cancer of the head, neck, eye, mouth, throat, esophagus, chest, bone, lung, colon, rectum, stomach, prostate, breast, ovaries, kidney, liver, pancreas, and brain. In preferred embodiments, the cancer is breast cancer, colon cancer, prostate cancer, multiple myeloma, melanoma, lung cancer or ovarian cancer. Additional cancers are listed by example and not by limitation in the following section 4.1.1.1.

The methods and compositions of the invention comprise the administration of a JNK inhibitor in combination with one or more other therapeutic agents other than a JNK inhibitor to patients suffering from or expected to suffer from cancer. As used herein, cancer refers to primary or metastatic cancers. Such patients may or may not have been previously treated for cancer. The methods and compositions of the invention may be used as a first line or second line cancer treatment. The invention also comprises the treatment of a patient having cancer and immunosuppressed by reason of having previously undergone other cancer therapies. Included by the invention is also the treatment of patients undergoing other cancer therapies and the methods and compositions of the invention can be used before any adverse effects or intolerance occurs. The invention also encompasses methods for administering a JNK inhibitor to treat or ameliorate symptoms in refractory patients. In a certain embodiment, that a cancer is refractory to a therapy means that at least some significant portion of the cancer cells are not killed or their cell division arrested. In another embodiment, the cancer is refractory against currently used chemotherapeutic agents. In another embodiment, the cancer is refractory to multi-drug therapies. In another embodiment, the cancer is refractory against tamoxifen. In another embodiment, the cancer is androgen-independent. The determination of whether the cancer cells are refractory can be made either in vivo or in vitro by any method known in the art for assaying the effectiveness of treatment on cancer cells, using the art-accepted meanings of "refractory" in such a context. In various embodiments, a cancer is refractory where the number of cancer cells has not been significantly reduced, or has increased. The invention also encompasses methods for administering a JNK inhibitor to prevent the onset or recurrence of cancer in patients predisposed to having cancer.

In alternate embodiments, the invention provides methods for treating patients cancer by administering a JNK inhibitor in combination with any other treatment or to patients who have proven refractory to other treatments but are no longer on these treatments. In certain embodiments, the patients being treated by the methods of the invention are patients already being treated with chemotherapy, radiation therapy, hormonal therapy, or biological therapy/immunotherapy. Among these patients are refractory patients and those with cancer despite treatment with existing cancer therapies. In other embodiments, the patients have been treated and have no disease activity and a JNK inhibitor is administered to prevent the recurrence of cancer.

In preferred embodiments, the existing treatment is chemotherapy. In particular embodiments, the existing treatment includes administration of chemotherapies including, but not limited to methotrexate, mercaptopurine, thioguanine, hydroxyurea, cytarabine, cyclophosphamide, ifosfamide, nitrosoureas, cisplatin, carboplatin, mitomycin, dacarbazine, procarbizine, etoposides, campathecins, bleomycin, doxorubicin, idarubicin, daunorubicin, dactinomycin, plicamycin, mitoxantrone, asparaginase, vinblastine, vincristine, vinorelbine, paclitaxel, docetaxel, cetuximab (Erbitux™), thalidomide, any SelCid™ or IMiD™ compounds, in particular CC-4047 (Actimid™) and CC-5013 (Revimid™). Among these patients are patients treated with radiation therapy, hormonal therapy and/or biological therapy/immunotherapy. Also among these patients are those who have undergone surgery for the treatment of cancer.

Alternatively, the invention also encompasses methods for treating patients having radiation therapy. Among these patients are patients treated with chemotherapy, hormonal therapy and/or biological therapy/immunotherapy. Also among these patients are those who have undergone surgery for the treatment of cancer.

In other embodiments, the invention encompasses methods for treating patients having hormonal therapy and/or biological therapy/immunotherapy. Among these patients are patients treated with chemotherapy and/or radiation therapy. Also among these patients are those who have undergone surgery for the treatment of cancer.

Additionally, the invention also provides methods of treatment of cancer as an alternative to chemotherapy, radiation therapy, hormonal therapy, and/or biological therapy/immunotherapy where the therapy has proven or may prove too toxic, i.e., results in unacceptable or unbearable side effects, for the patient being treated. The patient being treated with the methods of the invention may, optionally, be treated with other cancer treatments such as surgery, chemotherapy, radiation therapy, hormonal therapy or biological therapy, depending on which treatment was found to be unacceptable or unbearable.

In other embodiments, the invention provides administration of a JNK inhibitor without any other cancer therapies for the treatment of cancer, but who have proved refractory to such treatments. In specific embodiments, patients refractory to other cancer therapies are administered a JNK inhibitor in the absence of cancer therapies.

4.1.1.1 Cancers

Cancers and related disorders that can be treated or prevented by methods and compositions of the present invention include but are not limited to the following: Leukemias such as but not limited to, acute leukemia, acute lymphocytic leukemia, acute myelocytic leukemias such as myeloblastic, promyelocytic, myelomonocytic, monocytic, erythroleukemia leukemias and myelodysplastic syndrome, chronic leukemias such as but not limited to, chronic myelocytic (granulocytic) leukemia, chronic lymphocytic leukemia, hairy cell leukemia; polycythemia vera; lymphomas such as but not limited to Hodgkin's disease, non-Hodgkin's disease; multiple myelomas such as but not limited to smoldering multiple myeloma, nonsecretory myeloma, osteosclerotic myeloma, plasma cell leukemia, solitary plasmacytoma and extramedullary plasmacytoma; Waldenström's macroglobulinemia; monoclonal gammopathy of undetermined significance; benign monoclonal gammopathy; heavy chain disease; bone and connective tissue sarcomas such as but not limited to bone sarcoma, osteosarcoma, chondrosarcoma, Ewing's sarcoma, malignant giant cell tumor, fibrosarcoma of bone, chordoma, periosteal sarcoma, soft-tissue sarcomas, angiosarcoma (hemangiosarcoma), fibrosarcoma, Kaposi's sarcoma, leiomyosarcoma, liposarcoma, lymphangiosarcoma, metastatic cancers, neurilemmoma, rhabdomyosarcoma, synovial sarcoma; brain tumors such as but not limited to, glioma, astrocytoma, brain stem glioma, ependymoma, oligodendroglioma, nonglial tumor, acoustic neurinoma, craniopharyngioma, medulloblastoma, meningioma, pineocytoma, pineoblastoma, primary brain lymphoma; breast cancer, including, but not limited to, adenocarcinoma, lobular (small cell) carcinoma, intraductal carcinoma, medullary breast cancer, mucinous breast cancer, tubular breast cancer, papillary breast cancer, primary cancers, Paget's disease, and inflammatory breast cancer; adrenal cancer such as but not limited to pheochromocytom and adrenocortical carcinoma; thyroid cancer such as but not limited to papillary or follicular thyroid cancer, medullary thyroid cancer and anaplastic thyroid cancer; pancreatic cancer such as but not limited to, insulinoma, gastrinoma, glucagonoma, vipoma, somatostatin-secreting tumor, and carcinoid or islet cell tumor; pituitary cancers such as but limited to Cushing's disease, prolactin-secreting tumor, acromegaly, and diabetes insipius; eye cancers such as but not limited to ocular melanoma such as iris melanoma, choroidal melanoma, and cilliary body melanoma, and retinoblastoma; vaginal cancers such as squamous cell carcinoma, adenocarcinoma, and melanoma; vulvar cancer such as squamous cell carcinoma, melanoma, adenocarcinoma, basal cell carcinoma, sarcoma, and Paget's disease; cervical cancers such as but not limited to, squamous cell carcinoma, and adenocarcinoma; uterine cancers such as but not limited to endometrial carcinoma and uterine sarcoma; ovarian cancers such as but not limited to, ovarian epithelial carcinoma, borderline tumor, germ cell tumor, and stromal tumor; esophageal cancers such as but not limited to, squamous cancer, adenocarcinoma, adenoid cyctic carcinoma, mucoepidermoid carcinoma, adenosquamous carcinoma, sarcoma, melanoma, plasmacytoma, verrucous carcinoma, and oat cell (small cell) carcinoma; stomach cancers such as but not limited to, adenocarcinoma, fungating (polypoid), ulcerating, superficial spreading, diffusely spreading, malignant lymphoma, liposarcoma, fibrosarcoma, and carcinosarcoma; colon cancers; rectal cancers; liver cancers such as but not limited to hepatocellular carcinoma and hepatoblastoma, gallbladder cancers such as adenocarcinoma; cholangiocarcinomas such as but not limited to pappillary, nodular, and diffuse; lung cancers such as non-small cell lung cancer, squamous cell carcinoma (epidermoid carcinoma), adenocarcinoma, large-cell carcinoma and small-cell lung cancer; testicular cancers such as but not limited to germinal tumor, seminoma, anaplastic, classic (typical), spermatocytic, non-seminoma, embryonal carcinoma, teratoma carcinoma, choriocarcinoma (yolk-sac tumor), prostate cancers such as but not limited to, adenocarcinoma, leiomyosarcoma, and rhabdomyosarcoma; penal cancers; oral cancers such as but not limited to squamous cell carcinoma; basal cancers; salivary gland cancers such as but not limited to adenocarcinoma, mucoepidermoid carcinoma, and adenoidcystic carcinoma; pharynx cancers such as but not limited to squamous cell cancer, and verrucous; skin cancers such as but not limited to, basal cell carcinoma, squamous cell carcinoma and melanoma, superficial spreading melanoma, nodular melanoma, lentigo malignant melanoma, acral lentiginous melanoma; kidney cancers such as but not limited to renal cell cancer, adenocarcinoma, hypernephroma, fibrosarcoma, transitional cell cancer (renal pelvis and/or uterer); Wilms' tumor; bladder cancers such as but not limited to transitional cell carcinoma, squamous cell cancer, adenocarcinoma, carcinosarcoma. In addition, cancers include myxosarcoma, osteogenic sarcoma, endotheliosarcoma, lymphangioendotheliosarcoma, mesothelioma, synovioma, hemangioblastoma, epithelial carcinoma, cystadenocarcinoma, bronchogenic carcinoma, sweat gland carcinoma, sebaceous gland carcinoma, papillary carcinoma and papillary adenocarcinomas (for a review of such disorders, see Fishman et al., 1985, *Medicine*, 2d Ed., J. B. Lippincott Co., Philadelphia and Murphy et al., 1997, *Informed Decisions: The Complete Book of Cancer Diagnosis, Treatment, and Recovery*, Viking Penguin, Penguin Books U.S.A., Inc., United States of America)

Accordingly, the methods and compositions of the invention are also useful in the treatment or prevention of a variety of cancers or other abnormal proliferative diseases, including (but not limited to) the following: carcinoma, including that of the bladder, breast, colon, kidney, liver, lung, ovary, pancreas, stomach, cervix, thyroid and skin; including squamous cell carcinoma; hematopoietic tumors of lymphoid lineage, including leukemia, acute lymphocytic leukemia, acute lymphoblastic leukemia, B-cell lymphoma, T-cell lymphoma, Berketts lymphoma; hematopoietic tumors of myeloid lineage, including acute and chronic myelogenous leukemias and promyelocytic leukemia; tumors of mesenchymal orignin, including fibrosarcoma and rhabdomyoscarcoma; other tumors, including melanoma, seminoma, tetratocarcinoma, neuroblastoma and glioma; tumors of the central and peripheral nervous system, including astrocytoma, glioblastoma multiforme, neuroblastoma, glioma, and schwannomas; solid and blood born tumors; tumors of mesenchymal origin, including fibrosafcoma, rhabdomyoscarama, and osteosarcoma; and other tumors, including melanoma, xenoderma pegmentosum, keratoactanthoma, seminoma, thyroid follicular cancer and teratocarcinoma. It is also contemplated that cancers caused by aberrations in apoptosis would also be treated by the methods and compositions of the invention. Such cancers may include but not be limited to follicular lymphomas, carcinomas with p53 mutations, hormone dependent tumors of the breast, prostate and ovary, and precancerous lesions such as familial adenomatous polyposis, and myelodysplastic syndromes. In specific embodiments, malignancy or dysproliferative changes (such as metaplasias and dysplasias), or hyperproliferative disorders, are treated or prevented in the ovary, bladder, breast, colon, lung, skin, pancreas, or uterus. In other specific embodiments, sarcoma, melanoma, or leukemia is treated or prevented.

In preferred embodiments, the methods and compositions of the invention are used for the treatment and/or prevention of breast, colon, ovarian, lung, and prostate cancers and melanoma and are provided below by example rather than by limitation.

4.1.2. Other Prophylactic/Therapeutic Agents

According to the invention, therapy by administration of a JNK inhibitor is combined with the administration of one or more therapies such as, but not limited to, chemotherapies, radiation therapies, hormonal therapies, bone marrow transplants, stem cell replacement therapies and/or biological therapies/immunotherapies.

In a specific embodiment, the methods of the invention encompass the administration of one or more angiogenesis inhibitors such as but not limited to: Angiostatin (plasminogen fragment); antiangiogenic antithrombin III; Angiozyme; ABT-627; Bay 12-9566; Benefin; Bevacizumab; BMS-275291; cartilage-derived inhibitor (CDI); CAI; CD59 complement fragment; CEP-7055; Col 3; Combretastatin A-4; Endostatin (collagen XVIII fragment); Fibronectin fragment; Gro-beta; Halofuginone; Heparinases; Heparin hexasaccharide fragment; HMV833; Human chorionic gonadotropin (hCG); IM-862; Interferon alpha/beta/gamma; Interferon inducible protein (IP-10); Interleukin-12; Kringle 5 (plasminogen fragment); Marimastat; anti-inflammatory steroids such as but not limited to dexamethasone; Metalloproteinase inhibitors (TIMPs); 2-Methoxyestradiol; MMI 270 (CGS 27023A); MoAb IMC-1C11; Neovastat; NM-3; Panzem; PI-88; Placental ribonuclease inhibitor; Plasminogen activator inhibitor; Platelet factor-4 (PF4); Prinomastat; Prolactin 16 kD fragment; Proliferin-related protein (PRP); PTK 787/ZK 222594; Retinoids; Solimastat; Squalamine; SS 3304; SU 5416; SU6668; SU11248; Tetrahydrocortisol-S; tetrathiomolybdate; thalidomide; Thrombospondin-1 (TSP-1); TNP-470; Transforming growth factor-beta (TGF-b); Vasculostatin; Vasostatin (calreticulin fragment); ZD6126; ZD 6474; farnesyl transferase inhibitors (FTI); and bisphosphonates.

Additional examples of anti-cancer agents that can be used in the various embodiments of the invention, including pharmaceutical compositions and dosage forms and kits of the invention, include, but are not limited to: acivicin; aclarubicin; acodazole hydrochloride; acronine; adozelesin; aldesleukin; altretamine; ambomycin; ametantrone acetate; aminoglutethimide; amsacrine; anastrozole; anthramycin; asparaginase; asperlin; azacitidine; azetepa; azotomycin; batimastat; benzodepa; bicalutamide; bisantrene hydrochloride; bisnafide dimesylate; bizelesin; bleomycin sulfate; brequinar sodium; bropirimine; busulfan; cactinomycin; calusterone; caracemide; carbetimer; carboplatin; carmustine; carubicin hydrochloride; carzelesin; cedefingol; chlorambucil; cirolemycin; cisplatin; cladribine; crisnatol mesylate; cyclophosphamide; cytarabine; dacarbazine; dactinomycin; daunorubicin hydrochloride; decitabine; dexormaplatin; dezaguanine; dezaguanine mesylate; diaziquone; docetaxel; doxorubicin; doxorubicin hydrochloride; droloxifene; droloxifene citrate; dromostanolone propionate; duazomycin; edatrexate; eflornithine hydrochloride; elsamitrucin; enloplatin; enpromate; epipropidine; epirubicin hydrochloride; erbulozole; Erbitux™; esorubicin hydrochloride; estramustine; estramustine phosphate sodium; etanidazole; etoposide; etoposide phosphate; etoprine; fadrozole hydrochloride; fazarabine; fenretinide; floxuridine; fludarabine phosphate; fluorouracil; flurocitabine; fosquidone; fostriecin sodium; gemcitabine; gemcitabine hydrochloride; hydroxyurea; idarubicin hydrochloride; ifosfamide; ilmofosine; ImiDs™; interleukin II (including recombinant interleukin II, or rIL2), interferon -2a; interferon alpha-2b; interferon alpha-n1; interferon alpha-n3; interferon beta-I a; interferon gamma-I b; iproplatin; irinotecan hydrochloride; lanreotide acetate; letrozole; leuprolide acetate; liarozole hydrochloride; lometrexol sodium; lomustine; losoxantrone hydrochloride; masoprocol; maytansine; mechlorethamine hydrochloride; megestrol acetate; melengestrol acetate; melphalan; menogaril; mercaptopurine; methotrexate; methotrexate sodium; metoprine; meturedepa; mitindomide; mitocarcin; mitocromin; mitogillin; mitomalcin; mitomycin; mitosper; mitotane; mitoxantrone hydrochloride; mycophenolic acid; nocodazole; nogalamycin; ormaplatin; oxisuran; paclitaxel; pegaspargase; peliomycin; pentamustine; peplomycin sulfate; perfosfamide; pipobroman; piposulfan; piroxantrone hydrochloride; plicamycin; plomestane; porfimer sodium; porfiromycin; prednimustine; procarbazine hydrochloride; puromycin; puromycin hydrochloride; pyrazofurin; riboprine; rogletimide; safingol; safingol hydrochloride; SelCid™; semustine; simtrazene; sparfosate sodium; sparsomycin; spirogermanium hydrochloride; spiromustine; spiroplatin; streptonigrin; streptozocin; sulofenur; talisomycin; tecogalan sodium; tegafur; teloxantrone hydrochloride; temoporfin; teniposide; teroxirone; testolactone; thiamiprine; thioguanine; temozolomide; temodar; thiotepa; tiazofurin; tirapazamine; toremifene citrate; trestolone acetate; triciribine phosphate; trimetrexate; trimetrexate glucuronate; triptorelin; tubulozole hydrochloride; uracil mustard; uredepa; vapreotide; verteporfin; vinblastine sulfate; vincristine sulfate; vindesine; vindesine sulfate; vinepidine sulfate; vinglycinate sulfate; vinleurosine sulfate; vinorelbine tartrate; vinrosidine sulfate; vinzolidine sulfate; vorozole; zeniplatin; zinostatin; zorubicin hydrochloride. Other anticancer drugs include, but are not limited to: 20-epi-1,25 dihydroxyvitamin D3; 5-ethynyluracil; abiraterone; aclarubicin; acylfulvene; adecypenol; adozelesin; aldesleukin; ALL-TK antagonists; altretamine; ambamustine; amidox; amifostine; aminolevulinic acid; amrubicin; amsacrine; anagrelide; anastrozole; andrographolide; angiogenesis inhibitors; antagonist D; antagonist G; antarelix; anti-dorsalizing morphogenetic protein-1; antiandrogen, prostatic carcinoma; antiestrogen; antineoplaston; aphidicolin glycinate; apoptosis gene modulators; apoptosis regulators; apurinic acid; ara-CDP-DL-PTBA; arginine deaminase; asulacrine; atamestane; atrimustine; axinastatin 1; axinastatin 2; axinastatin 3; azasetron; azatoxin; azatyrosine; baccatin III derivatives; balanol; batimastat; BCR/ABL antagonists; benzochlorins; benzoylstaurosporine; beta lactam derivatives; beta-alethine; betaclamycin B; betulinic acid; bFGF inhibitor; bicalutamide; bisantrene; bisaziridinylspermine; bisnafide; bistratene A; bizelesin; breflate; bropirimine; budotitane; buthionine sulfoximine; calcipotriol; calphostin C; camptothecin derivatives; canarypox IL-2; capecitabine; carboxamide-amino-triazole; carboxyamidotriazole; CaRest M3; CARN 700; cartilage derived inhibitor; carzelesin; casein kinase inhibitors (ICOS); cell-cycle inhibitors (e.g., flavopiridol A, tryprostatin B, p19ink4D); cyclin-dependent kinase inhibitors (e.g., roscovitine, olomucine and purine analogs); MAP kinase inhibitors (CNI-1493); castanospermine; cecropin B; cetrorelix; chlorlns; chloroquinoxaline sulfonamide; cicaprost; cis-porphyrin; cladribine; clomifene analogues; clotrimazole; collismycin A; collismycin B; combretastatin A4; combretastatin analogue; conagenin; crambescidin 816; crisnatol; cryptophycin 8; cryptophycin A derivatives; curacin A; cyclopentanthraquinones; cycloplatam; cypemycin; cytarabine ocfosfate; cytolytic factor; cytostatin; dacliximab; decitabine; dehydrodidemin B; deslorelin; dexamethasone; dexifosfamide; dexrazoxane; dexverapamil; diaziquone; didemin B; didox; diethylnorspermine; dihydro-5-azacytidine; dihydrotaxol, 9-; dioxamycin; diphenyl spiromustine; docetaxel; docosanol; dolasetron; doxifluridine; droloxifene; dronabinol; duocarmycin SA; ebselen; ecomustine; edelfosine; edrecolomab; eflornithine; elemene; emitefur; epirubicin; epristeride; estramustine analogue; estrogen agonists; estrogen antagonists; etanidazole; etoposide phosphate; exemestane; fadrozole; fazarabine; fenretinide; filgrastim; finasteride; flavopiridol; flezelastine; fluasterone; fludarabine; fluorodaunorunicin hydrochloride; forfenimex; formestane; fostriecin; fotemustine; gadolinium texaphyrin; gallium nitrate; galocitabine; ganirelix; gelatinase inhibitors; gemcitabine; glutathione inhibitors; hepsulfam; heregulin; hexamethylene bisacetamide; hypericin; ibandronic acid; idarubicin; idoxifene; idramantone; ilmofosine; ilomastat; imidazoacridones; imiquimod; immunostimulant peptides; insulin-like growth factor-1 receptor inhibitor; interferon agonists; interferons; interleukins; iobenguane; iododoxorubicin; ipomeanol, 4-; iroplact; irsogladine; isobengazole; isohomohalicondrin B; itasetron; jasplakinolide; kahalalide F; lamellarin-N triacetate; lanreotide; leinamycin; lenograstim; lentinan sulfate; leptolstatin; letrozole; leukemia inhibiting factor; leukocyte alpha interferon; leuprolide+estrogen+progesterone; leuprorelin; levamisole; liarozole; linear polyamine analogue; lipophilic disaccharide peptide; lipophilic platinum compounds; lissoclinamide 7; lobaplatin; lombricine; lometrexol; lonidamine; losoxantrone; lovastatin; loxoribine; lurtotecan; lutetium texaphyrin; lysofylline; lytic peptides; maitansine; mannostatin A; marimastat; masoprocol; maspin; matrilysin inhibitors; matrix metalloproteinase inhibitors; menogaril; merbarone; meterelin; methioninase; metoclopramide; MIF inhibitor; mifepristone; miltefosine; mirimostim; mismatched double stranded RNA; mitoguazone; mitolactol; mitomycin analogues; mitonafide; mitotoxin fibroblast growth factor-saporin; mitoxantrone; mofarotene; molgramostim; monoclonal antibody, human chorionic gonadotrophin; monophosphoryl lipid A+myobacterium cell wall sk; mopidamol; multiple drug resistance gene inhibitor; multiple tumor suppressor 1-based therapy; mustard anticancer agent; mycaperoxide B; mycobacterial cell wall extract; myriaporone; N-acetyldinaline; N-substituted benzamides; nafarelin; nagrestip; naloxone+pentazocine; napavin; naphterpin; nartograstim; nedaplatin; nemorubicin; neridronic acid; neutral endopeptidase; nilutamide; nisamycin; nitric oxide modulators; nitroxide antioxidant; nitrullyn; O6-benzylguanine; octreotide; okicenone; oligonucleotides; onapristone; ondansetron; ondansetron; oracin; oral cytokine inducer; ormaplatin; osaterone; oxaliplatin; oxaunomycin; paclitaxel; paclitaxel analogues; paclitaxel derivatives; palauamine; palmitoylrhizoxin; pamidronic acid; panaxytriol; panomifene; parabactin; pazelliptine; pegaspargase; peldesine; pentosan polysulfate sodium; pentostatin; pentrozole; perflubron; perfosfamide; perillyl alcohol; phenazinomycin; phenylacetate; phosphatase inhibitors; picibanil; pilocarpine hydrochloride; pirarubicin; piritrexim; placetin A; placetin B; plasminogen activator inhibitor; platinum complex; platinum compounds; platinum-triamine complex; porfimer sodium; porfiromycin; prednisone; propyl bis-acridone; prostaglandin J2; proteasome inhibitors; protein A-based immune modulator; protein kinase C inhibitor; protein kinase C inhibitors, microalgal; protein tyrosine phosphatase inhibitors; purine nucleoside phosphorylase inhibitors; purpurins; pyrazoloacridine; pyridoxylated hemoglobin polyoxyethylene conjugate; raf antagonists; raltitrexed; ramosetron; retinoic acid (e.g., 9-cis RA); histone deacetylase inhibitors (e.g., sodium butyrate, suberoylanilide hydroxamic acid); TRAIL; ras farnesyl protein transferase inhibitors; ras inhibitors; ras-GAP inhibitor; retelliptine demethylated; rhenium Re 186 etidronate; rhizoxin; ribozymes; RII retinamide; rogletimide; rohitukine; romurtide; roquinimex; rubiginone B1; ruboxyl; safingol; saintopin; SarCNU; sarcophytol A; sargramostim; Sdi 1 mimetics; semustine; senescence derived inhibitor 1; sense oligonucleotides; signal transduction inhibitors; signal transduction modulators; single chain antigen binding protein; sizofiran; sobuzoxane; sodium borocaptate; sodium phenylacetate; solverol; somatomedin binding protein; sonermin; sparfosic acid; spicamycin D; spiromustine; splenopentin; spongistatin 1; squalamine; stem cell inhibitor; stem-cell division inhibitors; stipiamide; stromelysin inhibitors; sulfinosine; superactive vasoactive intestinal peptide antagonist; suradista; suramin; swainsonine; synthetic glycosaminoglycans; tallimustine; tamoxifen methiodide; tauromustine; tazarotene; tecogalan sodium; tegafur; tellurapyrylium; telomerase inhibitors; temoporfin; temozolomide; teniposide; tetrachlorodecaoxide; tetrazomine; thaliblastine; thiocoraline; thrombopoietin; thrombopoietin mimetic; thymalfasin; thymopoictin receptor agonist; thymotrinan; thyroid stimulating hormone; tin ethyl etiopurpurin; tirapazamine; titanocene bichloride; topsentin; toremifene; totipotent stem cell factor; translation inhibitors; tretinoin; triacetyluridine; triciribine; trimetrexate; triptorelin; tropisetron; turosteride; tyrosine kinase inhibitors; tyrphostins; UBC inhibitors; ubenimex; urogenital sinus-derived growth inhibitory factor; urokinase receptor antagonists; vapreotide; variolin B; vector system, erythrocyte gene therapy; velaresol; veramine; verdins; verteporfin; vinorelbine; vinxaltine; vitaxin; vorozole; zanoterone; zeniplatin; zilascorb; and zinostatin stimalamer. Preferred additional anti-cancer drugs are 5-fluorouracil and leucovorin. These two agents are particularly useful when used in methods employing thalidomide and a topoisomerase inhibitor.

In more particular embodiments, the present invention also comprises the administration of one or more inhibitors of JNK in combination with the administration of one or more therapies such as, but not limited to agents such as those disclosed in Table I, preferably for the treatment of breast, ovary, prostate, colon and lung cancers as described above.

TABLE 1

| Therapeutic Agent | Dose/Administration/Formulation | | |
|---|---|---|---|
| doxorubicin hydrochloride (Adriamycin RDF ® and Adriamycin PFS ®) | Intravenous | 60-75 mg/m$^2$ on Day 1 | 21 day intervals |
| epirubicin hydrochloride (Ellence ™) | Intravenous | 100-120 mg/m$^2$ on Day 1 of each cycle or divided equally and given on Days 1-8 of the cycle | 3-4 week cycles |
| fluorouracil | Intravenous | How supplied: 5 mL and 10 mL vials (containing 250 and 500 mg flourouracil respectively) | as needed or prescribed |
| docetaxel (Taxotere ®) | Intravenous | 60-100 mg/m$^2$ over 1 hour | Once every 3 weeks |
| paclitaxel (Taxol ®) | Intravenous | 175 mg/m$^2$ over 3 hours | Every 3 weeks for 4 courses (administered sequentially to doxorubicin-containing combination chemotherapy) |
| tamoxifen citrate (Nolvadex ®) | Oral (tablet) | 20-40 mg Dosages greater than 20 mg should be given in divided doses (morning and evening) | Daily |
| leucovorin calcium for injection | Intravenous or intramuscular injection | How supplied: 350 mg vial | Dosage is unclear from text. PDR 3610 |
| luprolide acetate (Lupron ®) | Single subcutaneous injection | 1 mg (0.2 mL or 20 unit mark) | Once a day |
| flutamide (Eulexin ®) | Oral (capsule) | 250 mg (capsules contain 125 mg flutamide each) | 3 times a day at 8 hour intervals (total daily dosage 750 mg) |
| nilutamide (Nilandron ®) | Oral (tablet) | 300 mg or 150 mg (tablets contain 50 or 150 mg nilutamide each) | 300 mg once a day for 30 days followed by 150 mg once a day |
| bicalutamide (Casodex ®) | Oral (tablet) | 50 mg (tablets contain 50 mg bicalutamide each) | Once a day |
| progesterone | Injection | USP in sesame oil 50 mg/mL | as needed or prescribed |
| ketoconazole (Nizoral ®) | Cream | 2% cream applied once or twice daily depending on symptoms | as needed or prescribed |
| prednisone | Oral (tablet) | Initial dosage may vary from 5 mg to 60 mg per day depending on the specific disease entity being treated. | as needed or prescribed |

TABLE 1-continued

| Therapeutic Agent | Dose/Administration/Formulation | | |
|---|---|---|---|
| estramustine phosphate sodium (Emcyt ®) | Oral (capsule) | 14 mg/kg of body weight (i.e. one 140 mg capsule for each 10 kg or 22 lb of body weight) | Daily given in 3 or 4 divided doses |
| etoposide or VP-16 | Intravenous | 5 mL of 20 mg/mL solution (100 mg) | as needed or prescribed |
| dacarbazine (DTIC-Dome ®) | Intravenous | 2-4.5 mg/kg | Once a day for 10 days. May be repeated at 4 week intervals |
| polifeprosan 20 with carmustine implant (BCNU) (nitrosourea) (Gliadel ®) | wafer placed in resection cavity | 8 wafers, each containing 7.7 mg of carmustine, for a total of 61.6 mg, if size and shape of resection cavity allows | as needed or prescribed |
| cisplatin | Injection | [n/a in PDR 861] How supplied: solution of 1 mg/mL in multi-dose vials of 50 mL and 100 mL | as needed or prescribed |
| mitomycin | Injection | supplied in 5 mg and 20 mg vials (containing 5 mg and 20 mg mitomycin) | as needed or prescribed |
| gemcitabine HCl (Gemzar ®) | Intravenous | For NSCLC-2 schedules have been investigated and the optimum schedule has not been determined 4 week schedule- administration intravenously at 1000 mg/m$^2$ over 30 minutes on 3 week schedule- Gemzar administered intravenously at 1250 mg/m$^2$ over 30 minutes | 4 week schedule- Days 1, 8 and 15 of each 28-day cycle. Cisplatin intravenously at 100 mg/m$^2$ on day 1 after the infusion of Gemzar. 3 week schedule- Days 1 and 8 of each 21 day cycle. Cisplatin at dosage of 100 mg/m$^2$ administered intravenously after administration of Gemzar on day 1. |
| carboplatin (Paraplatin ®) | Intravenous | Single agent therapy: 360 mg/m$^2$ I.V. on day 1 (infusion lasting 15 minutes or longer) Other dosage calculations: Combination therapy with cyclophosphamide, Dose adjustment recommendations, Formula dosing, etc. | Every 4 weeks |
| ifosamide (Ifex ®) | Intravenous | 1.2 g/m$^2$ daily | 5 consecutive days Repeat every 3 weeks or after recovery from hematologic toxicity |
| topotecan hydrochloride (Hycamtin ®) | Intravenous | 1.5 mg/m$^2$ by intravenous infusion over 30 minutes daily | 5 consecutive days, starting on day 1 of 21 day course |
| cyclophosphamide | Parenteral or Oral | 1-5 mg/kg/day | as needed or prescribed |
| irinotecan | Intraveinous or Infusion | 20-500 mg/m$^2$ | as needed or prescribed |

The invention also encompasses administration of JNK inhibitors in combination with radiation therapy comprising the use of x-rays, gamma rays and other sources of radiation to destroy the cancer cells. In preferred embodiments, the radiation treatment is administered as external beam radiation or teletherapy wherein the radiation is directed from a remote source. In other preferred embodiments, the radiation treatment is administered as internal therapy or brachytherapy wherein a radiaoactive source is placed inside the body close to cancer cells or a tumor mass.

4.3 Pharmaceutical Compositions

The compositions of the invention include bulk drug compositions useful in the manufacture of pharmaceutical compositions (e.g., impure or non-sterile compositions) and pharmaceutical compositions (i.e., compositions that are suitable for administration to a patient) which can be used in the preparation of unit dosage forms. Such compositions comprise a prophylactically or therapeutically effective amount of a prophylactic and/or therapeutic agent disclosed herein or a combination of those agents and a pharmaceutically acceptable carrier. Preferably, compositions of the invention comprise a prophylactically or therapeutically effective amount of JNK inhibitor and/or an anti-cancer agent, and a pharmaceutically acceptable carrier.

In a specific embodiment, the term "pharmaceutically acceptable" means approved by a regulatory agency of the Federal or a state government or listed in the U.S. Pharmacopeia or other generally recognized pharmacopeia for use in animals, and more particularly in humans. The term "carrier" refers to a diluent, adjuvant, excipient, or vehicle with which a compound of the invention is administered. Such pharmaceutical vehicles can be liquids, such as water and oils, including those of petroleum, animal, vegetable or synthetic origin, such as peanut oil, soybean oil, mineral oil, sesame oil and the like. The pharmaceutical vehicles can be saline, gum acacia, gelatin, starch paste, talc, keratin, colloidal silica, urea, and the like. In addition, auxiliary, stabilizing, thickening, lubricating and coloring agents may be used. When administered to a patient, the compounds of the invention and pharmaceutically acceptable vehicles are preferably sterile. Water is a preferred vehicle when the compound of the invention is administered intravenously. Saline solutions and aqueous dextrose and glycerol solutions can also be employed as liquid vehicles, particularly for injectable solutions. Suitable pharmaceutical vehicles also include excipients such as starch, glucose, lactose, sucrose, gelatin, malt, rice, flour, chalk, silica gel, sodium stearate, glycerol monostearate, talc, sodium chloride, dried skim milk, glycerol, propyleneglycol, water, ethanol and the like. The present compositions, if desired, can also contain minor amounts of wetting or emulsifying agents, or pH buffering agents.

The present compositions can take the form of solutions, suspensions, emulsion, tablets, pills, pellets, capsules, capsules containing liquids, powders, sustained-release formulations, suppositories, emulsions, aerosols, sprays, suspensions, or any other form suitable for use. In one embodiment, the pharmaceutically acceptable vehicle is a capsule (see e.g., U.S. Pat. No. 5,698,155). Other examples of suitable pharmaceutical vehicles are described in "Remington's Pharmaceutical Sciences" by E. W. Martin.

In a preferred embodiment, the compounds of the invention are formulated in accordance with routine procedures as a pharmaceutical composition adapted for intravenous administration to human beings. Typically, compounds of the invention for intravenous administration are solutions in sterile isotonic aqueous buffer. Where necessary, the compositions may also include a solubilizing agent. Compositions for intravenous administration may optionally include a local anesthetic such as lignocaine to ease pain at the site of the injection. Generally, the ingredients are supplied either separately or mixed together in unit dosage form, for example, as a dry lyophilized powder or water free concentrate in a hermetically sealed container such as an ampoule or sachette indicating the quantity of active agent. Where the compound of the invention is to be administered by infusion, it can be dispensed, for example, with an infusion bottle containing sterile pharmaceutical grade water or saline. Where the compound of the invention is administered by injection, an ampoule of sterile water for injection or saline can be provided so that the ingredients may be mixed prior to administration.

Compositions for oral delivery may be in the form of tablets, lozenges, aqueous or oily suspensions, granules, powders, emulsions, capsules, syrups, or elixirs, for example. Orally administered compositions may contain one or more optional agents, for example, sweetening agents such as fructose, aspartame or saccharin; flavoring agents such as peppermint, oil of wintergreen, or cherry; coloring agents; and preserving agents, to provide a pharmaceutically palatable preparation. Moreover, where in tablet or pill form, the compositions may be coated to delay disintegration and absorption in the gastrointestinal tract thereby providing a sustained action over an extended period of time. Selectively permeable membranes surrounding an osmotically active driving compound are also suitable for orally administered compounds of the invention. In these later platforms, fluid from the environment surrounding the capsule is imbibed by the driving compound, which swells to displace the agent or agent composition through an aperture. These delivery platforms can provide an essentially zero order delivery profile as opposed to the spiked profiles of immediate release formulations. A time delay material such as glycerol monostearate or glycerol stearate may also be used. Oral compositions can include standard vehicles such as mannitol, lactose, starch, magnesium stearate, sodium saccharine, cellulose, magnesium carbonate, etc. Such vehicles are preferably of pharmaceutical grade.

Further, the effect of the compounds of this invention may be delayed or prolonged by proper formulation. For example, a slowly soluble pellet of the compound may be prepared and incorporated in a tablet or capsule. The technique may be improved by making pellets of several different dissolution rates and filling capsules with a mixture of the pellets. Tablets or capsules may be coated with a film which resists dissolution for a predictable period of time. Even the parenteral preparations may be made long-acting, by dissolving or suspending the compound in oily or emulsified vehicles which allow it to disperse only slowly in the serum.

4.2.1 Formulations

Pharmaceutical compositions for use in accordance with the present invention may be formulated in conventional manner using one or more physiologically acceptable carriers or excipients.

Thus, the JNK inhibitors or other anti-cancer agents and their physiologically acceptable salts and solvates may be formulated for administration by inhalation or insufflation (either through the mouth or the nose) or oral, parenteral or mucosol (such as buccal, vaginal, rectal, sublingual) administration. In a preferred embodiment, local or systemic parenteral administration is used.

For oral administration, the pharmaceutical compositions may take the form of, for example, tablets or capsules prepared by conventional means with pharmaceutically acceptable excipients such as binding agents (e.g., pregelatinised maize starch, polyvinylpyrrolidone or hydroxypropyl methylcellulose); fillers (e.g., lactose, microcrystalline cellulose or calcium hydrogen phosphate); lubricants (e.g., magnesium stearate, talc or silica); disintegrants (e.g., potato starch or sodium starch glycolate); or wetting agents (e.g., sodium lauryl sulphate). The tablets may be coated by methods well known in the art. Liquid preparations for oral administration may take the form of, for example, solutions, syrups or suspensions, or they may be presented as a dry product for constitution with water or other suitable vehicle before use. Such liquid preparations may be prepared by conventional means with pharmaceutically acceptable additives such as suspending agents (e.g., sorbitol syrup, cellulose derivatives or hydrogenated edible fats); emulsifying agents (e.g., lecithin or acacia); non-aqueous vehicles (e.g., almond oil, oily esters, ethyl alcohol or fractionated vegetable oils); and preservatives (e.g., methyl or propyl-p-hydroxybenzoates or sorbic acid). The preparations may also contain buffer salts, flavoring, coloring and sweetening agents as appropriate.

Preparations for oral administration may be suitably formulated to give controlled release of the active compound.

For buccal administration the compositions may take the form of tablets or lozenges formulated in conventional manner.

For administration by inhalation, the prophylactic or therapeutic agents for use according to the present invention are conveniently delivered in the form of an aerosol spray presentation from pressurized packs or a nebuliser, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of e.g., gelatin for use in an inhaler or insufflator may be formulated containing a powder mix of the compound and a suitable powder base such as lactose or starch.

The prophylactic or therapeutic agents may be formulated for parenteral administration by injection, e.g., by bolus injection or continuous infusion. Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents. Alternatively, the active ingredient may be in powder form for constitution with a suitable vehicle, e.g., sterile pyrogen-free water, before use.

The prophylactic or therapeutic agents may also be formulated in rectal compositions such as suppositories or retention enemas, e.g., containing conventional suppository bases such as cocoa butter or other glycerides.

In addition to the formulations described previously, the prophylactic or therapeutic agents may also be formulated as a depot preparation. Such long acting formulations may be administered by implantation (for example subcutaneously or intramuscularly) or by intramuscular injection. Thus, for example, the prophylactic or therapeutic agents may be formulated with suitable polymeric or hydrophobic materials (for example as an emulsion in an acceptable oil) or ion exchange resins, or as sparingly soluble derivatives, for example, as a sparingly soluble salt.

The invention also provides that a prophylactic or therapeutic agent is packaged in a hermetically sealed container such as an ampoule or sachette indicating the quantity. In one embodiment, the prophylactic or therapeutic agent is supplied as a dry sterilized lyophilized powder or water free concentrate in a hermetically sealed container and can be reconstituted, e.g., with water or saline to the appropriate concentration for administration to a patient.

In a preferred embodiment of the invention, the formulation and administration of various chemotherapeutic, biological/immunotherapeutic and hormonal therapeutic agents are known in the art and often described in the *Physician's Desk Reference*, 56$^{th}$ ed. (2002). For instance, in certain specific embodiments of the invention, the therapeutic agents of the invention can be formulated and supplied as provided in Table 1.

In other embodiments of the invention, radiation therapy agents such as radioactive isotopes can be given orally as liquids in capsules or as a drink. Radioactive isotopes can also be formulated for intravenous injections. The skilled oncologist can determine the preferred formulation and route of administration.

The compositions may, if desired, be presented in a pack or dispenser device that may contain one or more unit dosage forms containing the active ingredient. The pack may for example comprise metal or plastic foil, such as a blister pack. The pack or dispenser device may be accompanied by instructions for administration.

In certain preferred embodiments, the pack or dispenser contains one or more unit dosage forms containing no more than 5 mg/mL of a JNK inhibitor and no more than the recommended dosage formulation as determined in the *Physician's Desk Reference* (56$^{th}$ ed. 2002, herein incorporated by reference in its entirety) for a particular cancer therapy.

4.4 Routes of Administration

Methods of administering a prophylactic or therapeutic agent of the invention include, but are not limited to, parenteral administration (e.g., intradermal, intramuscular, intraperitoneal, intravenous and subcutaneous), epidural, and mucosal (e.g., intranasal, rectal, vaginal, sublingual, buccal or oral routes). In a specific embodiment, prophylactic or therapeutic agents of the invention are administered intramuscularly, intravenously, or subcutaneously. The prophylactic or therapeutic agents may also be administered by infusion or bolus injection and may be administered together with other biologically active agents. Administration can be local or systemic. The JNK inhibitors or other biologically active agents and their physiologically acceptable salts and solvates may also be administered by inhalation or insufflation (either through the mouth or the nose). In a preferred embodiment, local or systemic parenteral administration is used.

In specific embodiments, it may be desirable to administer one or more compounds of the invention locally to the area in need of treatment. This may be achieved, for example, and not by way of limitation, by local infusion during surgery, topical application, e.g., in conjunction with a wound dressing after surgery, by injection, by means of a catheter, by means of a suppository, or by means of an implant, said implant being of a porous, non-porous, or gelatinous material, including membranes, such as sialastic membranes, or fibers. In one embodiment, administration can be by direct injection at the site (or former site) of an atherosclerotic plaque tissue.

Pulmonary administration can also be employed, e.g., by use of an inhaler or nebulizer, and formulation with an aerosolizing agent, or via perfusion in a fluorocarbon or synthetic pulmonary surfactant. In certain embodiments, the compounds of the invention can be formulated as a suppository, with traditional binders and vehicles such as triglycerides.

In another embodiment, the compounds of the invention can be delivered in a vesicle, in particular a liposome (see Langer, 1990, *Science* 249:1527-1533; Treat et al., in Liposomes in the Therapy of Infectious Disease and Cancer, Lopez-Berestein and Fidler (eds.), Liss, N.Y., pp. 353-365 (1989); Lopez-Berestein, ibid., pp. 317-327; see generally ibid.).

In yet another embodiment, the compounds of the invention can be delivered in a controlled release system. In one embodiment, a pump may be used (see Langer, supra; Sefton, 1987, *CRC Crit. Ref. Biomed. Eng.* 14:201; Buchwald et al., 1980, *Surgery* 88:507 Saudek et al., 1989, *N. Engl. J. Med.* 321:574). In another embodiment, polymeric materials can be used (see Medical Applications of Controlled Release, Langer and Wise (eds.), CRC Pres., Boca Raton, Fla. (1974); Controlled Drug Bioavailability, Drug Product Design and Performance, Smolen and Ball (eds.), Wiley, N.Y. (1984); Ranger and Peppas, 1983, *J. Macromol. Sci. Rev. Macromol. Chem.* 23:61; see also Levy et al., 1985, *Science* 228:190; During et al., 1989, *Ann. Neurol.* 25:351; Howard et al., 1989, *J. Neurosurg.* 71:105). In yet another embodiment, a controlled-release system can be placed in proximity of the target of the compounds of the invention, e.g., the liver, thus requiring only a fraction of the systemic dose (see, e.g., Goodson, in Medical Applications of Controlled Release, supra, vol. 2, pp. 115-138 (1984)). Other controlled-release systems discussed in the review by Langer, 1990, *Science* 249:1527-1533) may be used.

4.5 Dosages

The amount of the composition of the invention which will be effective in the treatment, prevention or management of cancer can be determined by standard research techniques. For example, the dosage of the composition which will be effective in the treatment, prevention or management of cancer can be determined by administering the composition to an animal model such as, e.g., the animal models disclosed herein or known to those skilled in the art. In addition, in vitro assays may optionally be employed to help identify optimal dosage ranges.

Selection of the preferred effective dose can be determined (e.g., via clinical trials) by a skilled artisan based upon the consideration of several factors which will be known to one of ordinary skill in the art. Such factors include the disease to be treated or prevented, the symptoms involved, the patient's body mass, the patient's immune status and other factors known by the skilled artisan to reflect the accuracy of administered pharmaceutical compositions.

The precise dose to be employed in the formulation will also depend on the route of administration, and the seriousness of the cancer, and should be decided according to the judgment of the practitioner and each patient's circumstances. Effective doses may be extrapolated from dose-response curves derived from in vitro or animal model test systems.

The general range of effective administration rates of the compounds of this invention are from about 0.001 mg/day to about 3000 mg/day, more preferably from about 0.001 mg/day to 2500 mg/day, more preferably from about 0.001 mg/day to 1500 mg/day, more preferably from about 0.001 mg/day to 750 mg/day, more preferably from about 0.001 mg/day to 250 mg/day, more preferably from about 0.001 mg/day to 75 mg/day, more preferably from about 0.001 mg/day to 50 mg/day, more preferably from about 0.001 mg/day to 25 mg/day, more preferably from about 0.001 mg/day to 10 mg/day, more preferably from about 0.001 mg/day to 1 mg/day. Of course, it is often practical to administer the daily dose of compound in portions, at various hours of the day. However, in any given case, the amount of compound administered will depend on such factors as the solubility of the active component, the formulation used, subject condition (such as weight), and/or the route of administration.

For antibodies, the dosage administered to a patient is typically 0.1 mg/kg to 100 mg/kg of the patient's body weight. Preferably, the dosage administered to a patient is between 0.1 mg/kg and 20 mg/kg of the patient's body weight, more preferably 1 mg/kg to 10 mg/kg of the patient's body weight. Generally, human and humanized antibodies have a longer half-life within the human body than antibodies from other species due to the immune response to the foreign polypeptides. Thus, lower dosages of human antibodies and less frequent administration is often possible.

For other cancer therapeutic agents administered to a patient, the typical doses of various cancer therapeutics known in the art are provided in Table 1. Given the invention, certain preferred embodiments will encompass the administration of lower dosages in combination treatment regimens than dosages recommended for the administration of single agents.

Cancer therapies and their dosages, routes of administration and recommended usage are known in the art and have been described in such literature as the *Physician's Desk Reference* (56$^{th}$ ed., 2002).

The invention provides for any method of administrating lower doses of known prophylactic or therapeutic agents than previously thought to be effective for the prevention, treatment, management or amelioration of cancer. Preferably, lower doses of known anti-cancer therapies are administered in combination with lower doses of JNK inhibitors.

4.6 Kits

The invention provides a pharmaceutical pack or kit comprising one or more containers filled with JNK inhibitor and one or more other prophylactic or therapeutic agents useful for the treatment of a cancer. The invention also provides a pharmaceutical pack or kit comprising one or more containers filled with one or more of the ingredients of the pharmaceutical compositions of the invention. Optionally associated with such container(s) can be a notice in the form prescribed by a governmental agency regulating the manufacture, use or sale of pharmaceuticals or biological products, which notice reflects approval by the agency of manufacture, use or sale for human administration.

The present invention provides kits that can be used in the above methods. In one embodiment, a kit comprises a JNK inhibitor, in one or more containers, and one or more other prophylactic or therapeutic agents useful for the treatment of cancer, in one or more containers. In certain preferred embodiments, the other prophylactic or therapeutic agent is a chemotherapeutic. In certain preferred embodiments, the prophylactic or therapeutic agent is a biological or hormonal therapeutic. In an alterative embodiment, a kit comprises a JNK inhibitor and one or more other prophylactic or therapeutic agents useful for the treatment of cancer, in one or more containers.

5. EXAMPLES

The following examples are offered by way of illustration, not limitation.

5.1 JNK Inhibitor A and JNK Inhibitor B in Combination Therapy Using Lewis Lung Carcinoma (LLC)

This experiment was performed in vitro to determine the effect on Lewis Lung Carcinoma (LLC) proliferation of combination treatment with JNK inhibitor A and JNK inhibitor B (JNK inhibitor A=((2H-Dibenzo(cd,g)indazol-6-one)); JNK inhibitor B=(3-(4-fluoro-phenyl)-5-(2H-(1,2,4-triazol-3-yl)-1H-indazole)) and anti-cancer agents. The results are illustrated in FIGS. 1A and 1B.

LLC cells were grown in DMEM with 10% FBS. Cells were subsequently treated on the second day with either DMSO, JNK inhibitor A (3 µM, 10 µM or 30 µM), JNK inhibitor B (1 µM, 3 µM, or 10 µM), or a chemodrug (i.e., doxorubican, 5-fluorouridine (5-FU), cisplatin or paclitaxel) (concentrations ranging from 0.001 µM to 10 µM) or a combination of JNK inhibitor A or JNK inhibitor B with a chemodrug. Cell proliferation was measured at 48 hours after treatment by Alamar Blue fluorescence.

Treatment of cells with a combination of JNK inhibitor A or JNK inhibitor B and a chemodrug resulted in increased killing of cells relative to treatment with JNK inhibitor A or JNK inhibitor B or a chemodrug alone.

5.2 Combination of JNK Inhibitor B and Cyclophosphamide Blocks Lewis Lung Carcinoma (LLC) Tumor Growth This experiment was performed to determine if JNK inhibitors will enhance the antitumor effects of cyclophosphamide (CTX) in combination treatment. Results are illustrated in FIG. 2.

Lewis Lung Carcinoma (LLC) tumors were injected into C57BL/6 mice (50 mice, 10/group), 1×10⁶ cells in 0.1 ml Matrigel. Tumors were treated the day after inoculation by administration of vehicle alone (0.5% CMC/0.25% Tween 80), cyclophosphamide (CTX, 50 mg/kg, ip, q3d), SPC2 (75 mg/kg, ip, b.i.d.) or CTX in combination with JNK inhibitor B. Tumor volume was recorded over a period of 17 days. Tumor volume was calculated by the formula: mm³=(L× W²)/2. In the CTX/JNK inhibitor B combination group, 7/10 animals had no measurable tumors at the end of the study.

These results demonstrate the additive if not synergistic effect on tumor reduction by combination treatment with a JNK inhibitor and anti-cancer agent.

5.3 JNK Inhibitor A Potentiates Chemotherapeutic Induction of Apoptosis

The following experiment was performed to determine the effectiveness of combination treatment with JNK inhibitor A and a chemodrug on apoptosis. The results are illustrated in FIG. 3.

MiaPaCa cells (100,000/well) were plated in 6 well plates. Following overnight incubation, vehicle or taxol was added alone for the first 7 hours, washed out, and then JNK inhibitor A or vehicle were added for the remainder of the experiment. After 48 hours, each sample was trypsinized, stained with DiOC6 and analyzed by flow cytometry on a Coulter Epics flow cytometer using FlowJo software.

The results demonstrate the effect on MiaPaCa cell apoptosis by combination treatment with JNK inhibitor A and taxol as compared to treatment with taxol alone.

5.4 Combination of JNK Inhibitor A and Cyclophosphamide Blocks Lewis Lung Carcinoma (LLC) Tumor Growth The following experiment was performed to determine the effectiveness of combination treatment with JNK inhibitor A and cyclophosphamide. The results are illustrated in FIG. 4.

Tumor cells were cultured under normal conditions, harvested with trypsin, washed with PBS then resuspended, 1×107 cells/ml in Matrigel (Collaborative). C57BL/6 mice (female, 18-20 g, Charles River) were lightly anesthetized using Isofluorane then inoculated, subcutaneously, under the right flank with 0.1 ml Matrigel containing 1×106 tumor cells. Mice were randomized into treatment groups immediately after cell inoculation. After 3 days tumor growth treatment began. Mice were administered vehicle alone (DMSO), cyclophosphamide (CTX), JNK inhibitor A or CTX in combination with JNK inhibitor A. Tumor volumes were determined by caliper measurement. Tumor volume was calculated by the formula: mm³=(L×W2)/2. Values are mean±sem, N=10. This study demonstrates the antitumor effects of JNK inhibitor A in combination with cyclophosphamide in C57BL/6 mice bearing Lewis lung carcinoma. Tumor inhibition resulting from JNK inhibitor A treatment in combination with cyclophosphamide was significantly less (p=0.05) than that seen with cyclophosphamide alone. This result indicates that JNK inhibitors can be used in combination with cyclophosphamide and other chemotherapeutic drugs to enhance their efficacy.

5.5 Combination of JNK Inhibitor C and Camptosar Blocks Lewis Lung Carcinoma (LLC) Tumor Growth The following experiment was performed to determine the effectiveness of combination treatment with JNK inhibitor C (JNK inhibitor C=(3-(4-(2-Piperidin-1-yl-ethoxy)-cyclohexa-1,5-dienyl)-5-(2H-(1,2,4)triazol-3-yl)-1H-indazole)) and Camptosar. The results are illustrated in FIG. 5.

CB17 SCID mice were inoculated subcutaneously with HCT-116 human colorectal cancer cells. On day 8, mice bearing tumors of 100 mm³ were segregated into groups and administered i.p. with vehicle (citrate buffer), JNK inhibitor C (15 mg/kg), JNK inhibitor C (30 mg/kg), JNK inhibitor C (15 mg/kg)+Camptosar (1.5 mg/kg), Camptosar (1.5 mg/kg) or Camptosar (10 mg/kg). The tumors were measured twice a week and volumes calculated. The dosing regimen for the compound JNK inhibitor C was b.i.d and for Camptosar was q4d. The arrows indicate the dosing days of JNK inhibitor C and Camptosar. The tumor growth in the group treated with JNK inhibitor C in combination with Camptosar was significantly slower than that of either treatments alone. This demonstrates the synergistic effect of combination therapy with JNK inhibitor C and Camptosar.

What is claimed is:

1. A method for treating lung cancer or leukemia in a patient in need thereof, said method comprising administering to said patient a therapeutically effective amount of one or more JNK inhibitors and a therapeutically effective amount of a chemotherapeutic agent, wherein the JNK inhibitor is:

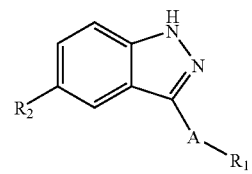

wherein:
(a) -A-$R_1$ is phenyl, optionally substituted with one to four substituents independently selected from halogen, alkoxy, —$NR_8C(=O)R_9$, —$C(=O)NR_8R_9$, and —$O(CH_2)_bNR_8R_9$, wherein b is 2 or 3 and $R_8$ and $R_9$ are the same or different and at each occurrence independently hydrogen, alkyl, aryl, arylalkyl, heterocycle, or heterocycloalkyl, or $R_8$ and $R_9$ taken together with the atom or atoms to which they are bonded form a heterocycle; and
(b) $R_2$ is 3-triazolyl or 5-tetrazolyl;
or a pharmaceutically acceptable salt thereof.

2. The method of claim 1, wherein the chemotherapeutic agent is paclitaxel.

3. The method of claim 1, wherein the chemotherapeutic agent is cyclophosphamide.

4. The method of claim 1, wherein said leukemia is acute myelocytic leukemia.

5. The method of claim 4, wherein said acute myelocytic leukemia is myeloblastic, promyelocytic, myelomonocytic, monocytic, erythroleukemia leukemias or myelodysplastic syndrome.

6. The method of claim 1, wherein the chemotherapeutic agent is an apoptosis inducing agent.

7. The method of claim 1, wherein the JNK inhibitor and chemotherapeutic agent are administered concurrently.

8. The method of claim 1, wherein the JNK inhibitor and chemotherapeutic agent are administered sequentially.

* * * * *